United States Patent
Marks et al.

(10) Patent No.: US 12,400,733 B2
(45) Date of Patent: Aug. 26, 2025

(54) IN SITU CODE DESIGN METHODS FOR MINIMIZING OPTICAL CROWDING

(71) Applicant: 10x Genomics, Inc., Pleasanton, CA (US)

(72) Inventors: Patrick J. Marks, Paris (FR); Preyas Shah, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 18/827,279

(22) Filed: Sep. 6, 2024

(65) Prior Publication Data

US 2024/0428880 A1  Dec. 26, 2024

Related U.S. Application Data

(63) Continuation of application No. PCT/US2023/063866, filed on Mar. 7, 2023.
(Continued)

(51) Int. Cl.
| | |
|---|---|
| *G16B 15/00* | (2019.01) |
| *G16B 25/20* | (2019.01) |
| *G16B 50/50* | (2019.01) |

(52) U.S. Cl.
CPC ............ *G16B 15/00* (2019.02); *G16B 25/20* (2019.02); *G16B 50/50* (2019.02); *G01N 2333/08* (2013.01)

(58) Field of Classification Search
None
See application file for complete search history.

(56) References Cited

U.S. PATENT DOCUMENTS

| | | |
|---|---|---|
| 5,635,352 A | 6/1997 | Urdea et al. |
| 5,695,940 A | 12/1997 | Drmanac et al. |

(Continued)

FOREIGN PATENT DOCUMENTS

| | | |
|---|---|---|
| WO | WO 2017/143155 | 8/2017 |
| WO | WO 2019/199579 | 10/2019 |

(Continued)

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.

(Continued)

*Primary Examiner* — Haris Sabah
(74) *Attorney, Agent, or Firm* — MORRISON & FOERSTER LLP

(57) ABSTRACT

Methods and systems for performing in situ decoding are described that minimize optical crowding, thereby improving decoding accuracy. The methods may comprise, e.g., receiving images of a biological sample acquired during a cyclical decoding process; detecting a series of detectable signals (ON signals) or absence thereof (OFF signals) at one or more locations in the biological sample corresponding to one or more barcoded target analytes; determining a code word based on the series of ON and OFF signals that corresponds to a barcode for each of the one or more barcoded target analytes, where the one or more code words are assigned to the one or more barcoded target analytes based on a minimax decision rule to minimize a density of ON signals detected in the images of the series of images; and identifying the one or more barcoded target analytes based on the one or more determined code words.

26 Claims, 11 Drawing Sheets

Related U.S. Application Data

(60) Provisional application No. 63/317,842, filed on Mar. 8, 2022.

(56) References Cited

U.S. PATENT DOCUMENTS

| | | |
|---|---|---|
| 6,306,597 B1 | 10/2001 | Macevicz |
| 6,534,266 B1 | 3/2003 | Singer |
| 7,255,994 B2 | 8/2007 | Lao |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,655,898 B2 | 2/2010 | Miller |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,648,072 B2 * | 5/2020 | Ries ................ C23C 14/562 |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0063190 A1 * | 2/2020 | Chenchik ............ C12Q 1/686 |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0065849 A1 * | 3/2022 | Griffiths ............ C12Q 1/6806 |
| 2022/0083832 A1 | 3/2022 | Shah |
| 2022/0084628 A1 | 3/2022 | Shah |
| 2022/0084629 A1 | 3/2022 | Shah |

(56) References Cited

U.S. PATENT DOCUMENTS

| | | |
|---|---|---|
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0333191 A1* | 10/2022 | Mikkelsen ......... C12N 15/1003 |
| 2022/0372570 A1 | 11/2022 | Costa |
| 2022/0380838 A1 | 12/2022 | Kuhnemund et al. |
| 2022/0389503 A1* | 12/2022 | Mikkelsen ........... C12N 5/0602 |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Neuta et al. |
| 2023/0031996 A1 | 2/2023 | Neuta et al. |
| 2023/0035685 A1 | 2/2023 | Neuta et al. |
| 2023/0037182 A1 | 2/2023 | Bava et al. |
| 2023/0039148 A1 | 2/2023 | Verheyen |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0081232 A1* | 3/2023 | Weisenfeld ............ G06V 20/69 382/133 |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0238078 A1* | 7/2023 | Gonzalez Lozano ....................... G06T 7/0012 382/128 |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Burgess, D., "Spatial transcriptomics coming of age," Nat Rev Genet. (2019) 20(6):317.

Buschmann et al., "Levenshtein error-correcting barcodes for multiplexed DNA sequencing," BMC Bioinformatics. (2013) 11:14:272.

Capodieci et al., "Gene expression profiling in single cells within tissue," Nat Methods. (2005) 2(9): 663-5.

Conze et al., "Single molecule analysis of combinatorial splicing," Nucleic Acids Res. (2010) 38(16): e163.

D'Alessio et al., "A Coding Theory Perspective on Multiplexed Molecular Profiling of Biological Tissues," Arxiv. Org, , Cornell University Library, 201 Olin Library Cornell University Ithaca, NY 14853; Feb. 2, 2021.

Eng et al., "Transcriptome-scale super-resolved imaging in tissues by RNA seqFISH," Nature. (2019) 568(7751): 235-239.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

(56) References Cited

OTHER PUBLICATIONS

Levsky et al., "Single-cell gene expression profiling," Science. (2002) 297(5582): 836-40.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Moffitt et al., "RNA Imaging with Multiplexed Error-Robust Fluorescence In Situ Hybridization (MERFISH)," Methods in Enzymology, (2016) 572; 1-49.
Payne et al. "In situ genome sequencing resolves DNA sequence and structure in intact biological samples," Science. (2021) 371(6532): eaay3446. doi: 10.1126/science.aay3446. Epub Dec. 31, 2020.
Raj et al., "Imaging individual mRNA molecules using multiple singly labeled probes," Nat Methods. (2008) 5(10): 877-879.
Rouhanifard et al. "ClampFISH detects individual nucleic acid molecules using click chemistry-based amplification," Nat Biotechnol. (2018) 17 pages. doi: 10.1038/nbt.4286.
Soares et al., "Rolling Circle Amplification in Integrated Microsystems: An Uncut Gem toward Massively Multiplexed Pathogen Diagnostics and Genotyping," Acc Chem Res. (2021) 54(21):3979-3990.
Strell et al., "Placing RNA in context and space—methods for spatially resolved transcriptomics," FEBS J. (2019) 286(8):1468-1481.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Wu et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Xia et al., "Spatial transcriptome profiling by MERFISH reveals subcellular RNA compartmentalization and cell cycle-dependent gene expression," Proc Natl Acad Sci USA. (2019) 116(39):19490-19499.
Zhao et al., "Advances of multiplex and high throughput biomolecular detection technologies based on encoding microparticles," Sci China Chem. (2011) 54(8):1185.
Zhuang et al., "Spatially resolved single-cell genomics and transcriptomics by imaging," Nat Methods. (2021) 18(1):18-22.
Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.

\* cited by examiner

IN SITU CODE DESIGN METHODS FOR MINIMIZING OPTICAL CROWDING

CROSS-REFERENCE TO RELATED APPLICATIONS

This application is a continuation of International Application No. PCT/US2023/063866, filed On Mar. 7, 2024, which claims the priority benefit of U.S. Provisional Patent Application Ser. No. 63/317,842, filed on Mar. 8, 2022, the contents of which are incorporated herein by reference in their entirety.

FIELD OF THE DISCLOSURE

The present disclosure relates generally to methods and systems for in situ detection and analysis, and more specifically to methods for the design and assignment of barcodes to target analytes that minimize optical crowding.

BACKGROUND OF THE DISCLOSURE

In situ detection and analysis methods are emerging from the rapidly developing field of spatial transcriptomics. The key objectives in spatial transcriptomics are to detect, quantify, and map gene activity to specific regions in a tissue sample at cellular or sub-cellular resolution. These techniques allow one to study the subcellular distribution of gene activity (as evidenced, e.g., by expressed gene transcripts), and have the potential to provide crucial insights in the fields of developmental biology, oncology, immunology, histology, etc.

In situ decoding is a process comprising a plurality of decoding cycles in each of which a different set of barcode probes (e.g., fluorescently-labeled oligonucleotides) is contacted with target analytes (e.g., mRNA sequences) or with target barcodes (e.g., nucleic acid barcodes) associated with the target analytes present in a sample (e.g., a tissue sample) under conditions that promote hybridization. One or more images (e.g., fluorescence images) are acquired in each decoding cycle, and the images are processed to detect the presence and locations of one or more barcode probes in each cycle. The presence and locations of one or more target analyte sequences or associated barcode sequences are then inferred from corresponding code words that are determined based on the set of, e.g., fluorescence signals detected in each decoding cycle of the decoding process.

Optical crowding (a condition under which the ability to extract fluorescence signal intensities for individual objects or features (e.g., fluorescently-labeled, barcoded target analytes, or amplified proxies thereof) from images acquired during the decoding process is hindered by the limits of optical resolution and the density of target analytes in a biological sample) is a key limitation of in situ analysis and interferes with the accurate decoding and detection of target analytes. Methods to minimize or eliminate the effects of optical crowding will thus be important for improving the accuracy and sensitivity of in situ analysis techniques for detecting and quantifying target analytes in biological samples.

SUMMARY OF THE DISCLOSURE

Methods to minimize or eliminate the effects of optical crowding during detection and decoding of barcoded target analytes will be critical for implementing accurate and sensitive in situ analysis techniques. Disclosed herein are codebook design strategies and methods for minimizing the impact of optical crowding on the detection and decoding of barcoded target analytes when the density of fluorescing barcoded target analytes (e.g., detectably labeled probes, fluorescing rolling circle amplification products (RCPs) of barcoded gene transcripts) approaches a threshold where it becomes difficult to resolve detectably labeled probes or individual spots (e.g., fluorescing RCPs or "ON RCPs") in the images used for decoding. Optical crowding can be minimized by minimizing the number of times each barcoded target analyte (e.g., an RCP) must be observed in the ON state during the decoding process, and designing the code words assigned to the target analytes such that the total set of ON states is distributed more-or-less evenly over the plurality of decoding cycles and detection channels used for decoding. Separate but complementary techniques for minimizing optical crowding are described: (i) code word dilution (e.g., an approach in which the code words in a set of code words (i.e., a "code book") are designed to have the smallest possible weights (the code word weight is the total number of ON bits in a given code word; it determines how often the corresponding barcoded target analyte will be visible/detectable during the decoding process), (ii) optimized assignment of code words to target analytes (e.g., an approach in which code words are assigned to corresponding barcoded target analytes according to, e.g., single cell expression data for the target analytes in clustered cell types to reduce the weight of code words corresponding to highly expressed target analytes, where the clustered cell types represent a distribution of cell types found in the biological sample), and to avoid the co-occurrence of two abundant genes that are expressed in the same cell type appearing in the ON state in the same decoding cycle, (iii) target probe code word splitting (e.g., an approach in which two or more barcodes are assigned to a same target analyte (e.g., by incorporation into two or more anchor probes used to implement rolling circle amplification), where each barcode has a different corresponding code word assigned) and (iv) gene attenuation (e.g., instances where all of the bits for a code word corresponding to one of the two or more barcodes assigned to the barcoded target analyte are OFF bits, thereby reducing the sensitivity of detecting highly expressed target analytes).

Disclosed herein are methods for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identifying the one or more barcoded target analytes based on the one or more determined code words.

Also disclosed herein are methods for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule that ensures that a total number of ON signals detected in an image for a given decoding cycle is within ±20% of a mean number of ON signals detected per image for the series of images; and identifying the one or more barcoded target analytes based on the one or more determined code words. In some embodiments, the one or more code words are assigned to the one or more barcoded target analytes based on a decision rule that ensures that a total number of ON signals detected in an image for a given decoding cycle is within ±10% of a mean number of ON signals detected per image for the series of images.

In some embodiments of any of the methods described herein, a majority of the bits in each of the one or more code words are OFF bits. In some embodiments, each of the one or more code words comprises a same total number of ON bits. In some embodiments, the one or more code words are assigned to the one or more barcoded target analytes based on a decision rule that also ensures that a total number of ON signals detected in a given image of the series of images corresponds to a total number of barcoded target analytes that is within ±20% of a mean number of barcoded target analytes detected per image for the series of images. In some embodiments, the one or more code words are assigned to the one or more barcoded target analytes based on a decision rule that ensures that the total number of ON signals detected in a given image of the series of images corresponds to a total number of barcoded target analytes that is within ±10% of a mean number of barcoded target analytes detected per image for the series of images.

In some embodiments of any of the methods described herein, the decision rule for assignment of the one or more code words to the one or more barcoded target analytes further comprises assignment based on expression data for the one or more target analytes in clustered cell types, and wherein the clustered cell types represent a distribution of cell types found in the biological sample. In some embodiments, the expression data for the one or more target analytes comprises bulk gene expression data, bulk protein expression data, spatial gene expression data, spatial protein expression data, single cell gene expression data, single cell protein expression data, or any combination thereof. In some embodiments, the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some embodiments, the iterative process further comprises reviewing previous assignments of code words to barcoded target analytes, and changing the code word selected for the current barcoded target analyte to minimize the predicted density of ON signals across the series of images for barcoded target analytes to which code words have been previously assigned. In some embodiments, the iterative process is performed using a greedy algorithm, a simulated annealing algorithm, or a combination thereof. In some embodiments, the one or more code words are rank-ordered according to code word weight, the one or more barcoded target analytes are rank-ordered according to a maximum expression level across all clustered cell types, and the lowest ranked code word is assigned to the highest ranked barcoded target analyte.

In some embodiments, of any of the methods described herein, two or more barcodes are assigned to a barcoded target analyte, and the method further comprises: determining a code word that corresponds to one of the two or more barcodes assigned to the barcoded target analyte based on the series of ON and OFF signals detected in the series of images; and identifying the barcoded target analyte based on the determined code word. In some embodiments, 3, 4, 5, 6, 7, 8, 9, 10, 11, 12, 13, 14, 15, or 16 barcodes are assigned to the barcoded target analyte. In some embodiments, the method further comprises determining a logical OR code word that corresponds to two of the two or more barcodes assigned to the barcoded target analyte based on the series of ON and OFF signals detected in the series of images; and identifying the barcoded target analyte based on the logical OR code word. In some embodiments, all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes. In some embodiments, an error rate for decoding the one or more barcoded target analytes is reduced compared to that when the one or more code words are randomly assigned to the one or more barcoded target analytes.

In some embodiments of any of the methods described herein, the identification of the one or more barcoded target analytes comprises a qualitative detection of the one or more barcoded target analytes. In some embodiments, the identification of the one or more barcoded target analytes comprises a quantitative detection of the one or more barcoded target analytes. In some embodiments, the detectable signal comprises a fluorescence signal. In some embodiments, each code word comprises N×K bits, where N is the number of decoding cycles and K is the number of detection channels. In some embodiments, the barcoded target analytes comprise barcoded gene sequences, barcoded gene transcripts, barcoded proteins, or any combination thereof.

Disclosed herein are methods comprising: contacting a biological sample with a plurality of primary probes configured to hybridize to a plurality of target analytes, wherein each primary probe comprises a target analyte-specific barcode sequence and an anchor probe binding sequence; performing in situ rolling circle amplification (RCA) to produce a plurality of rolling circle amplification produces (RCPs) within the biological sample, each RCP comprising multiple copies of a target analyte sequence, a target analyte-specific barcode sequence, and an anchor probe binding sequence; contacting the plurality of RCPs within the biological sample with a first detectably labeled anchor probe configured to hybridize to anchor probe binding sequences present in all or a portion of the plurality of RCPs; and for each of a plurality of decoding cycles, performing the steps of: contacting the plurality of RCPs within the biological sample with a plurality of bridge probes, each configured to hybridize to a target analyte-specific barcode sequence present within the plurality of RCPs; contacting the hybridized bridge probes with a plurality of detectably labeled detection probes, each configured to hybridize to one or more bridge probes of the plurality of hybridized bridge probes; acquiring an image of the biological sample in each decoding cycle of the plurality of decoding cycles to obtain a series of images; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identifying the one or more barcoded target analytes based on the one or more determined code words.

In some embodiments, the plurality of bridge probes may be different for different decoding cycles. In some embodiments, the plurality of detectably labeled detection probes may be different for different decoding cycles. In some embodiments, a majority of the bits in each code word for the one or more barcoded target analytes are OFF bits. In some embodiments, each of the one or more code words comprises a same total number of ON bits. In some embodiments, the decision rule for the assignment of the one or more code words to the one or more barcoded target analytes further comprises assignment based on expression data for the one or more target analytes in clustered cell types, and wherein the clustered cell types represent a distribution of cell types found in the biological sample. In some embodiments, the expression data for the one or more target analytes comprises bulk gene expression data, bulk protein expression data, spatial gene expression data, spatial protein expression data, single cell gene expression data, single cell protein expression data, or any combination thereof. In some embodiments, the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some embodiments, the iterative process further comprises reviewing previous assignments of code words to barcoded target analytes, and changing the code word selected for the current barcoded target analyte to minimize the predicted density of ON signals across the series of images for barcoded target analytes to which code words have been previously assigned. In some embodiments, the iterative process is performed using a greedy algorithm, a simulated annealing algorithm, or a combination thereof. In some embodiments, the one or more code words are rank ordered according to code word weight, the one or more barcoded target analytes are rank ordered according to their corresponding single cell expression data, and the lowest ranked code word is assigned to the highest ranked barcoded target analyte. In some embodiments, two or more barcodes are assigned to a barcoded target analyte, and the method further comprises: determining a code word that corresponds to one of the two or more barcodes assigned to the barcoded target analyte based on the series of ON and OFF signals detected in the series of images; and identifying the barcoded target analyte based on the determined code word. In some embodiments, the method further comprises generating a logical OR code word that corresponds to two of the two or more barcodes assigned to the barcoded target analyte based on the series of ON and OFF signals detected at the one or more locations; and identifying the barcoded target analyte based on the logical OR code word. In some embodiments, all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

Described herein is a method for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule for assignment based on expression data for the one or more target analytes in clustered cell types, and wherein the clustered cell types represent a distribution of cell types found in the biological sample; and identifying the one or more barcoded target analytes based on the one or more determined code words. In other embodiments, the expression data for the one or more target analytes comprises bulk gene expression data, bulk protein expression data, spatial gene expression data, spatial protein expression data, single cell gene expression data, single cell protein expression data, or any combination thereof. In other embodiments, the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In other embodiments, the iterative process further comprises reviewing previous assignments of code words to barcoded target analytes, and changing the code word selected for the current barcoded target analyte to minimize the predicted density of ON signals across the series of images for barcoded target analytes to which code words have been previously assigned. In other embodiments, the iterative process is performed using a greedy algorithm, a simulated annealing algorithm, or a combination thereof. In other embodiments, the one or more code words are rank-ordered according to code word weight, the one or more barcoded target analytes are rank-ordered according to a maximum expression level across all clustered cell types, and the lowest ranked code word is assigned to the highest ranked barcoded target analyte.

Described herein is a method for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and identifying the one or more barcoded target analytes based on the one or more determined code words.

Described herein is a method for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and identifying the one or more barcoded target analytes based on the one or more determined code words, wherein two or more barcodes are assigned to a barcoded target analyte, and the method further comprises: determining a code word that corresponds to one of the two or more barcodes assigned to the barcoded target analyte based on the series of ON and OFF signals detected in the series of images; determining a logical OR code word that corresponds to two of the two or more barcodes assigned to the barcoded target analyte based on the series of ON and OFF signals detected in the series of images; and identifying the barcoded target analyte based on the logical OR code word; and identifying the barcoded target analyte based on the determined code word. In other embodiments, 3, 4, 5, 6, 7, 8, 9, 10, 11, 12, 13, 14, 15, or 16 barcodes are assigned to the barcoded target analyte.

Described herein is a method for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and identifying the one or more barcoded target analytes based on the one or more determined code words, wherein two or more barcodes are assigned to a barcoded target analyte, and the method further comprises: determining a code word that corresponds to one of the two or more barcodes assigned to the barcoded target analyte based on the series of ON and OFF signals detected in the series of images, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes; and identifying the barcoded target analyte based on the determined code word. In other embodiments, 3, 4, 5, 6, 7, 8, 9, 10, 11, 12, 13, 14, 15, or 16 barcodes are assigned to the barcoded target analyte.

Disclosed herein are methods for designing a panel of in situ detection probes comprising: generating a codebook comprising a plurality of code words, wherein each code word comprises a series of ON and OFF bits; assigning a unique code word from the codebook to each of a panel of unique target analytes, wherein the unique code words are assigned to the unique target analytes based on a minimax decision rule designed to minimize a maximum predicted density of ON signals corresponding to ON bits detected in images acquired in each cycle of a plurality of decoding cycles used to decode a corresponding panel of barcoded target analytes; and selecting a panel of in situ detection probes, wherein each in situ detection probe of the panel comprises a target recognition element and a target-specific barcode sequence that corresponds to the target-specific code word.

Disclosed herein are methods for designing a panel of in situ detection probes comprising: generating a codebook comprising a plurality of code words, wherein each code word comprises a series of ON and OFF bits; assigning a unique code word from the codebook to each of a panel of unique target analytes, wherein the unique code words are assigned to the unique target analytes based on a decision rule that ensures that a total number of ON signals corresponding to ON bits detected in an image for a given decoding cycle is within ±20% of a mean number of ON signals detected per image in images acquired in each cycle of a plurality of decoding cycles used to decode a corresponding panel of barcoded target analytes; and selecting a panel of in situ detection probes, wherein each in situ detection probe of the panel comprises a target recognition element and a target-specific barcode sequence that corresponds to the target-specific code word.

In some embodiments of any of the methods disclosed herein, the unique code words are assigned to the unique target analytes based on a decision rule that ensures that a total number of ON signals detected in an image for a given decoding cycle is within ±10% of a mean number of ON signals corresponding to ON bits detected per image in the images acquired in each cycle of a plurality of decoding cycles used to decode a corresponding panel of barcoded target analytes. In some embodiments, a majority of the bits in each of the one or more code words are OFF bits. In some embodiments, each of the one or more code words comprises a same total number of ON bits. In some embodiments, the unique code words are assigned to the unique target analytes based on a decision rule that also ensures that a total number of ON signals detected in a given image corresponds to a total number of corresponding barcoded target analytes that is within ±20% of a mean number of corresponding barcoded target analytes detected per image in the images acquired in each cycle of the plurality of decoding cycles. In some embodiments, the unique code words are assigned to the unique target analytes based on a decision rule that ensures that the total number of ON signals detected in a given image of the series of images corresponds to a total number of corresponding barcoded target analytes that is within ±10% of a mean number of corresponding barcoded target analytes detected per image in the images acquired in each cycle of the plurality of decoding cycles. In some embodiments, the decision rule for assignment of the unique code words to the unique target analytes further comprises assignment based on expression data for the panel of unique target analytes in clustered cell types, and wherein the clustered cell types represent a distribution of cell types found in a biological sample. In some embodiments, the expression data for the panel of unique target analytes comprises bulk gene expression data, bulk protein expression data, spatial gene expression data, spatial protein expression data, single cell gene expression data, single cell protein expression data, or any combination thereof. In some embodiments, the panel of unique target analytes are rank-ordered according to a maximum expression level across all clustered cell types, and the unique code words are assigned to the panel of rank-ordered target analytes using an iterative process repeated for each of the target analytes in decreasing order of maximum expression level, the iterative process comprising: computing a predicted density of ON signals corresponding to detected ON bits for every remaining, unassigned code word and the target analyte across the images acquired in each cycle of the plurality of decoding cycles and across cell types; selecting a code word from the remaining, unassigned code words that minimizes a predicted density of ON signals corresponding to detected ON bits across the images acquired in each cycle of the plurality of decoding cycles and across cell types; and assigning the selected code word to the target analyte. In some embodiments, the iterative process further comprises reviewing previous assignments of unique code words to target analytes, and changing the code word selected for a current target analyte to minimize the predicted density of ON signals corresponding to detected ON bits across the across the images acquired in each cycle of the plurality of decoding for target analytes to which code words have been previously assigned. In some embodiments, the iterative process is performed using a greedy algorithm, a simulated annealing algorithm, or a combination thereof. In some embodiments, the unique code words are rank-ordered according to code word weight, the unique target analytes are rank-ordered according to a maximum expression level across all clustered cell types, and the lowest ranked code word is assigned to the highest ranked barcoded target analyte. In some embodiments, two or more code words are assigned to a target analyte, thereby enabling identification of the target analyte by determining at least one of the two or more code words based on the series of ON and OFF signals detected in the images acquired in the plurality of decoding cycles. In some embodiments, 3, 4, 5, 6, 7, 8, 9, 10, 11, 12, 13, 14, 15, or 16 code words are assigned to the given target analyte. In some embodiments, the method further comprises assigning a logical OR code word that corresponds to two of the two or more code words assigned to the target analyte, thereby enabling identification of the target analyte by detecting the logical OR code word based on the series of ON and OFF signals detected in the images acquired in the plurality of decoding cycles. In some embodiments, all of the bits for a code word assigned to a target analyte are OFF bits, thereby ensuring that no ON signal is detected for the code word in the images acquired in the plurality of decoding cycles and reducing a sensitivity of detecting one or more target analytes. In some embodiments, synthesis of the panel of in situ detection probes comprises use of automated, solid-phase oligonucleotide synthesis. In some embodiments, selecting a panel further comprises synthesis of the panel of in situ detection probes.

Disclosed herein are panels of in situ detection probes comprising: a plurality of probes, each configured to hybridize or bind to a target analyte of a plurality of target analytes and comprising a target recognition element and a target-specific barcode sequence, wherein the target-specific barcode sequence corresponds to a target-specific code word comprising a series of ON and OFF bits that has been selected from a codebook comprising a plurality of code words and has been assigned to a target analyte of the plurality based on a minimax decision rule designed to minimize a maximum predicted density of ON signals corresponding to ON bits detected in images acquired in each cycle of a plurality of decoding cycles used to decode a corresponding plurality of barcoded target analytes.

Also disclosed herein are panels of in situ detection probes comprising: a plurality of probes, each configured to hybridize or bind to a target analyte of a plurality of target analytes and comprising a target recognition element and a target-specific barcode sequence, wherein the target-specific barcode sequence corresponds to a target-specific code word comprising a series of ON and OFF bits that has been selected from a codebook comprising a plurality of code words and has been assigned to a target analyte of the plurality based on a decision rule that ensures that a total number of ON signals corresponding to ON bits detected in an image for a given decoding cycle is within ±20% of a mean number of ON signals detected per image in images acquired in each cycle of a plurality of decoding cycles used to decode a corresponding plurality of barcoded target analytes.

Disclosed herein are systems comprising: one or more processors; and a memory communicatively coupled to the one or more processors and configured to store instructions that, when executed by the one or more processors, cause the system to: receive a series of images of a biological sample, wherein the series of images comprises images from a plurality of decoding cycles; detect, in the images of the series of images, a series of detectable signals (ON signals) or absence thereof (OFF signals) at one or more locations in the biological sample corresponding to one or more barcoded target analytes; determine, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identify the one or more barcoded target analytes based on the one or more determined code words. In some embodiments, a majority of the bits in each code word for the one or more barcoded target analytes are OFF bits. In some embodiments, each of the one or more code words comprises a same total number of ON bits. In some embodiments, the decision rule for assignment of the one or more code words to the one or more barcoded target analytes further comprises assignment based on expression data for the one or more target analytes in clustered cell types, and wherein the clustered cell types represent a distribution of cell types found in the biological sample. In some embodiments, the expression data for the one or more target analytes comprises bulk gene expression data, bulk protein expression data, spatial gene expression data, spatial protein expression data, single cell gene expression data, single cell protein expression data, or any combination thereof. In some embodiments, the instructions, when executed by the one or more processors, cause the system to rank-order the one or more code words according to code word weight, rank-order the one or more barcoded target analytes according to a maximum expression level across all clustered cell types, and assign the one or more rank-ordered code words to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some embodiments, the iterative process further comprises reviewing previous assignments of code words to barcoded target analytes, and changing the code word selected for the current barcoded target analyte to minimize the predicted density of ON signals across the series of images for barcoded target analytes to which code words have been previously assigned. In some embodiments, the iterative process is performed using a greedy algorithm, a simulated annealing algorithm, or a combination thereof. In some embodiments, two or more barcodes are assigned to a barcoded target analyte, and the instructions, when executed by the one or more processors, cause the system to: determine a code word that corresponds to one of the two or more barcodes assigned to the barcoded target analyte based on the series of ON and OFF signals detected in the series of images; and identify the barcoded target analyte based on the determined code word. In some embodiment, the instructions, when executed by the one or more processors, further cause the system to detect a logical OR code word that corresponds to two of the two or more barcodes assigned to the barcoded target analyte based on the series of ON and OFF signals detected in the series of images; and identify the barcoded target analyte based on the logical OR code word. In some embodiments, all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

Disclosed herein are non-transitory computer-readable storage media storing one or more programs, the one or more programs comprising instructions, which when executed by one or more processors of a system, cause the system to: receive a series of images of a biological sample, wherein the series of images comprises images from a plurality of decoding cycles; detect, in the images of the series of images, a series of detectable signals (ON signals) or absence thereof (OFF signals) at one or more locations in the biological sample corresponding to one or more barcoded target analytes; determine, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identify the one or more barcoded target analytes based on the one or more determined code words. In some embodiments, a majority of the bits in each code word for the one or more barcoded target analytes are OFF bits. In some embodiments, each of the one or more code words comprises a same total number of ON bits. In some embodiments, the decision rule for assignment of the one or more code words to the one or more barcoded target analytes further comprises assignment based on expression data for the one or more target analytes in clustered cell types, and wherein the clustered cell types represent a distribution of cell types found in the biological sample. In some embodiments, the expression data for the one or more target analytes comprises bulk gene expression data, bulk protein expression data, spatial gene expression data, spatial protein expression data, single cell gene expression data, single cell protein expression data, or any combination thereof. In some embodiments, the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some embodiments, the iterative process further comprises reviewing previous assignments of code words to barcoded target analytes, and changing the code word selected for the current barcoded target analyte to minimize the predicted density of ON signals across the series of images for barcoded target analytes to which code words have been previously assigned. In some embodiment, the iterative process is performed using a greedy algorithm, a simulated annealing algorithm, or a combination thereof. In some embodiments, two or more barcodes are assigned to a barcoded target analyte, and the instructions, when executed by one or more processors of a system, cause the system to: determine a code word that corresponds to one of the two or more barcodes assigned to the barcoded target analyte based on the series of ON and OFF signals detected in the series of images; and identify the barcoded target analyte based on the determined code word. In some embodiments, the instructions, when executed by one or more processors of a system, further cause the system to detect a logical OR code word that corresponds to two of the two or more barcodes assigned to the barcoded target analyte based on the series of ON and OFF signals detected in the series of images; and identify the barcoded target analyte based on the logical OR code word. In some embodiments, all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

Various aspects of the disclosed methods, devices, and systems are set forth with particularity in the appended claims. A better understanding of the features and advantages of the disclosed methods, devices, and systems will be obtained by reference to the following detailed description of illustrative embodiments and the accompanying drawings, of which:

DETAILED DESCRIPTION

Figure 1A:
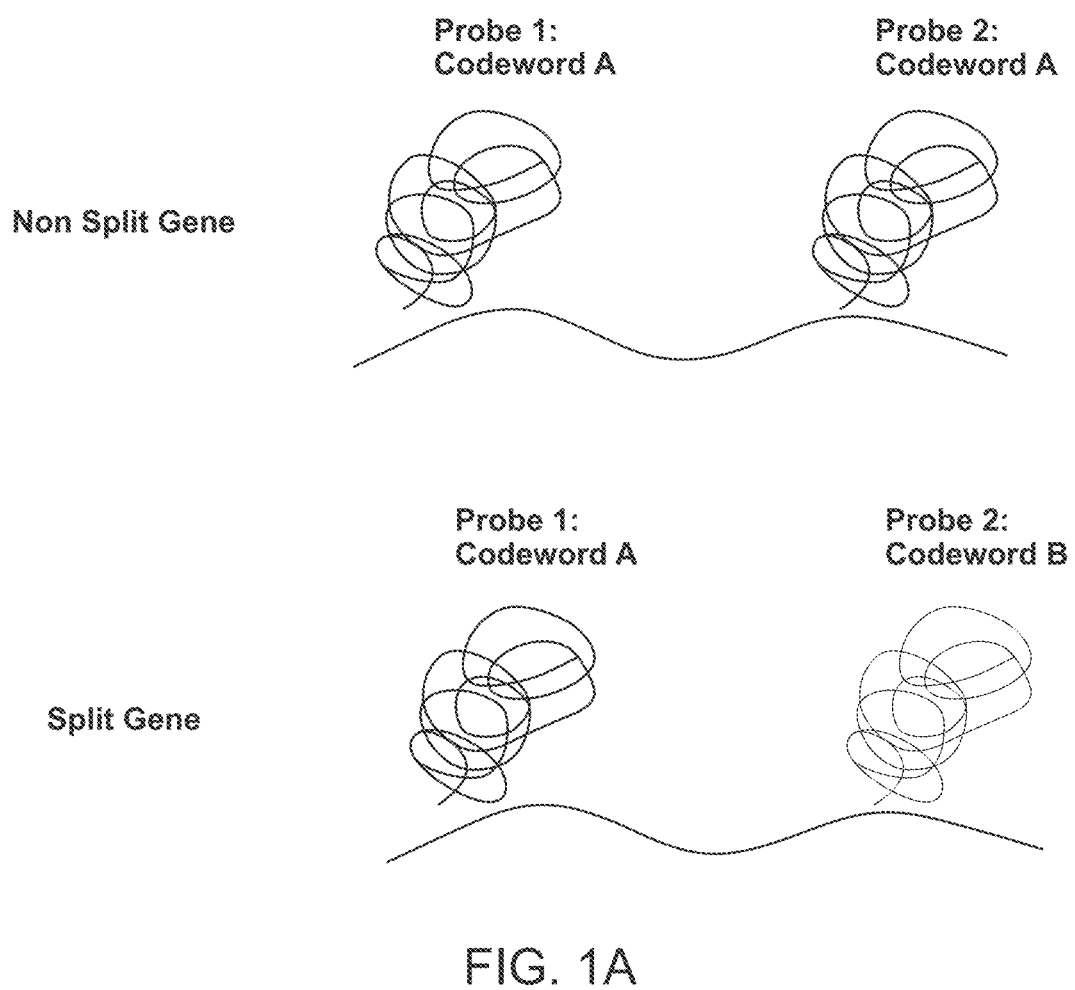
FIG. 1A provides a schematic illustration of a target probe code word splitting scenario for minimizing optical crowding.

Methods to minimize or eliminate the effects of optical crowding during detection and decoding of barcoded target analytes will be critical for implementing accurate and sensitive in situ analysis techniques. Disclosed herein are code work design strategies and methods for minimizing the impact of optical crowding on the detection and decoding of barcoded target analytes when the density of fluorescing barcoded target analytes (e.g., detectably labeled probes, fluorescing rolling circle amplification products (RCPs) of barcoded gene transcripts) approaches a threshold where it becomes difficult to resolve detectably labeled probes or individual spots (e.g., fluorescing RCPs or "ON RCPs") in the images used for decoding. Optical crowding can be minimized by minimizing the number of times each barcoded target analyte (e.g., an RCP) must be observed in the ON state during the decoding process, and designing the code words assigned to the target analytes such that the total set of ON states is distributed more-or-less evenly over the plurality of decoding cycles and detection channels used for decoding. Separate, but complementary techniques for minimizing optical crowding are described: (i) code word dilution (e.g., an approach in which the code words in a set of code words (i.e., a "code book") are designed to have the smallest possible weights (the code word weight is the total number of ON bits in a given code word; it determines how often the corresponding barcoded target analyte will be visible/detectable during the decoding process), (ii) optimized assignment of code words to target analytes (e.g., an approach in which code words are assigned to corresponding barcoded target analytes according to, e.g., single cell expression data for the target analytes in clustered cell types to reduce the weight of code words corresponding to highly expressed target analytes, where the clustered cell types represent a distribution of cell types found in the biological sample), and to avoid the co-occurrence of two abundant genes that are expressed in the same cell type appearing in the ON state in the same decoding cycle, (iii) target probe code word splitting (e.g., an approach in which two or more barcodes are assigned to a same target analyte (e.g., by incorporation into two or more anchor probes used to implement rolling circle amplification), where each barcode has a different corresponding code word assigned) and (iv) gene attenuation (e.g., instances where all of the bits for a code word corresponding to one of the two or more barcodes assigned to the barcoded target analyte are OFF bits, thereby reducing the sensitivity of detecting highly expressed target analytes).

In contrast with in situ methods such as seqFISH+ (see, e.g., Eng, et al. (2019), "Transcriptome-Scale Super-Resolved Imaging in Tissues by RNA seqFISH+", *Nature* 568 (7751):235-239) which utilize a particular structured coding approach (i.e., pseudo-colors) to achieve greater multiplexing capability, the methods described herein comprise a more general approach to binary code design and assignment to targets to minimize optical crowding by distributing ON signals over both detection channels and decoding cycles, and use codebooks comprised of codewords with multiple Hamming weights. D'Alessio, et al. (2020), "A Coding Theory Perspective on Multiplexed Molecular Profiling of Biological Tissues", International Symposium on Information Theory and Its Applications, ISITA 2020, Kapolei, HI, USA, Oct. 24-27, 2020. IEEE 2020, p. 309-313, describes a related problem of designing codes that optimize decoding specificity in the presence of highly skewed target analyte abundances, as is commonly observed for biological samples.

In some instances, the disclosed methods for performing in situ decoding comprising: receiving a series of images of a biological sample, wherein the series of images comprises images from a plurality of decoding cycles; detecting, in the images of the series of images, a series of detectable signals (ON signals) or absence thereof (OFF signals) at one or more locations in the biological sample corresponding to one or more barcoded target analytes; determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images, and over the known cell types expected to be observed in the sample; and identifying the one or more barcoded target analytes based on the one or more detected code words.

In some instances, the one or more code words may be assigned to the one or more barcoded target analytes based on expression data for the one or more target analytes in clustered cell types, and wherein the clustered cell types represent a distribution of cell types found in the biological sample. In some instances, the expression data for the one or more target analytes may comprise bulk gene expression data, bulk protein expression data, spatial gene expression data, spatial protein expression data, single cell gene expression data, single cell protein expression data, or any combination thereof.

In some instances, the one or more barcoded target analytes are rank-ordered according to a maximum expression level across all clustered cell types, and the one or more code words may be assigned to the one or more rank-ordered barcoded target analytes using an iterative process repeated for each of the one or more barcoded target analytes in decreasing order of maximum expression level, the iterative process comprising: computing a predicted density of ON signals for every remaining, unassigned code word and the barcoded target analyte across the series of images and known cell types; selecting a code word from the remaining, unassigned code words that minimizes the predicted density of ON signals across the series of images and cell types; and assigning the selected code word to the barcoded target analyte. In some instances, the iterative process may further comprise reviewing previous assignments of code words to barcoded target analytes, and changing the code word selected for the current barcoded target analyte to minimize the predicted density of ON signals across the series of images for barcoded target analytes to which code words have been previously assigned. In some instances, the iterative process may be performed using a greedy algorithm, a simulated annealing algorithm, or a combination thereof.

In some instances of the disclosed methods, two or more barcodes may be assigned to a barcoded target analyte, and the method may further comprise: detecting a code word that corresponds to one of the two or more barcodes assigned to the barcoded target analyte based on the series of ON and OFF signals detected in the series of images; and identifying the barcoded target analyte based on the code word. In some instances, the method may further comprise generating a logical OR code word that corresponds to two of the two or more barcodes assigned to the barcoded target analyte based on the series of ON and OFF signals detected at the one or more locations; and identifying the barcoded target analyte based on the logical OR code word. In some instances, all of the bits for a code word corresponding to at least one of the two or more barcodes assigned to the barcoded target analyte may be OFF bits, thereby ensuring that no signal is detected for the code word in the series of images and reducing a sensitivity of detecting one or more barcoded target analytes.

General Terminology

Specific terminology is used throughout this disclosure to explain various aspects of the methods, systems, and compositions that are described. Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. For example, "a" or "an" means "at least one" or "one or more". Any reference to "or" herein is intended to encompass "and/or" unless otherwise stated.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, un-recited additives, components, integers, elements or method steps.

As used herein, the term "about" a number refers to that number plus or minus 10% of that number. The term 'about' when used in the context of a range refers to that range minus 10% of its lowest value and plus 10% of its greatest value.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The term "platform" (or "system") may refer to an ensemble of: (i) instruments (e.g., imaging instruments, fluid controllers, temperature controllers, motion controllers and translation stages, etc.), (ii) devices (e.g., specimen slides, substrates, flow cells, microfluidic devices, etc., which may comprise fixed and/or removable or disposable components of the platform), (iii) reagents and/or reagent kits, and (iv) software, or any combination thereof, which allows a user to perform one or more bioassay methods (e.g., analyte detection, in situ detection or sequencing, and/or nucleic acid detection or sequencing) depending on the particular combination of instruments, devices, reagents, reagent kits, and/or software utilized.

The section headings used herein are for organizational purposes only and are not to be construed as limiting the subject matter described.

Barcoding and Decoding Terminology

A "barcode" is a label, or identifier, that conveys or is capable of conveying information (e.g., information about an analyte in a sample, a cell, a bead, a location, a sample, and/or a capture probe). The term "barcode" may refer either to a physical barcode molecule (e.g., a nucleic acid barcode molecule) or to its representation in a computer-readable, digital format (e.g., as a string of characters representing the sequence of bases in a nucleic acid barcode molecule).

The phrase "barcode diversity" refers to the total number of unique barcode sequences that may be represented by a given set of barcodes.

A physical barcode molecule (e.g., a nucleic acid barcode molecule) that forms a label or identifier as described above. In some instances, a barcode can be part of an analyte, can be independent of an analyte, can be attached to an analyte, or can be attached to or part of a probe that targets the analyte. In some instances, a particular barcode can be unique relative to other barcodes.

Physical barcodes can have a variety of different formats. For example, barcodes can include polynucleotide barcodes, random nucleic acid and/or amino acid sequences, and synthetic nucleic acid and/or amino acid sequences. A physical barcode can be attached to an analyte, or to another moiety or structure, in a reversible or irreversible manner. A physical barcode can be added to, for example, a fragment of a deoxyribonucleic acid (DNA) or ribonucleic acid (RNA) sample before or during sequencing of the sample. In some instances, barcodes can allow for identification and/or quantification of individual sequencing-reads in sequencing-based methods (e.g., a barcode can be or can include a unique molecular identifier or "UMI"). Barcodes can be used to detect and spatially-resolve molecular components found in biological samples, for example, at single-cell resolution (e.g., a barcode can be, or can include, a molecular barcode, a spatial barcode, a unique molecular identifier (UMI), etc.).

In some instances, barcodes may comprise a series of two or more segments or sub-barcodes (e.g., corresponding to "letters" or "code words" in a decoded barcode), each of which may comprise one or more of the subunits or building blocks used to synthesize the physical (e.g., nucleic acid) barcode molecules. For example, a nucleic acid barcode molecule may comprise two or more barcode segments, each of which comprises one or more nucleotides. In some instances, a barcode may comprise at least 1, 2, 3, 4, 5, 6, 7, 8, 9, 10, or more than 10 segments. In some instances, each segment of a barcode molecule may comprise at least 1, 2, 3, 4, 5, 6, 7, 8, 9, 10, 12, 14, 16, 18, 20, or more than 20 subunits or building blocks. For example, each segment of a nucleic acid barcode molecule may comprise at least 1, 2, 3, 4, 5, 6, 7, 8, 9, 10, 12, 14, 16, 18, 20, or more than 20 nucleotides. In some instances, two or more of the segments of a barcode may be separated by non-barcode segments, i.e., the segments of a barcode molecule need not be contiguous.

A "digital barcode" (or "digital barcode sequence") is a representation of a corresponding physical barcode (or target analyte sequence) in a computer-readable, digital format as described above. A digital barcode may comprise one or more "letters" (e.g., 1, 2, 3, 4, 5, 6, 7, 8, 9, 10, 12, 14, 16, 18, 20, or more than 20 letters) or one or more "code words" (e.g., 1, 2, 3, 4, 5, 6, 7, 8, 9, 10, or more than 10 code words), where a "code word" comprises, e.g., 1, 2, 3, 4, 5, 6, 7, 8, 9, 10, 12, 14, 16, 18, 20, or more than 20 letters. In some instances, the sequence of letters or code words in a digital barcode sequence may correspond directly with the sequence of building blocks (e.g., nucleotides) in a physical barcode. In some instances, the sequence of letters or code words in a digital barcode sequence may not correspond directly with the sequence of building blocks in a physical barcode, but rather may comprise, e.g., arbitrary code words that each correspond to a segment of a physical barcode. For example, in some instances, the disclosed methods for decoding and error correction may be applied directly to detecting target analyte sequences (e.g., mRNA sequences) as opposed to detecting target barcodes, and the barcode probes used to detect the target analyte sequences may correspond to letters or code words that have been assigned to specific target analyte sequences but that do not directly correspond to the target analyte sequences.

A "designed barcode" (or "designed barcode sequence") is a barcode (or its digital equivalent; in some instances a designed barcode may comprise a series of code words that can be assigned to gene transcripts and subsequently decoded into a decoded barcode) that meets a specified set of design criteria as required for a specific application. In some instances, a set of designed barcodes may comprise at least 2, at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2 \times 10^6$, at least $3 \times 10^6$, at least $4 \times 10^6$, at least $5 \times 10^6$, at least $6 \times 10^6$, at least $7 \times 10^6$, at least $8 \times 10^6$, at least $9 \times 10^6$, at least $10^7$, at least $10^8$, at least $10^9$, or more than $10^9$ unique barcodes. In some instances, a set of designed barcodes may comprise any number of designed barcodes within the range of values in this paragraph, e.g., 1,225 unique barcodes or $2.38 \times 10^6$ unique barcodes. As noted above for barcodes in general, in some instances designed barcodes may comprise two or more segments (corresponding to two or more code words in a decode barcode). In those cases, the specified set of design criteria may be applied to the designed barcodes as a whole, or to one or more segments (or positions) within the designed barcodes.

A "decoded barcode" (or "decoded barcode sequence") is a digital barcode sequence generated via a decoding process that ideally matches a designed barcode sequence, but that may include errors arising from noise in the synthesis process used to create barcodes and/or noise in the decoding process itself. As noted above, in some instances, the disclosed methods for decoding and error correction may be applied directly to detecting target analytes (e.g., mRNA sequences) as opposed to detecting target barcodes, and the barcode probes used to detect the target analytes may correspond to letters or code words that have been assigned to specific target analytes but that do not directly correspond to the target analytes. In these instances, a decoded barcode (i.e., a series of letters or code words) may serve as a proxy for the target analyte.

A "corrected barcode" (or "corrected barcode sequence") is a digital barcode sequence derived from a decoded barcode sequence by applying one or more error correction methods.

Probe Terminology

The term "probe" may refer either to a physical probe molecule (e.g., a nucleic acid probe molecule) or to its representation in a computer-readable, digital format (e.g., as a string of characters representing the sequence of bases in a nucleic acid probe molecule). A "probe" may be, for example, a molecule designed to recognize (and bind or hybridize to) another molecule, e.g., a target analyte, another probe molecule, etc.

In some instances, a physical probe molecule may comprise one or more of the following: (i) a target recognition element (e.g., an antibody capable of recognizing and binding to a target peptide, protein, or small molecule; an oligonucleotide sequence that is complementary to a target gene sequence or gene transcript; or a poly-T oligonucleotide sequence that is complementary to the poly-A tails on messenger RNA molecules), (ii) a barcode element (e.g., a molecular barcode, a cell barcode, a spatial barcode, and/or a unique molecular identifier (UMI)), (iii) an amplification and/or sequencing primer binding site, (iv) one or more linker regions, (v) one or more detectable tags (e.g., fluorophores), or any combination thereof. In some instances, each component of a probe molecule may comprise at least 1, 2, 3, 4, 5, 6, 7, 8, 9, 10, 12, 14, 16, 18, 20, or more than 20 subunits or building blocks. For example, in some instances, each component of a nucleic acid probe molecule may comprise at least 1, 2, 3, 4, 5, 6, 7, 8, 9, 10, 12, 14, 16, 18, 20, or more than 20 nucleotides.

In some instances, physical probes may bind or hybridize directly to their target. In some instances, physical probes may bind or hybridize indirectly to their target. For example, in some instances, a secondary probe may bind or hybridize to a primary probe, where the primary probe binds or hybridizes directly to the target analyte. In some instances, a tertiary probe may bind or hybridize to a secondary probe, where the secondary probe binds or hybridizes to a primary probe, and where the primary probe binds or hybridizes directly to the target analyte.

Examples of "probes" and their applications include, but are not limited to, primary probes (e.g., molecules designed to recognize and bind or hybridize to target analyte), intermediate probes (e.g., molecules designed to recognize and bind or hybridize to another molecule and provide a hybridization or binding site for another probe (e.g., a detection probe), detection probes (e.g., molecules designed to recognize and bind or hybridize to another molecule, detection probes may be labeled with a fluorophore or other detectable tag). In some instances, a probe may be designed to recognize and bind (or hybridize) to a physical barcode sequence (or segments thereof). In some instances, a probe may be used to detect and decode a barcode, e.g., a nucleic acid barcode. In some instances, a probe may bind or hybridize directly to a target barcode. In some instances, a probe may bind or hybridize indirectly to a target barcode (e.g., by binding or hybridizing to other probe molecules which itself is bound or hybridized to the target barcode).

Nucleic Acid Molecule and Nucleotide Terminology

The terms "nucleic acid" (or "nucleic acid molecule") and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include natural or non-natural nucleotides. In this regard, a naturally-occurring deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-natural bases that can be included in a nucleic acid or nucleotide are known in the art. See, for example, Appella (2009), "Non-Natural Nucleic Acids for Synthetic Biology", *Curr Opin Chem Biol.* 13(5-6): 687-696; and Duffy, et al. (2020), "Modified Nucleic Acids: Replication, Evolution, and Next-Generation Therapeutics", *BMC Biology* 18:112.

Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some instances, the biological sample may comprise cells which are deposited on a surface.

Cell-free biological samples can include extracellular macromolecules, e.g., polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

In some instances, a substrate herein can be any support that is insoluble in aqueous liquid and which allows for positioning of biological samples, analytes, features, and/or reagents (e.g., probes) on the support. In some instances, a biological sample can be attached to a substrate. Attachment of the biological sample can be irreversible or reversible, depending upon the nature of the sample and subsequent steps in the analytical method. In certain instances, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. In some instances, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

Endogenous Analytes:

In some instances, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some instances, the analyte is inside a cell or on a cell surface, such as a transmembrane analyte or one that is attached to the cell membrane. In some instances, the analyte can be an organelle (e.g., nuclei or mitochondria). In some instances, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, lRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some instances described herein, an analyte may be a denatured nucleic acid, wherein the resulting denatured nucleic acid is single-stranded. The nucleic acid may be denatured, for example, optionally using formamide, heat, or both formamide and heat. In some instances, the nucleic acid is not denatured for use in a method disclosed herein.

In certain instances, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any implementation described herein, the analyte comprises a target sequence. In some instances, the target sequence may be endogenous to the sample, generated in the sample, added to the sample, or associated with an analyte in the sample. In some instances, the target sequence is a single-stranded target sequence (e.g., a sequence in a rolling circle amplification product). In some instances, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some instances, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

Labelling Agents:

In some instances, provided herein are methods and compositions for analyzing endogenous analytes (e.g., RNA, ssDNA, and cell surface or intracellular proteins and/or metabolites) in a sample using one or more labelling agents. In some instances, an analyte labelling agent may include an agent that interacts with an analyte (e.g., an endogenous analyte in a sample). In some instances, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some instances, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some instances, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some instances, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some instances, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some instances, an analyte binding moiety includes one or more antibodies or antigen binding fragments thereof. The antibodies or antigen binding fragments including the analyte binding moiety can specifically bind to a target analyte. In some instances, the analyte is a protein (e.g., a protein on a surface of the biological sample (e.g., a cell) or an intracellular protein). In some instances, a plurality of analyte labelling agents comprising a plurality of analyte binding moieties bind a plurality of analytes present in a biological sample. In some instances, the plurality of analytes includes a single species of analyte (e.g., a single species of polypeptide). In some instances in which the plurality of analytes includes a single species of analyte, the analyte binding moieties of the plurality of analyte labelling agents are the same. In some instances in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some instances, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some instances, the reporter oligonucleotides are releasable from the labelling agent, such as upon application of a stimulus. For example, the reporter oligonucleotide may be attached to the labelling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer binding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some instances, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

Assays for In Situ Detection and Analysis:

Objectives for in situ detection and analysis methods include detecting, quantifying, and/or mapping analytes (e.g., gene activity) to specific regions in a biological sample (e.g., a tissue sample or cells deposited on a surface) at cellular or sub-cellular resolution. Methods for performing in situ studies include a variety of techniques, e.g., in situ hybridization and in situ sequencing techniques. These techniques allow one to study the subcellular distribution of target analytes (e.g., gene activity as evidenced, e.g., by expressed gene transcripts), and have the potential to provide crucial insights in the fields of developmental biology, oncology, immunology, histology, etc.

Various methods can be used for in situ detection and analysis of target analytes, e.g., sequencing by synthesis (SBS), sequencing by ligation (SBL), sequencing by hybridization (SBH). Non-limiting examples of in situ hybridization techniques include single molecule fluorescence in situ hybridization (smFISH) and multiplexed error-robust fluorescence in situ hybridization (MERFISH). smFISH enables in situ detection and quantification of gene transcripts in tissue samples at the locations where they reside by making use of libraries of multiple short oligonucleotide probes (e.g., approximately 20 base pairs (bp) in length), each labeled with a fluorophore. The probes are sequentially hybridized to gene sequences (e.g., DNA) or gene transcript sequences (e.g., mRNA) sequences, and visualized as diffraction-limited spots by fluorescence microscopy (Levsky, et al. (2003) "Fluorescence In situ Hybridization: Past, Present and Future", Journal of Cell Science 116(14):2833-2838; Raj, et al. (2008) "Imaging Individual mRNA Molecules Using Multiple Singly Labeled Probes", Nat Methods 5(10): 877-879; Moor, et al. (2016), ibid.). Variations on the smFISH method include, for example, the use of combinatorial labelling schemes to improve multiplexing capability (Levsky, et al. (2003), ibid.), the use of smFISH in combination with super-resolution microscopy (Lubeck, et al. (2014) "Single-Cell In situ RNA Profiling by Sequential Hybridization", Nature Methods 11(4):360-361).

MERFISH addresses two of the limitations of earlier in situ hybridization approaches, namely the limited number of target sequences that could be simultaneously identified and the robustness of the approach to readout errors caused by the stochastic nature of the hybridization process (Moor, et al. (2016), ibid.). MERFISH utilizes a binary barcoding scheme in which the probed target mRNA sequences are either fluorescence positive or fluorescence negative for any given imaging cycle (Ke, et al. (2016), ibid.; Moffitt, et al. (2016) "RNA Imaging with Multiplexed Error Robust Fluorescence In situ Hybridization", *Methods Enzymol.* 572:1-49). The encoding probes that contain a combination of target-specific hybridization sequence regions and barcoded readout sequence regions are first hybridized to the target mRNA sequences. In each imaging cycle, a subset of fluorophore-conjugated readout probes is hybridized to a subset of encoding probes. Target mRNA sequences that fluoresce in a given cycle are assigned a value of "1" and the remaining target mRNA sequences are assigned a value of "0". Between imaging cycles, the fluorescent probes from the previous cycle are photobleached. After, e.g., 14 or 16 rounds of readout probe hybridization and imaging, unique combinations of the detected fluorescence signals generate a 14-bit or 16-bit code that identifies the different gene transcripts. To address the increased error rate for correctly calling the readout codes increases as the number of hybridization and imaging cycles increases, the method may also entail the use of Hamming distances for barcode design and correction of decoding errors (see, e.g., Buschmann, et al. (2013) "Levenshtein Error-Correcting Barcodes for Multiplexed DNA Sequencing", *Bioinformatics* 14:272), thereby resulting in an error-robust barcoding scheme.

Some in situ sequencing techniques generally comprise both in situ target capture (e.g., of mRNA sequences) and in situ sequencing. Non-limiting examples of in situ sequencing techniques include in situ sequencing with padlock probes (ISS-PLP), fluorescent in situ sequencing (FISSEQ), barcode in situ targeted sequencing (Barista-Seq), and spatially-resolved transcript amplicon readout mapping (STARmap) (see, e.g., Ke, et al. (2016), ibid., Asp, et al. (2020), ibid.).

Some methods for in situ detection and analysis of analytes utilize a probe (e.g., padlock or circular probe) that detects specific target analytes. The in situ sequencing using padlock probes (ISS-PLP) method, for example, combines padlock probing to target specific gene transcripts, rolling-circle amplification (RCA), and sequencing by ligation (SBL) chemistry. Within intact tissue sections, reverse transcription primers are hybridized to target sequence (e.g., mRNA sequences) and reverse transcription is performed to create cDNA to which a padlock probe (a single-stranded DNA molecule comprising regions that are complementary to the target cDNA) can bind (see, e.g., Asp, et al. (2020), ibid.). In one variation of the method, the padlock probe binds to the cDNA target with a gap remaining between the ends which is then filled in using a DNA polymerization reaction. In another variation of the method, the ends of the bound padlock probe are adjacent to each other. The ends are then ligated to create a circular DNA molecule. Target amplification using rolling-circle amplification (RCA) results in micrometer-sized RCA products (RCPs), containing a plurality of concatenated repeats of the probe sequence. In some examples, RCPs are then subjected to, e.g., sequencing-by-ligation (SBL) or sequencing-by-hybridization (SBH). In some cases, the method allows for a barcode located within the probe to be decoded.

Products of Endogenous Analytes and/or Labelling Agents:

In some instances, provided herein are methods and compositions for analyzing one or more products of an endogenous analyte and/or a labelling agent in a biological sample. In some instances, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some instances, a labelling agent that directly or indirectly binds to an analyte in the biological sample is analyzed. In some instances, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

In some instances, the analyzing comprises using primary probes which comprise a target binding region (e.g., a region that binds to a target such as RNA transcripts) and the primary probes may contain one or more barcodes (e.g., primary barcode). In some instances, the barcodes are bound by detection primary probes, which do not need to be fluorescent, but that include a target-binding portion (e.g., for hybridizing to one or more primary probes) and one or more barcodes (e.g., secondary barcodes). In some instances, the detection primary probe comprises an overhang that does not hybridize to the target nucleic acid but hybridizes to another probe. In some examples, the overhang comprises the barcode(s). In some instances, the barcodes of the detection primary probes are targeted by detectably labeled detection oligonucleotides, such as fluorescently labeled oligos. In some instances, one or more decoding schemes are used to decode the signals, such as fluorescence, for sequence determination. Various probes and probe sets can be used to hybridize to and detect an endogenous analyte and/or a sequence associated with a labelling agent. In some instances, these assays may enable multiplexed detection, signal amplification, combinatorial decoding, and error correction schemes. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set. The specific probe or probe set design can vary.

Hybridization and Ligation:

Various probes and probe sets can be hybridized to an endogenous analyte and/or a labelling agent and each probe may comprise one or more barcode sequences. The specific probe or probe set design can vary. In some instances, the hybridization of a primary probe or probe set (e.g., a circularizable probe or probe set) to a target nucleic acid analyte and may lead to the generation of a rolling circle amplification (RCA) template. In some instances, the assay uses or generates a circular nucleic acid molecule which can be the RCA template.

In some instances, a product of an endogenous analyte and/or a labelling agent is a ligation product. In some instances, the ligation product is formed from circularization of a circularizable probe or probe set upon hybridization to a target sequence. In some instances, the ligation product is formed between two or more endogenous analytes. In some instances, the ligation product is formed between an endogenous analyte and a labelling agent. In some instances, the ligation product is formed between two or more labelling agent. In some instances, the ligation product is an intramolecular ligation of an endogenous analyte. In some instances, the ligation product is an intramolecular ligation of a labelling agent, for example, the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some instances, provided herein is a probe or probe set capable of DNA-templated ligation, such as from a cDNA molecule. Sec, e.g., U.S. Pat. No. 8,551,710, which is hereby incorporated by reference in its entirety. In some instances, provided herein is a probe or probe set capable of RNA-templated ligation. See, e.g., U.S. Pat. Pub. 2020/0224244 which is hereby incorporated by reference in its entirety. In some instances, the probe set is a SNAIL probe set. See, e.g., U.S. Pat. Pub. 20190055594, which is hereby incorporated by reference in its entirety. In some instances, provided herein is a multiplexed proximity ligation assay. Sec, e.g., U.S. Pat. Pub. 20140194311 which is hereby incorporated by reference in its entirety. In some instances, provided herein is a probe or probe set capable of proximity ligation, for instance a proximity ligation assay for RNA (e.g., PLAYR) probe set. Sec, e.g., U.S. Pat. Pub. 20160108458, which is hereby incorporated by reference in its entirety. In some instances, a circular probe can be indirectly hybridized to the target nucleic acid. In some instances, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some instances, the ligation involves chemical ligation. In some instances, the ligation involves template dependent ligation. In some instances, the ligation involves template independent ligation. In some instances, the ligation involves enzymatic ligation.

In some instances, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some instances, the ligase is a T4 RNA ligase. In some instances, the ligase is a splintR ligase. In some instances, the ligase is a single stranded DNA ligase. In some instances, the ligase is a T4 DNA ligase. In some instances, the ligase is a ligase that has an DNA-splinted DNA ligase activity. In some instances, the ligase is a ligase that has an RNA-splinted DNA ligase activity.

In some instances, the ligation herein is a direct ligation. In some instances, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some instances, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo) nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific implementations, the gap may be a gap of about 1, 2, 3, 4, 5, 6, 7, 8, 9 or 10 or more nucleotides, of any integer (or range of integers) of nucleotides in between the indicated values. In some instances, the gap between said terminal regions may be filled by a gap oligonucleotide or by extending the 3' end of a polynucleotide. In some cases, ligation involves ligating the ends of the probe to at least one gap (oligo) nucleotide, such that the gap (oligo) nucleotide becomes incorporated into the resulting polynucleotide. In some instances, the ligation herein is preceded by gap filling. In other implementations, the ligation herein does not require gap filling.

In some instances, ligation of the polynucleotides produces polynucleotides with melting temperature higher than that of un-ligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower Tm around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some instances, the ligation herein is a proximity ligation of ligating two (or more) nucleic acid sequences that are in proximity with each other, e.g., through enzymatic means (e.g., a ligase). In some instances, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

Primer Extension and Amplification:

In some instances, the hybridization of a primary probe or probe set (e.g. a circularizable probe or probe set) to a target analyte and may lead to the generation of an extension or amplification product. In some instances, a product is a primer extension product of an analyte, a labelling agent, a probe or probe set bound to the analyte (e.g., a circularizable probe bound to genomic DNA, mRNA, or cDNA), or a probe or probe set bound to the labelling agent (e.g., a circularizable probe bound to one or more reporter oligonucleotides from the same or different labelling agents.

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some instances, a product of an endogenous analyte and/or a labelling agent is an amplification product of one or more polynucleotides, for instance, a circular probe or circularizable probe or probe set. In some instances, the disclosed methods may comprise the use of a rolling circle amplification (RCA) technique to amplify signal. Rolling circle amplification is an isothermal, DNA polymerase-mediated process in which long single-stranded DNA molecules are synthesized on a short circular single-stranded DNA template using a single DNA primer (Zhao, et al. (2008), "Rolling Circle Amplification: Applications in Nanotechnology and Biodetection with Functional Nucleic Acids", *Angew Chem Int Ed Engl.* 47(34):6330-6337; Ali, et al. (2014), "Rolling Circle Amplification: A Versatile Tool for Chemical Biology, Materials Science and Medicine", *Chem Soc Rev.* 43(10):3324-3341). The RCA product is a concatemer containing tens to hundreds of tandem repeats that are complementary to the circular template, and may be used to develop sensitive techniques for the detection of a variety of targets, including nucleic acids (DNA, RNA), small molecules, proteins, and cells (Ali, et al. (2014), ibid.). In some implementations, a primer that hybridizes to the circular probe or circularized probe is added and used as such for amplification. In some instances, the RCA comprises a linear RCA, a branched RCA, a dendritic RCA, or any combination thereof.

In some instances, the amplification is performed at a temperature between or between about 20° C. and about 60° C. In some instances, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some instances, upon addition of a DNA polymerase in the presence of appropriate dNTP precursors and other cofactors, a primer is elongated to produce multiple copies of the circular template. This amplification step can utilize isothermal amplification or non-isothermal amplification. In some instances, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11):2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29: el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some instances, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some instances, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some instances, the RCA template may comprise the target analyte, or a part thereof, where the target analyte is a nucleic acid, or it may be provided or generated as a proxy, or a marker, for the analyte. In some instances, the RCA template may comprise a sequence of the probes and probe sets hybridized to an endogenous analyte and/or a labelling agent. In some instances, the amplification product can be generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some instances, an assay may detect a product herein that includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein (e.g., a bridge probe or L-probe) may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe (e.g., a detection probe). The exogenously added nucleic acid probe may be optionally ligated to a cellular nucleic acid molecule or another exogenous nucleic acid molecule. In other examples, a product comprising a target sequence for a probe disclosed herein (e.g., an anchor probe) may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for a probe disclosed herein (e.g., a bridge probe or L-probe) may be a probe hybridizing to an RCP. The probe may comprise an overhang that does not hybridize to the RCP but hybridizes to another probe (e.g., a detection probe).

Signal Amplification Methods:

In some instances, a method disclosed herein may also comprise one or more signal amplification components and detecting such signals. In some instances, the present disclosure relates to the detection of nucleic acid sequences in situ using probe hybridization and generation of amplified signals associated with the probes. In some instances, the target nucleic acid of a nucleic acid probe comprises multiple target sequences for nucleic acid probe hybridization, such that the signal corresponding to a barcode sequence of the nucleic acid probe is amplified by the presence of multiple nucleic acid probes hybridized to the target nucleic acid. For example, multiple sequences can be selected from a target nucleic acid such as an mRNA, such that a group of nucleic acid probes (e.g., 20-50 nucleic acid probes) hybridize to the mRNA in a tiled fashion. In another example, the target nucleic acid can be an amplification product (e.g., an RCA product) comprising multiple copies of a target sequence (e.g., a barcode sequence of the RCA product).

Alternatively or additionally, amplification of a signal associated with a barcode sequence of a nucleic acid probe can be amplified using one or more signal amplification strategies off of an oligonucleotide probe that hybridizes to the barcode sequence. In some aspects, amplification of the signal associated with the oligonucleotide probe can reduce the number of nucleic acid probes needed to hybridize to the target nucleic acid to obtain a sufficient signal-to-noise ratio. For example, the number of nucleic acid probes to tile a target nucleic acid such as an mRNA can be reduced. In some aspects, reducing the number of nucleic acid probes tiling a target nucleic acid enables detection of shorter target nucleic acids, such as shorter mRNAs. In some instances, no more than one, two, three, 4, 5, 6, 7, 8, 9, 10, 11, 12, 13, 14, 15, 16, 17, 18. 19, or 20 nucleic acid probes may be hybridized to the target nucleic acid. In instances wherein the target nucleic acid is an amplification product, signal amplification off of the oligonucleotide probes may reduce the number of target sequences required for detection (e.g., the length of the RCA product can be reduced).

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some instances, a non-enzymatic signal amplification method may be used.

The detectable reactive molecules may comprise tyramide, such as used in tyramide signal amplification (TSA) or multiplexed catalyzed reporter deposition (CARD)-FISH. In some instances, the detectable reactive molecule may be releasable and/or cleavable from a detectable label such as a fluorophore. In some instances, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, WO 2019/236841, WO 2020/102094, WO 2020/163397, and WO 2021/067475, all of which are incorporated herein by reference in their entireties.

In some instances, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101(43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator"

nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another and thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., WO 2020/123742 incorporated herein by reference), and may be used in the methods herein.

In some instances, similar to HCR reactions that use hairpin monomers, linear oligo hybridization chain reaction (LO-HCR) can also be used for signal amplification. In some instances, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some instances, the first species and/or the second species may not comprise a hairpin structure. In some instances, the plurality of LO-HCR monomers may not comprise a metastable secondary structure. In some instances, the LO-HCR polymer may not comprise a branched structure. In some instances, performing the linear oligo hybridization chain reaction comprises contacting the target nucleic acid molecule with the initiator to provide the initiator hybridized to the target nucleic acid molecule. In any of the instances herein, the target nucleic acid molecule and/or the analyte can be an RCA product.

In some instances, detection of nucleic acids sequences in situ includes combination of the sequential decoding methods described herein with an assembly for branched signal amplification. In some instances, the assembly complex comprises an amplifier hybridized directly or indirectly (via one or more oligonucleotides) to a sequence of an oligonucleotide probe described herein. In some instances, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some instances, the amplifier repeating sequence is about 5-30 nucleotides, and is repeated N times in the amplifier. In some instances, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some instances, an oligonucleotide probe described herein can be associated with an amplified signal by a method that comprises signal amplification by performing a primer exchange reaction (PER). In various instances, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various instances, the strand displacing polymerase is Bst. In various instances, the catalytic hairpin includes a stopper which releases the strand displacing polymerase. In various instances, branch migration displaces the extended primer, which can then dissociate. In various instances, the primer undergoes repeated cycles to form a concatemer primer (see e.g., U.S. Pat. Pub. No. US20190106733, which is incorporated herein by reference, for exemplary molecules and PER reaction components).

Barcoded Analytes and Detection:

A target sequence for a probe disclosed herein may be comprised in any analyte disclose herein, including an endogenous analyte (e.g., a viral or cellular nucleic acid), a labelling agent, or a product generated in the biological sample using an endogenous analyte and/or a labelling agent.

In some aspects, one or more of the target sequences includes or is associated with one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some instances, a barcode includes two or more sub-barcodes that together function as a single barcode. For example, a polynucleotide barcode can include two or more polynucleotide sequences (e.g., sub-barcodes) that are separated by one or more non-barcode sequences. In some instances, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding implementations, barcodes (e.g., primary and/or secondary barcode sequences) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the barcodes by sequential hybridization and detection with a plurality of labelled probes (e.g., detection probes (e.g., detection oligos) or barcode probes). In some instances, the barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte can be detected as performed in sequential fluorescent in situ hybridization (seqFISH).

In some instances, in a barcode-based detection method, barcode sequences are detected for identification of other molecules including nucleic acid molecules (DNA or RNA) longer than the barcode sequences themselves, as opposed to direct sequencing of the longer nucleic acid molecules. In some instances, a N-mer barcode sequence comprises 4N complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some instances, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

Sequential Hybridization:

In some instances, the present disclosure relates to methods and compositions for encoding and detecting analytes in a temporally sequential manner for in situ analysis of an analyte in a biological sample, e.g., a target nucleic acid in a cell in an intact tissue. In some aspects, provided herein is a method for detecting the detectably-labeled probes, thereby generating a signal signature. In some instances, the signal signature corresponds to an analyte of the plurality of analytes. In some instances, the methods described herein are based, in part, on the development of a multiplexed biological assay and readout, in which a sample is first contacted with a plurality of nucleic acid probes comprising one or more probe types (e.g., labelling agent, circularizable probe, circular probe, etc.), allowing the probes to directly or indirectly bind target analytes, which may then be optically detected (e.g., by detectably-labeled probes) in a temporally-sequential manner. In some instances, the probes or probe sets comprising various probe types may be applied to a sample simultaneously. In some instances, the probes or probe sets comprising various probe types may be applied to a sample sequentially. In some aspects, the method comprises sequential hybridization of labelled probes to create a spatiotemporal signal signature or code that identifies the analyte.

In some aspects, provided herein is a method involving a multiplexed biological assay and readout, in which a sample is first contacted with a plurality of nucleic acid probes, allowing the probes to directly or indirectly bind target analytes, which may then be optically detected (e.g., by detectably-labeled probes) in a temporally sequential manner. The plurality of nucleic acid probes themselves may be detectably-labeled and detected; in other words, the nucleic acid probes themselves serve as the detection probes. In other implementations, a nucleic acid probe itself is not directly detectably-labeled (e.g., the probe itself is not conjugated to a detectable label); rather, in addition to a target binding sequence (e.g., a sequence binding to a barcode sequence in an RCA product), the nucleic acid probe further comprises a sequence for detection which can be recognized by one or more detectably-labeled detection probes. In some instances, the probes or probe sets comprising various probe types may be applied to a sample simultaneously. In some instances, the probes or probe sets comprising various probe types may be applied to a sample sequentially. In some instances, the method comprises detecting a plurality of analytes in a sample.

In some instances, the method presented herein comprises contacting the sample with a plurality of probes comprising one or more probes having distinct labels and detecting signals from the plurality of probes in a temporally sequential manner, wherein said detection generates signal signatures each comprising a temporal order of signal or absence thereof, and the signal signatures correspond to said plurality of probes that identify the corresponding analytes. In some instances, the temporal order of the signals or absence thereof corresponding to the analytes can be unique for each different analyte of interest in the sample. In some instances, the plurality of probes hybridize to an endogenous molecule in the sample, such as a cellular nucleic acid molecule, e.g., genomic DNA, RNA (e.g., mRNA), or cDNA. In some instances, the plurality of probes hybridize to a product of an endogenous molecule in the sample (e.g., directly or indirectly via an intermediate probe). In some instances, the plurality of probes hybridize to labelling agent that binds directly or indirectly to an endogenous molecule in the sample or a product thereof. In some instances, the plurality of probes hybridize to a product (e.g., an RCA product) of a labelling agent that binds directly or indirectly to an endogenous molecule in the sample or a product thereof.

In any of the implementations disclosed herein, the detection of signals can be performed sequentially in cycles, one for each distinct label. In any of the implementations disclosed herein, signals or absence thereof from detectably-labeled probes targeting an analyte in a particular location in the sample can be recorded in a first cycle for detecting a first label, and signals or absence thereof from detectably-labeled probes targeting the analyte in the particular location can be recorded in a second cycle for detecting a second label distinct from the first label. In any of the implementations disclosed herein, a unique signal signature can be generated for each analyte of the plurality of analytes. In any of the implementations disclosed herein, one or more molecules comprising the same analyte or a portion thereof can be associated with the same signal signature.

In some instances, the in situ assays employ strategies for optically encoding the spatial location of target analytes (e.g., mRNAs) in a sample using sequential rounds of fluorescent hybridization. Microcopy may be used to analyze 4 or 5 fluorescent colors indicative of the spatial localization of a target, followed by various rounds of hybridization and stripping, in order to generate a large set of unique optical signal signatures assigned to different analytes. These methods often require a large number of hybridization rounds, and a large number of microscope lasers (e.g., detection channels) to detect a large number of fluorophores, resulting in a one to one mapping of the lasers to the fluorophores. Specifically, each detectably-labeled probe comprises one detectable moiety, e.g., a fluorophore.

In some aspects, provided herein is a method for analyzing a sample using a detectably-labeled set of probes. In some instances, the method comprises contacting the sample with a first plurality of detectably-labeled probes for targeting a plurality of analytes; performing a first detection round comprising detecting signals from the first plurality of detectably-labeled probes; contacting the sample with a second plurality of detectably-labeled probes for targeting the plurality of analytes; performing a second detection round of detecting signals from the second plurality of detectably-labeled probes, thereby generating a signal signature comprising a plurality of signals detected from the first detection round and second detection round, wherein the signal signature corresponds to an analyte of the plurality of analytes.

In some instances, detection of an optical signal signature comprises several rounds of detectably-labeled probe hybridization (e.g., contacting a sample with detectably-labeled probes), detectably-labeled probe detection, and detectably-labeled probe removal. In some instances, a sample is contacted with plurality first detectably-labeled probes, and said probes are hybridized to a plurality of nucleic acid analytes within the sample in decoding hybridization round 1. In some instances, a first detection round is performed following detectably-labeled probe hybridization. After hybridization and detection of a first plurality of detectably-labeled probes, probes are removed, and a sample may be contacted with a second plurality round of detectably-labeled probes targeting the analytes targeted in decoding hybridization round 1. The second plurality of detectably-labeled probes may hybridize to the same nucleic acid(s) as the first plurality of detectably-labeled probes (e.g., hybridize to an identical or hybridize to new nucleic acid sequence within the same nucleic acid), or the second plurality of detectably-labeled probes may hybridize to different nucleic acid(s) compared to the first plurality of detectably-labeled probes. Following m rounds of contacting a sample with a plurality of detectably-labeled probes, probe detection, and probe removal, ultimately a unique signal signature to each nucleic acid is produced that may be used to identify and quantify said nucleic acids and the corresponding analytes (e.g., if the nucleic acids themselves are not the analytes of interest and each is used as part of a labelling agent for one or more other analytes such as protein analytes and/or other nucleic acid analytes).

In some instances, after hybridization of a detectably-labeled probes (e.g., fluorescently labeled oligonucleotide) that detects a sequence (e.g., barcode sequence on a secondary probe or a primary probe), and optionally washing away the unbound molecules of the detectably-labeled probe, the sample is imaged and the detection oligonucleotide or detectable label is inactivated and/or removed. In some instances, removal of the signal associated with the hybridization between rounds can be performed by washing, heating, stripping, enzymatic digestion, photo-bleaching, displacement (e.g., displacement of detectably-labeled probes with another reagent or nucleic acid sequence), cleavage, quenching, chemical degradation, bleaching, oxidation, or any combinations thereof.

In some examples, removal of a probe (e.g., un-hybridizing the entire probe), signal modifications (e.g., quenching, masking, photo-bleaching, signal enhancement (e.g., via FRET), signal amplification, etc.), signal removal (e.g., cleaving off or permanently inactivating a detectable label) can be performed. Inactivation may be caused by removal of the detectable label (e.g., from the sample, or from the probe, etc.), and/or by chemically altering the detectable label in some fashion, e.g., by photobleaching the detectable label, bleaching or chemically altering the structure of the detectable label, e.g., by reduction, etc.). In some instances, the fluorescently labeled oligonucleotide and/or the intermediate probe hybridized to the fluorescently labeled oligonucleotide (e.g., bridge probe or L-probe) can be removed. In some instances, a fluorescent detectable label may be inactivated by chemical or optical techniques such as oxidation, photobleaching, chemically bleaching, stringent washing or enzymatic digestion or reaction by exposure to an enzyme, dissociating the detectable label from other components (e.g., a probe), chemical reaction of the detectable label (e.g., to a reactant able to alter the structure of the detectable label) or the like. For instance, bleaching may occur by exposure to oxygen, reducing agents, or the detectable label could be chemically cleaved from the nucleic acid probe and washed away via fluid flow.

In some instances, removal of a signal comprises displacement of probes with another reagent (e.g., probe) or nucleic acid sequence. For example, a given probe (e.g., detectably-labeled probes and/or the intermediate probe hybridized to the fluorescently labeled oligonucleotide (e.g., bridge probe or L-probe)) may be displaced by a subsequent probe that hybridizes to an overlapping region shared between the binding sites of the probes. In some cases, a displacement reaction can be very efficient, and thus allows for probes to be switched quickly between cycles, without the need for chemical stripping (or any of the damage to the sample that is associated therewith). In some instances, a sequence for hybridizing the subsequent or displacer probe (i.e. a toehold sequence) may be common across a plurality of probes capable of hybridizing to a given binding site. In some aspects, a single displacement probe can be used to simultaneously displace detection probes bound to an equivalent barcode position from all of the RCPs within a given sample simultaneously (with the displacement mediated by the subsequent detection probes). This may further increase efficiency and reduce the cost of the method, as fewer different probes are required.

After a signal is inactivated and/or removed, then the sample is re-hybridized in a subsequent round with a subsequent fluorescently labeled oligonucleotide, and the oligonucleotide can be labeled with the same color or a different color as the fluorescently labeled oligonucleotide of the previous cycle. In some instances, as the positions of the analytes, probes, and/or products thereof can be fixed (e.g., via fixing and/or crosslinking) in a sample, the fluorescent spot corresponding to an analyte, probe, or product thereof remains in place during multiple rounds of hybridization and can be aligned to read out a string of signals associated with each target analyte.

Decoding:

A "decoding process" is a process comprising a plurality of decoding cycles in which different sets of barcode probes are contacted with target analytes (e.g., mRNA sequences) or target barcodes (e.g., barcodes associated with target analytes) present in a sample, and used to detect the target sequences or associated target barcodes, or segments thereof. In some instances, the decoding process comprises acquiring one or more images (e.g., fluorescence images) for each decoding cycle. Decoded barcode sequences are then inferred based on a set of physical signals (e.g., fluorescence signals) detected in each decoding cycle of a decoding process. In some instances, the set of physical signals (e.g., fluorescence signals) detected in a series of decoding cycles for a given target barcode (or target analyte sequence) may be considered a "signal signature" for the target barcode (or target analyte sequence). In some instances, a decoding process may comprise, e.g., 1, 2, 3, 4, 5, 6, 7, 8, 9, 10, or more than 10 decoding cycles. In some instances, each decoding cycle may comprise contacting a plurality of target sequences or target barcodes with 1, 2, 3, 4, 5, 6, 7, 8, 9, 10, or more than 10 barcode probes (e.g., fluorescently-labeled barcode probes) that are configured to hybridize or bind to specific target sequences or target barcodes, or segments thereof. In some instances, a decoding process may comprise performing a series of in situ barcode probe hybridization steps and acquiring images (e.g., fluorescence images) at each step. Systems and methods for performing multiplexed fluorescence in situ hybridization and imaging are described in, for example, WO 2021/127019 A1; U.S. Pat. No. 11,021,737; and PCT/EP2020/065090 (WO2020240025A1), each of which is incorporated herein by reference in its entirety.

Anchor Probes:

In some instances, the present methods may further involve contacting the target analyte, e.g., a nucleic acid molecule, or proxy thereof with an anchor probe. In some instances, the anchor probe comprises a sequence complementary to an anchor probe binding region, which is present in all target nucleic acid molecules (e.g., in primary or secondary probes), and a detectable label. The detection of the anchor probe via the detectable label confirms the presence of the target nucleic acid molecule. The target nucleic acid molecule may be contacted with the anchor probe prior to, concurrently with, or after being contacted with the first set of detection probes. In some instances, the target nucleic acid molecule may be contacted with the anchor probe during multiple decoding cycles. In some instances, multiple different anchor probes comprising different sequences and/or different reporters may be used to confirm the presence of multiple different target nucleic acid molecules. The use of multiple anchor probes is particularly useful when detection of a large number of target nucleic acid molecules is required, as it allows for optical crowding to be reduced and thus for detected target nucleic acid molecules to be more clearly resolved Described herein is a method applying the aforementioned techniques to reduce optical crowding in an assay. In some instances, a method can include analyzing a biological sample, by contacting the biological sample with a first number of primary probe(s) configured to hybridize to a first target nucleic acid and a second number of primary probes configured to hybridize to a second target nucleic acid, each primary probe including a target-hybridizing region configured to hybridize to a different target region in the corresponding target nucleic acid, and a barcode region, and the first number is 1 or more, and the second number is greater than the first number, contacting the biological sample with a plurality of detectable probes, wherein each detectable probe is configured to hybridize to a barcode sequence in the barcode regions of the first number of primary probe(s) and/or the second number of primary probes, or a complement of the barcode sequence, detecting a signal associated with the plurality of detectable probes or absence thereof at one or more locations in the biological sample, and contacting the biological sample with a subsequent plurality of detectable probes, wherein each detectable probe in the subsequent plurality is configured to hybridize to a subsequent barcode sequence in the barcode regions of the first number of primary probe(s) and/or the second number of primary probes, or a complement of the subsequent barcode sequence. In some instances, wherein the second number is greater than the first number, the difference is based on absolute or relative numbers of the first target nucleic acid and second target nucleic acid in a sample. In some instances, the difference between second and first number is linearly or non-linearly proportional to absolute or relative numbers of the first target nucleic acid and second target nucleic acid in a sample. In some instances, the difference is inversely proportional, where the first number is for first target nucleic acid present in greater amounts (i.e., abundant), and the greater second number is for second target nucleic acid present in lesser amounts.

In Situ Code Design & Assignment Methods for Minimizing Optical Crowding:

Methods to minimize or eliminate the effects of optical crowding during detection during an assay and/or via decoding of barcoded target analytes are described that are based on code word design and/or their assignment to the barcoded target analytes to be detected. Separate, but complementary techniques for minimizing optical crowding are disclosed: (i) code word dilution, (ii) optimized assignment of code words to target analytes, (iii) target probe code word splitting, and (iv) attenuation. All of these approaches comprise the use of a decision rule (or decision process) for assignment of code words to barcoded target analytes that is designed to spread detectable signals corresponding to "ON bits" in the code words more-or-less evenly over a plurality of decoding cycles and/or detection channels.

Code word dilution: Dilution coding is an approach in which the code words in a set of code words (i.e., a "codebook") used to encode a plurality of target analytes are designed to have the smallest possible weights, where the weight of a code word is equal to the total number of ON bits in a given code word (where ON bits correspond to the decoding cycles and/or detection channels for which a signal is detected for the code word). Table 1 provides non-limiting examples of binary code words and their corresponding code word weights. The code word weight thus determines how often the corresponding barcoded target analyte will be visible/detectable during the decoding process.

TABLE 1

Non-limiting examples of binary code words ("1" = ON bit; "0" = OFF bit) and corresponding code word weights.

| Decoding Cycle Detection Channel | Decoding Cycle 1 | | | | Decoding Cycle 2 | | | | Code Word Weight |
|---|---|---|---|---|---|---|---|---|---|
| | 1 | 2 | 3 | 4 | 1 | 2 | 3 | 4 | |
| Code Word 1 | 1 | 0 | 0 | 0 | 0 | 1 | 0 | 0 | 2 |
| Code Word 2 | 0 | 1 | 0 | 0 | 0 | 0 | 1 | 0 | 2 |
| Code Word 3 | 0 | 0 | 1 | 0 | 0 | 0 | 0 | 1 | 2 |
| Code Word 4 | 0 | 0 | 0 | 1 | 1 | 0 | 0 | 0 | 2 |

In contrast with in situ methods such as seqFISH+ (see, e.g., Eng, et al. (2019), "Transcriptome-Scale Super-Resolved Imaging in Tissues by RNA seqFISH+", ibid.) which utilize a particular structured coding approach (i.e., pseudocolors) to achieve greater multiplexing capability, the methods described herein comprise a more general approach to binary code design and assignment to targets to minimize optical crowding by spreading the signal over a plurality of decoding cycles and detection channels. Each detection channel of each decoding cycle is considered to correspond to a distinct bit of the code word. The smallest possible code word weights (i.e., the smallest possible total number of ON bits per code word) are used for codebook design while still ensuring that codebook size requirements (e.g., the number of unique code words included in the codebook) are met and other code word design constraints, such as minimum pairwise Hamming distance and/or additional heuristic filters on valid code words, are satisfied. In some instances, a majority of the bits in each code word of the codebook are OFF bits. In some instances, each of the code words comprises a same total number of ON bits. In some instances, at least a portion of the code words comprise a different number of ON bits.

In some instances, the number of unique code words included in a codebook may be at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ unique code words. In some instances, a codebook may comprise any number of unique code words within the range of values in this paragraph, e.g., 1,225 unique code words or $2.38\times10^6$ unique code words.

In some instances, the length of a code word (i.e., the number of bits in a code word of the codebook) is given by $N\times K$, where N is the number of decoding cycles and K is the number of detection channels. In some instances, the number of decoding cycles used for decoding a plurality of barcoded target analytes is 2, 3, 4, 5, 6, 7, 8, 9, 10, 11, 12, 13, 14, 15, 16, 17, 18, 19, 20, or more than 20 decoding cycles. In some instances, the number of detection channels used for decoding the plurality of barcoded target analytes is one, two, three, four, or more than four detection channels, where a separate image may be acquired for each of the one, two, three, four, or more than four detection channels in each of the decoding cycles.

In some instances, the weight of all code words in a given code book may be the same. In some instances, the weight of a portion of the code words in a given codebook may be different from the weights for other portions of the codebook. In some instances, the weight of each code work in a given codebook may be different from the weights for every other code word in the codebook. In some instances, the weight (or average weight) for the code words, or a portion thereof, in a given codebook may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100.

In some instances, the code words in a given codebook may be designed to meet a specified pairwise edit distance (e.g., a specified minimum pairwise edit distance) so as to enable code word error detection and correction. An "edit distance" is a numerical value that quantifies how different two strings (e.g., text strings) are from one another by counting the minimum number of editing operations required to transform one string into the other. Examples of edit distance metrics include, but are not limited to, Hamming distance, Levenshtein distance, longest common subsequence (LCS) distance, and the like. For example, the Levenshtein distance between two strings is the minimum number of single-character edits (e.g., insertions, deletions, or substitutions) required to transform one string into the other. The longest common subsequence (LCS) distance is the edit distance for which the only allowed edit operations are insertions and deletions, each of which is assigned a unit cost. The Hamming distance between two strings of equal length (i.e., substitutions are the only edit operations allowed) is the number of positions in the two strings at which the corresponding symbols are different.

Hamming distances and/or Levenshtein distances (where the error penalties assigned for differences between two strings are integer valued, e.g., "1") allow for a natural interpretation of error correction, with minimum pairwise code word distances of 2k+1 allowing for correction of up to k errors. In some instances, the designed code words of a given codebook may be required to have a minimum pairwise edit distance (e.g., a minimum pairwise Hamming distance, a minimum pairwise Levenshtein distance, or a minimum pairwise LCS distance) such that they guarantee an error correction capability of correcting at least 1, at least 2, at least 3, at least 4, at least 5, at least 6, at least 7, at least 8, at least 9, or at least 10 code word errors (e.g., errors arising during the decoding process).

In some instances, the code words for a given codebook may be designed to further satisfy a number of heuristic filter requirements. Examples of heuristic filter requirements include, but are not limited to, required gene transcript-L-probe combinations, required gene transcript-code word combinations, required L-probe-code word combinations, limiting the code word to having at most one ON bit within each group of 4 bits that correspond to 4 color readout channels, and/or requiring the code word to have ON bits that will appear in at least K distinct color channels (thereby improving one's confidence that the object is "real" and not a fluorescent background object).

In some instances, the code words in a code book may be assigned to a plurality of barcoded target analytes according to a decision rule (e.g., a minimax decision rule) designed to minimize a maximum predicted density of ON signals across the series of images acquired across one or more detection channels (e.g., 1, 2, 3, 4, or more than 4 detection channels) during a plurality of decoding cycles. For example, in some instances, the code words of the code book may be assigned to a plurality of barcoded targets (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ barcoded target analytes) according to a minimax decision rule that minimizes the maximum predicted density of ON signals (corresponding to ON bits of target analyte-associated code words) detected per image (e.g., where a different image of the biological sample is acquired or received for each of one, two, three, four, or more than four detection channels in each decoding cycle) for the series of images acquired during a plurality of decoding cycles (e.g., for 2, 3, 4, 5, 6, 7, 8, 9, 10, 11, 12, 13, 14, 15, 16, 17, 18, 19, 20, or more than 20 decoding cycles) used for decoding a plurality of barcoded target analytes.

In some instances, the code words in a code book may be assigned to a plurality of barcoded target analytes according to a decision rule that ensures that ON bits are distributed more-or-less evenly across the plurality of decoding cycles and detection channels used for decoding. For example, in some instances, the code words of the code book may be assigned to a plurality of barcoded targets (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ barcoded target analytes) according to a decision rule that ensures that a total number of ON signals detected in a given image for a given decoding cycle is within ±5%, ±10%, ±15%, ±20%, or ±25% of a mean number of ON signals detected per image (e.g., where a different image of the biological sample is acquired or received for each of one, two, three, four, or more than four detection channels in each decoding cycle) for the series of images acquired during a plurality of decoding cycles (e.g., for 2, 3, 4, 5, 6, 7, 8, 9, 10, 11, 12, 13, 14, 15, 16, 17, 18, 19, 20, or more than 20 decoding cycles) used for decoding a plurality of barcoded target analytes.

in some instances, the code words in a code book may be assigned to a plurality of barcoded target analytes according to a decision rule that ensures that the number of target analytes that are visible in a given image (e.g., the number of target analytes for which the corresponding code word has an ON bit in a given image) are distributed more-or-less evenly across the plurality of decoding cycles and detection channels used for decoding. For example, in some instances, the code words of the code book may be assigned to a plurality of barcoded targets (e.g., at least 5, at least 10, at least 20, at least 40, at least 60, at least 80, at least 100, at least 200, at least 400, at least 600, at least 800, at least 1,000, at least 2,000, at least 4,000, at least 6,000, at least 8,000, at least 10,000, at least 20,000, at least 40,000, at least 60,000, at least 80,000, at least 100,000, at least 200,000, at least 400,000, at least 600,000, at least 800,000, at least 1,000,000, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $10^7$, at least $10^8$, at least $10^9$, or more than $10^9$ barcoded target analytes) to ensure that the number of target analytes that are visible (e.g., that have a corresponding code word that has an ON bit) in a given image for a given decoding cycle is within ±5%, ±10%, ±15%, ±20%, or ±25% of a mean number of target analytes that are detected per image (e.g., where a different image of the biological sample is acquired or received for each of one, two, three, four, or more than four detection channels in each decoding cycle) for the series of images acquired during a plurality of decoding cycles (e.g., for 2, 3, 4, 5, 6, 7, 8, 9, 10, 11, 12, 13, 14, 15, 16, 17, 18, 19, 20, or more than 20 decoding cycles) used for decoding a plurality of barcoded target analytes.

In some instances, code words may be assigned to barcoded target analytes using a minimax decision rule (e.g., designed to minimize a maximum predicted density of ON signals across the series of images), a mean ON signal decision rule (e.g., designed to ensure that a total number of ON signals detected in a given image for a given decoding cycle is within ±5%, ±10%, ±15%, ±20%, or ±25% of a mean number of ON signals detected per image), a mean target number decision rule (e.g., designed to ensure that the number of target analytes that are visible (e.g., that have a corresponding code word that has an ON bit) in a given image for a given decoding cycle is within ±5%, ±10%, ±15%, ±20%, or ±25% of a mean number of target analytes that are detected per image), or any combination thereof.

In some instances, the decision rule (or decision process) may be implemented in an iterative manner. For example, in some instances, the one or more code words may be rank-ordered according to code word weight, the one or more barcoded target analytes may be rank-ordered according to a predicted density (as will be discussed in more detail below), and the one or more rank-ordered code words may be assigned to the one or more rank-ordered barcoded target analytes using an iterative process repeated for each of the one or more barcoded target analytes in decreasing order of maximum predicted density, the iterative process comprising: computing a predicted density of ON signals for every combination of remaining, unassigned code words and the barcoded target analyte across the series of decoding images; selecting a code word from the remaining, unassigned code words that minimizes the predicted density of ON signals across the series of images; and assigning the selected code word to the barcoded target analyte. In some instances, the iterative process may further comprise reviewing previous assignments of code words to barcoded target analytes, and changing the code word selected for the current barcoded target analyte to minimize the predicted density of ON signals across the series of images for barcoded target analytes to which code words have been previously assigned.

Optimized target analyte—code word assignment: Optimized assignment of code words to target analytes is an approach in which code words are assigned to corresponding barcoded target analytes according to a decision rule based on prior knowledge of an abundance or distribution of target analytes in a given biological sample, e.g., expression data for the target analytes, to reduce the weight of code words corresponding to highly expressed target analytes. In some instances, code words may be assigned to corresponding barcoded target analytes according to a decision rule based on, e.g., single cell expression data for the target analytes in clustered cell types, to reduce the weight of code words corresponding to highly expressed target analytes, where the clustered cell types represent a distribution of cell types found in the biological sample. In some instances, the expression data for the one or more target analytes comprises bulk gene expression data, bulk protein expression data, spatial gene expression data, spatial protein expression data, single cell gene expression data, single cell protein expression data, or any combination thereof.

Assume, for example, that single cell expression data (e.g., single cell gene expression data or single cell protein expression data) is available for the biological sample of interest (e.g., a tissue sample of interest) where the expression data has been clustered according to cell type clusters, each with an average gene or protein expression profile, and where the clustered cell types represent a distribution of cell types found in the biological sample. In some instances, the clustered single cell expression data may provide the best prior information for the expression profiles likely to be observed in the in situ experiment, where the density of labeled features or spots (e.g., labeled RCPs) is likely to mimic the expression profiles.

Given a codebook, and an assignment of target analytes (e.g., gene transcripts) to code words in the codebook, we can use the single cell type expression data to determine the expected density of labeled spots that will be observed for each cell type in each decoding cycle and detection channel of the decoding process.

For a random assignment of code words to target analytes (e.g., gene transcripts), two genes that are highly expressed in the same cell type may end up being assigned code words that cause both of the genes to be in the ON state (i.e., having a detectable signal) simultaneously in one or more bits of the corresponding code words (i.e., in one or more decoding cycles and/or detection channels), which may cause optical crowding to occur for those bits.

Alternatively, one may select the code word for each gene transcript to explicitly avoid this situation and reduce the incidence of over-crowded cycles, thereby distributing the number (or density) of ON features (e.g., ON RCPs) more evenly over a plurality of decoding cycles and detection channels. As indicated above, in some instances the code words may be selected/assigned according to a decision rule (e.g., a minimax decision rule) that minimizes the maximum predicted density of ON signals in the images acquired during a cyclic decoding process. In some instances, code words may be selected/assigned according to a decision rule (e.g., a mean ON signal decision rule) that ensures that a total number of ON signals detected in an image for a given decoding cycle is within ±5%, ±10%, ±15%, ±20%, or ±25% of a mean number of ON signals detected per image. In some instances, the code words may be selected/assigned according to a decision rule (e.g., a mean target number decision rule) that ensures that the number of target analytes that are visible (e.g., that have a corresponding code word that has an ON bit) in a given image for a given decoding cycle is within ±5%, ±10%, ±15%, ±20%, or ±25% of a mean number of target analytes that are detected per image. In any of these instances, the decision rule may further comprise assignment based on expression data.

In some instances, for example, the code words may be rank-ordered according to code word weight, the barcoded target analytes may be rank-ordered according to a maximum expression level across clustered cell types, and the rank-ordered code words may be assigned to the rank-ordered barcoded target analytes using an iterative process repeated for each of the barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some instances, the iterative process may further comprise reviewing previous assignments of code words to barcoded target analytes, and changing the code word selected for the current barcoded target analyte to minimize the predicted density of ON signals across the series of images for barcoded target analytes to which code words have been previously assigned.

In some instances, for example, the code words may be rank ordered according to code word weight (i.e., the total number of ON bits in a given code word), and the barcoded target analytes to be detected may be rank ordered according to their corresponding single cell expression data or predicted density in the sample. In some instances, the lowest ranked code word may then be assigned to the highest ranked barcoded target analyte.

In some instances, an algorithm may be developed to assign code words to, e.g., gene transcripts, where the assignment algorithm is optimized to minimize optical crowding and distribute the total number or density of ON bits over the plurality of decoding cycles and detection channels. Table 2 provides a non-limiting example of a design process outline for a greedy algorithm (an optimization algorithm that follows the problem-solving heuristic of making a locally optimal choice at each stage of optimization) being developed to assign code words to target analytes (e.g., gene transcripts) in decreasing order of the predicted density of each gene transcript based on the single cell type expression data. In some instances, the optimization algorithm may comprise a simulated annealing algorithm. In some instances, the optimization problem may be cast as an integer programming problem, and solved with existing integer programming tools.

TABLE 2

Exemplary design process outline for a greedy algorithm developed to assign code words to gene transcripts based on single cell expression data.

/// Design process:
/// 1. Rank order gene transcripts in descending order of predicted maximum density
/// 2. For each gene, consider all possible L-probe & code word combinations, subject to optional required gene transcript-L-probe, gene transcript-code word, or L-probe-code word combinations.
/// 3. Score each remaining combination of L-probe and code word based on predicted spot (e.g., labeled RCP) density over all cycles and cell types. A scoring term that penalizes combinations of L-probe and gene will result in RCP sequences contain secondary structure predicted to interfere with the binding of readout probes can also be added to the score.
/// 4. Pick the best scoring combinations (e.g., the combination of L-probe/code word assignments that minimize the maximum predicted density of labeled RCPs), mark the L-probe and code word assignments as used, and register the decision with the density optimizer.

Target probe code word splitting: Highly expressed genes may cause optical crowding in ON bits of the code word assigned to them even if no other genes are ON in those bits. Disclosed herein is a strategy for mitigating this effect: target probe code word splitting. In a conventional in situ analysis method, each target analyte, e.g., an mRNA, is targeted by 8 padlock probes, each containing the same L-probe binding barcode and thus the same code word. The probability of any one padlock probe forming an RCP is small, therefore each transcript is typically labelled by 1 or at most two RCPs, which are assumed to be derived from a uniformly random subset of the 8 padlock probes.

In a target probe code word splitting design, different code words are used for different subsets of the padlock probes targeting the same target analyte, e.g., a gene transcript. For example, padlock probes 1 to 4 may be assigned code word A, and padlock probes 5 to 8 may be assigned code word B. Alternatively, each padlock probe may be assigned a distinct code word. Groups of code words to be assigned to a "split" gene transcript (called a "splitting group") are selected according to the following constraints:

1. Code words in the splitting group have a mutually disjoint set of ON bits. This serves to distribute the optical signals associated with the gene transcript more evenly over more code word bits.
2. For each pair of code words within a splitting group, a new code word is formed that is the bitwise-OR of the two code words. Each such code word is termed an "OR-code word". The set of "OR-code words" formed by a splitting groups are designed to have a minimum pairwise Hamming distance of >=6 with respect to each other and with respect to any other single code word of the splitting group. This permits one to correctly decode gene transcripts that are labelled by two RCPs having different code words from the same splitting group.

In some instances, gene splitting includes 2-way, 4-way, and/or 8-way splitting. In some instances, gene splitting is applied for cells of about 5-10, about 10-30, about 30-50, about 50-100, about 100-150, about 150-250, about 250-500, about 500-750, about 750-1000, about 1000 or more transcripts per cell. As an example, gene splitting may be applied in instances where 10-30 transcripts per cell are present, but as appreciated by one of skill, absolute transcript numbers goes up proportionally with the number of transcripts per cell the technology is capable of detecting. In other instances, choice of 2-way, 4-way, and/or 8-way splitting depends on absolute or relative levels of expression, appearance of a gene in multiple cell types at different levels and/or its biological relevance.

FIG. 1A provides a non-limiting schematic illustration of a conventional, non-split in situ code design (upper) and a target probe code word splitting design (lower) for in situ analysis. In the non-split scenario, the target gene transcript (wavy line) is labeled by two RCPs (probes 1 and 2; coiled lines), each comprising the same code word A. In this scenario, one always observes code word A. In the gene splitting scenario, probes 1 and 2 comprise code words A and B respectively, giving rise to three possible outcomes. In one possible outcome (case 1), only probe 1 forms an RCP and one only observes code word A. In a second possible outcome (case 2), only probe 2 forms and RCP and one only observes code word B. In the third possible outcome (case 3), both probes form RCPs and one observes both code word A and code word B. During decoding, the gene transcript labeled by the two RCPs is in the ON state if either code word A or code word B has an ON bit. Because the probabilities for observing the first and second (case 1 and case 2) outcomes are approximately the same, and much greater than the probability of observing the third (case 3) outcome, the density contributed by the ON bits of code words A and B is roughly halved.

Target probe code word attenuation: In other instances where highly expressed genes cause optical crowding in ON bits of the code word assigned to them even if no other genes are ON in those bits, another approach is gene attenuation. Here, the sensitivity of in situ detection of selected target analytes, e.g., gene transcripts, may be intentionally reduced through code word attenuation, that is, by selecting code words for one or more of the padlock probes that target the selected gene transcripts that are composed primarily of OFF bits or that comprise nothing but OFF bits (such that there is little or no detectable signal associated with those code words). This approach can be used to reduce the optical crowding "budget" consumed by highly expressed genes, while still providing the ability to detect and quantify those gene transcripts. In some instances, gene attenuation includes application to genes where the transcripts exceed about 5%-10%, about 10%-15%, about 15%-20%, about 20%-25%, or 25% or more of an optical crowding budget for a cell. In some instances, gene splitting is applied for cells of about 5-10, about 10-30, about 30-50, about 50-100, about 100-150, about 150-250, about 250-500, about 500-750, about 750-1000, about 1000 or more transcripts per cell. As an example, gene attenuation may be applied in instances where about greater than 20 transcripts per cell are present, but as appreciated by one of skill, absolute transcript numbers goes up proportionally with the number of transcripts per cell the technology is capable of detecting. In other instances, application of gene decimation depends on absolute or relative levels of expression, appearance of a gene in multiple cell types at different levels and/or its biological relevance.

Systems for In Situ Code Design to Minimize Optical Crowding:

Also disclosed herein are systems configured for performing any of the described multi-resolution decoding methods. For example, a system may comprise: one or more processors; and a memory communicatively coupled to the one or more processors and configured to store instructions that, when executed by the one or more processors, cause the system to: receive a series of images of a biological sample, wherein the series of images comprises images from a plurality of decoding cycles; detect, in the images of the series of images, a series of detectable signals (ON signals) or absence thereof (OFF signals) at one or more locations in the biological sample corresponding to one or more barcoded target analytes; determine, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identify the one or more barcoded target analytes based on the one or more code words.

In some instances, the instructions, when executed by the one or more processors, cause the system to assign the one or more code words to the one or more barcoded target analytes based on expression data for the one or more target analytes in clustered cell types, and wherein the clustered cell types represent a distribution of cell types found in the biological sample. In some instances, the expression data for the one or more target analytes comprises bulk gene expression data, bulk protein expression data, spatial gene expression data, spatial protein expression data, single cell gene expression data, single cell protein expression data, or any combination thereof. In some instances, the instructions, when executed by the one or more processors, cause the system to rank-order the one or more code words according to code word weight, rank-order the one or more barcoded target analytes according to a maximum expression level across all clustered cell types, and assign the one or more rank-ordered code words to the one or more rank-ordered barcoded target analytes using an iterative process repeated for each of the one or more barcoded target analytes in decreasing order of maximum expression level, the iterative process comprising: computing a predicted density of ON signals for every combination of remaining, unassigned code words and the barcoded target analyte across the series of images; selecting a code word from the remaining, unassigned code words that minimizes the predicted density of ON signals across the series of images; and assigning the selected code word to the barcoded target analyte. In some instances, the iterative process may further comprise reviewing previous assignments of code words to barcoded target analytes, and changing the code word selected for the current barcoded target analyte to minimize the predicted density of ON signals across the series of images for barcoded target analytes to which code words have been previously assigned. In some instances, the iterative process may be performed using a greedy algorithm, a simulated annealing algorithm, or a combination thereof.

In some instances, two or more barcodes may be assigned to a barcoded target analyte, and the instructions, when executed by the one or more processors, cause the system to: detect a code word that corresponds to one of the two or more barcodes assigned to the barcoded target analyte based on the series of ON and OFF signals detected in the series of images; and identify the barcoded target analyte based on the code word. In some instances, the instructions, when executed by the one or more processors, may further cause the system to detect a logical OR code word that corresponds to two of the two or more barcodes assigned to the barcoded target analyte based on the series of ON and OFF signals detected in the series of images; and identify the barcoded target analyte based on the logical OR code word. In some instances, all of the bits for a code word corresponding to at least one of the two or more barcodes assigned to the barcoded target analyte may be OFF bits, thereby ensuring that no signal is detected for the code word in the series of images and reducing a sensitivity of detecting one or more barcoded target analytes.

Figure 1B:
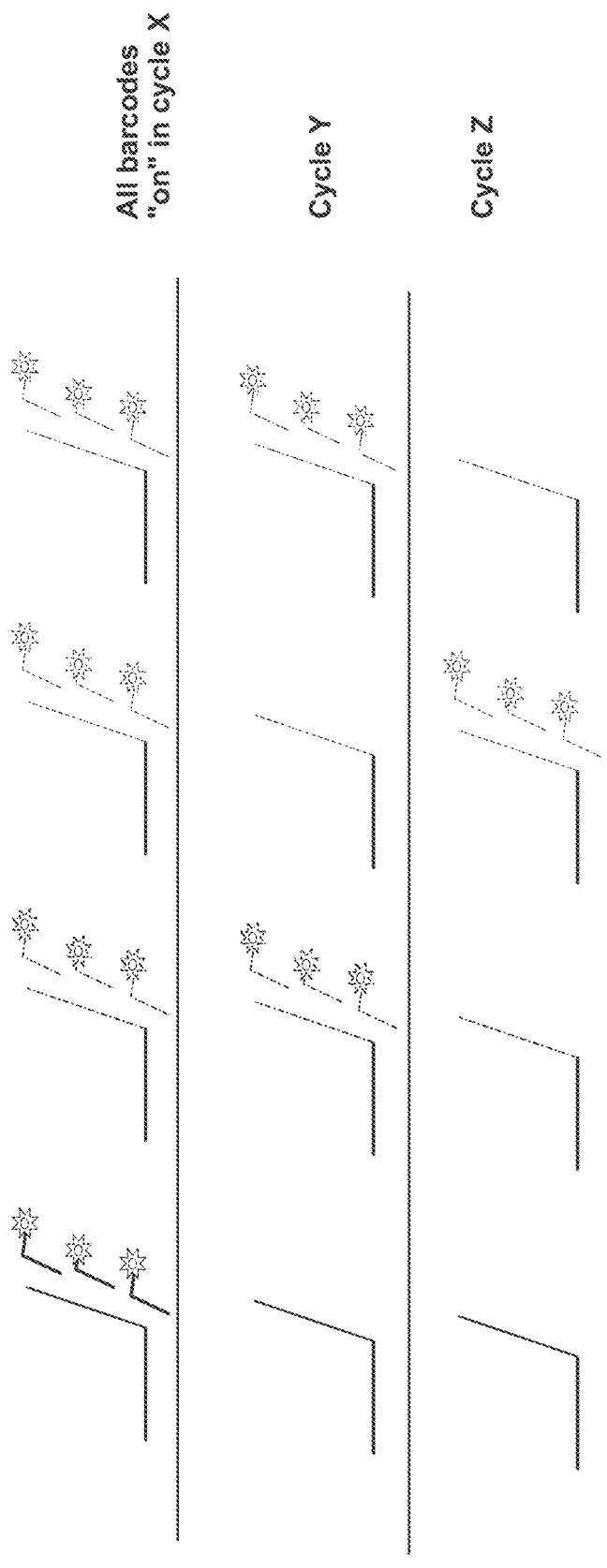
FIG. 1B illustrates gene splitting to minimize optical crowding, according to various embodiments.

FIG. 1B illustrates gene splitting to minimize optical crowding. In various embodiments, each of the primary probes targeting a specific gene carries a different unique barcode. In various embodiments, at least one primary probe will not light up in the same round as other primary probes. In various embodiments, two or more primary probes having two or more different colors light up in the same round. As shown in FIG. 1B, during cycle Y, the primary probes light up in green and red. As shown in FIG. 1B, during cycle Z, the primary probes light up in yellow. In various embodiments, gene splitting can increase dynamic range as more transcripts from the same gene can be distinguished from one another in an optically crowded setting. In various embodiments, a gene can be split in $2^n$ ways. In various embodiments, using four different fluorophores (e.g., blue, green, yellow, red), a gene can be split up to 16 ways. In various embodiments, a gene can be split in 2 ways. In various embodiments, a gene can be split in 4 ways. In various embodiments, a gene can be split in 8 ways. In various embodiments, a gene can be split in 16 ways.

Figure 1C:
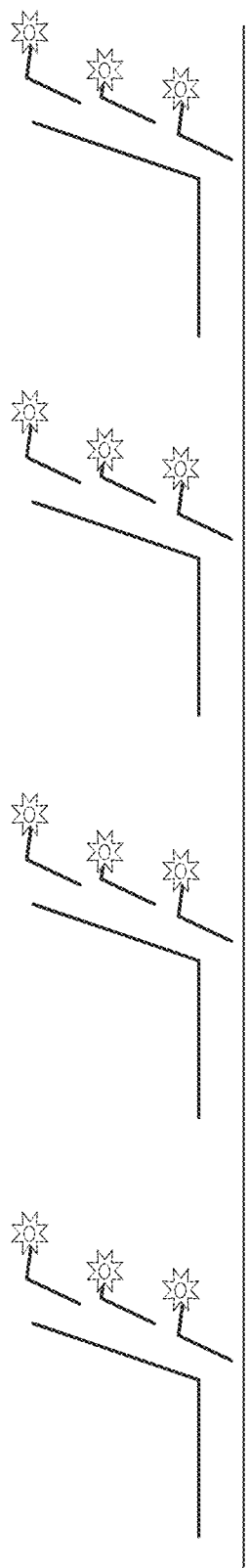
FIGS. 1C-1D illustrate gene dilution to minimize optical crowding, according to various embodiments.
Figure 1D:
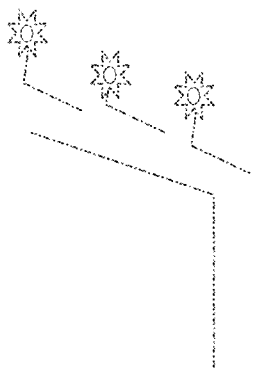

FIG. 1C and FIG. 1D illustrate gene dilution to minimize optical crowding. In various embodiments, the number of primary probes per gene is altered based on expression level. In various embodiments, low expressed genes are targeted with more probes (FIG. 1C) and high expressed genes are targeted with fewer probes (FIG. 1D). In various embodiments, each probe is labelled with sufficient number of fluorophores to be detected as an individual spot. In various embodiments, since not every probe on every transcript can generate a signal (e.g., due to inaccessibility of some transcripts at that target site or other reasons) a lower number of probes may generate a lower number of spots. In various embodiments, a higher number of probes will generate a higher number of spots. In various embodiments, gene dilution can increase the dynamic range of the assay by lowering optical crowding of high expressed genes.

Figure 1E:
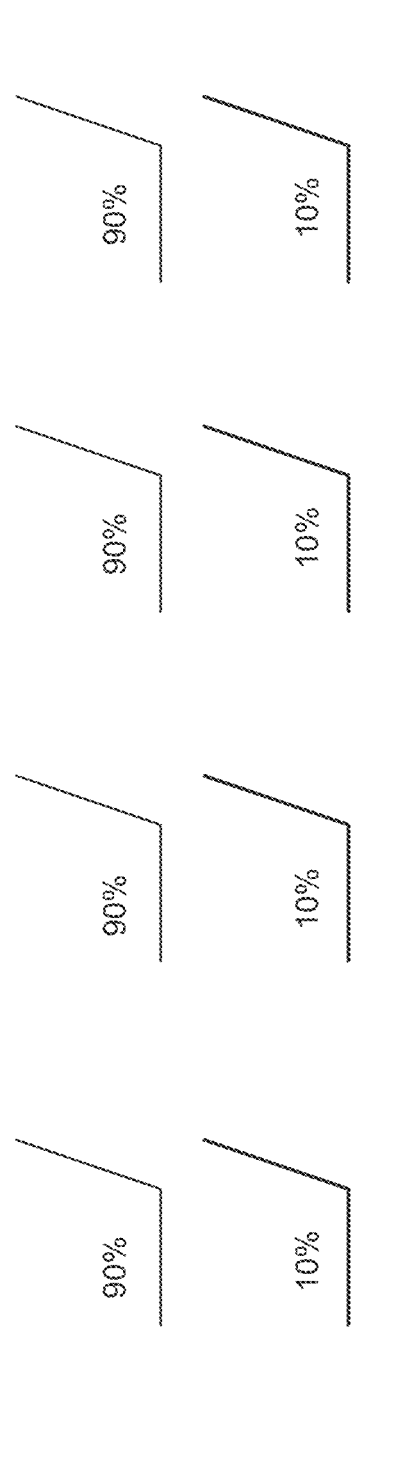
FIGS. 1E-1G illustrate gene decimation to minimize optical crowding, according to various embodiments.
Figure 1F:
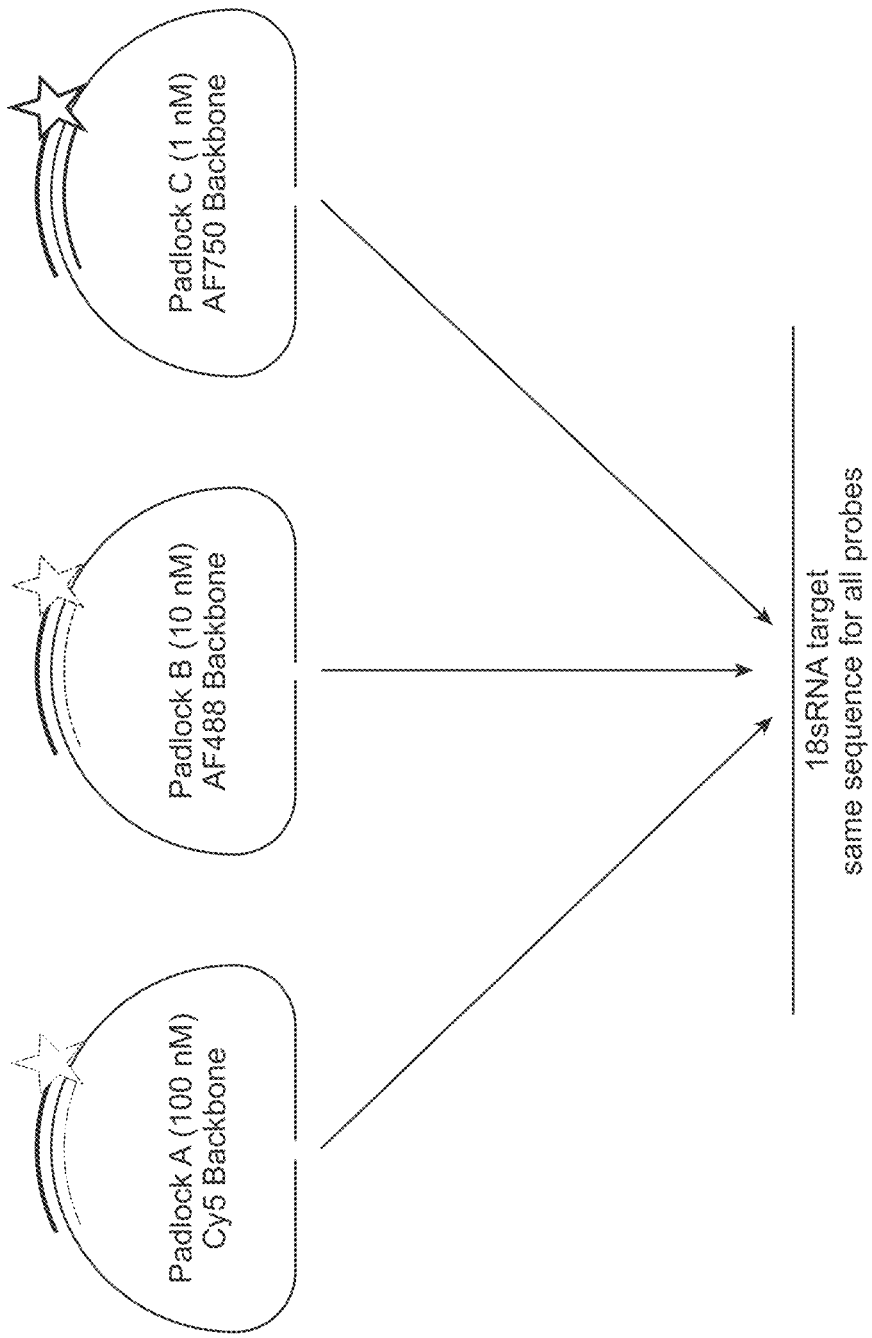
Figure 1G:
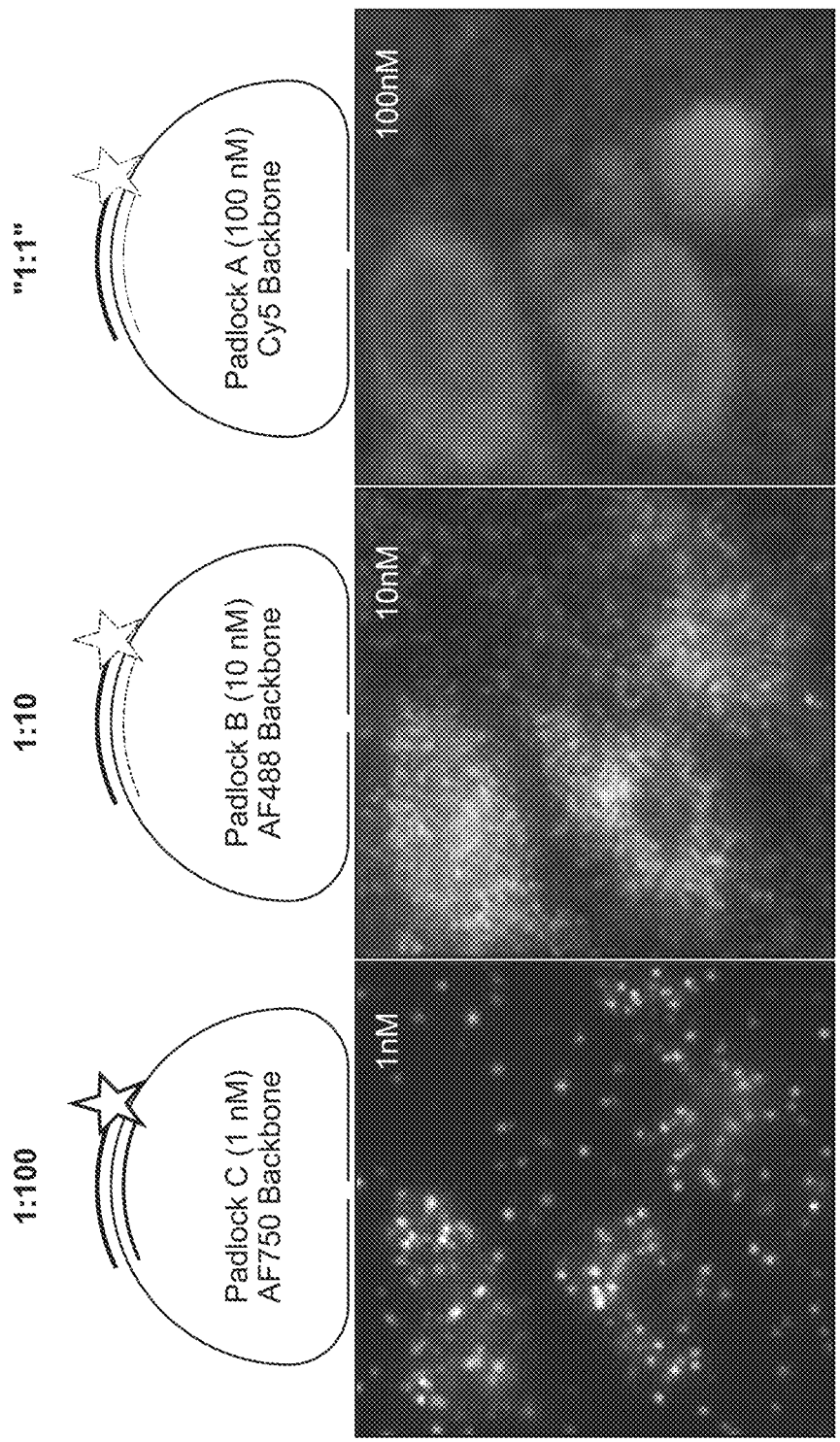

FIGS. 1E-1G illustrate gene decimation to minimize optical crowding. As shown in FIG. 1E, target sequences on a transcript are targeted with a different set of primary probes that compete for the same hybridization site. In various embodiments, a first set of probes having a first, higher concentration (e.g., 90%) has (i) a non-detectable overhang, or simply has no overhang, or (ii) carries a different barcode that can be detected in a different decoding scheme. In various embodiments, a second set of probes having a second concentration (e.g., 10%) that is lower than the first concentration are the probes that will generate a detectable signal. In various embodiments, every 10th primary probe will generate a signal, which leads to one in every 10th transcript generating a signal. In various embodiments, the ratio can be adjusted based on expression level and desired detection efficiency. In various embodiments, the ratio is one in every 100 transcripts. In various embodiments, the ratio is one in every 1,000 transcripts. In various embodiments, the ratio is one in every 2,000 transcripts. In various embodiments, the ratio is one in every 3,000 transcripts. In various embodiments, the ratio is one in every 4,000 transcripts. In various embodiments, the ratio is one in every 5,000 transcripts. In various embodiments, the ratio is one in every 6,000 transcripts. In various embodiments, the ratio is one in every 7,000 transcripts. In various embodiments, the ratio is one in every 8,000 transcripts. In various embodiments, the ratio is one in every 9,000 transcripts. In various embodiments, the ratio is one in every 10,000 transcripts. In various embodiments, the ratio is at least one in every 2,000 transcripts. In various embodiments, the ratio is at least one in every 3,000 transcripts. In various embodiments, the ratio is at least one in every 4,000 transcripts. In various embodiments, the ratio is at least one in every 5,000 transcripts. In various embodiments, the ratio is at least one in every 6,000 transcripts. In various embodiments, the ratio is at least one in every 7,000 transcripts. In various embodiments, the ratio is at least one in every 8,000 transcripts. In various embodiments, the ratio is at least one in every 9,000 transcripts. In various embodiments, the ratio is at least one in every 10,000 transcripts. In various embodiments, gene decimation can be used to down-tune detection efficiency for highly expressed genes, which can generate more decoding space/optical space and can increase the dynamic range.

As shown in FIG. 1F and FIG. 1G, padlock probes with different barcodes, but identical RNA binding arms, are added at different concentrations. In various embodiments, because the padlock probes compete for the same binding site, lower concentration padlock probes will hybridize less and, if sufficiently decimated, be quantifiable.

Figure 2:
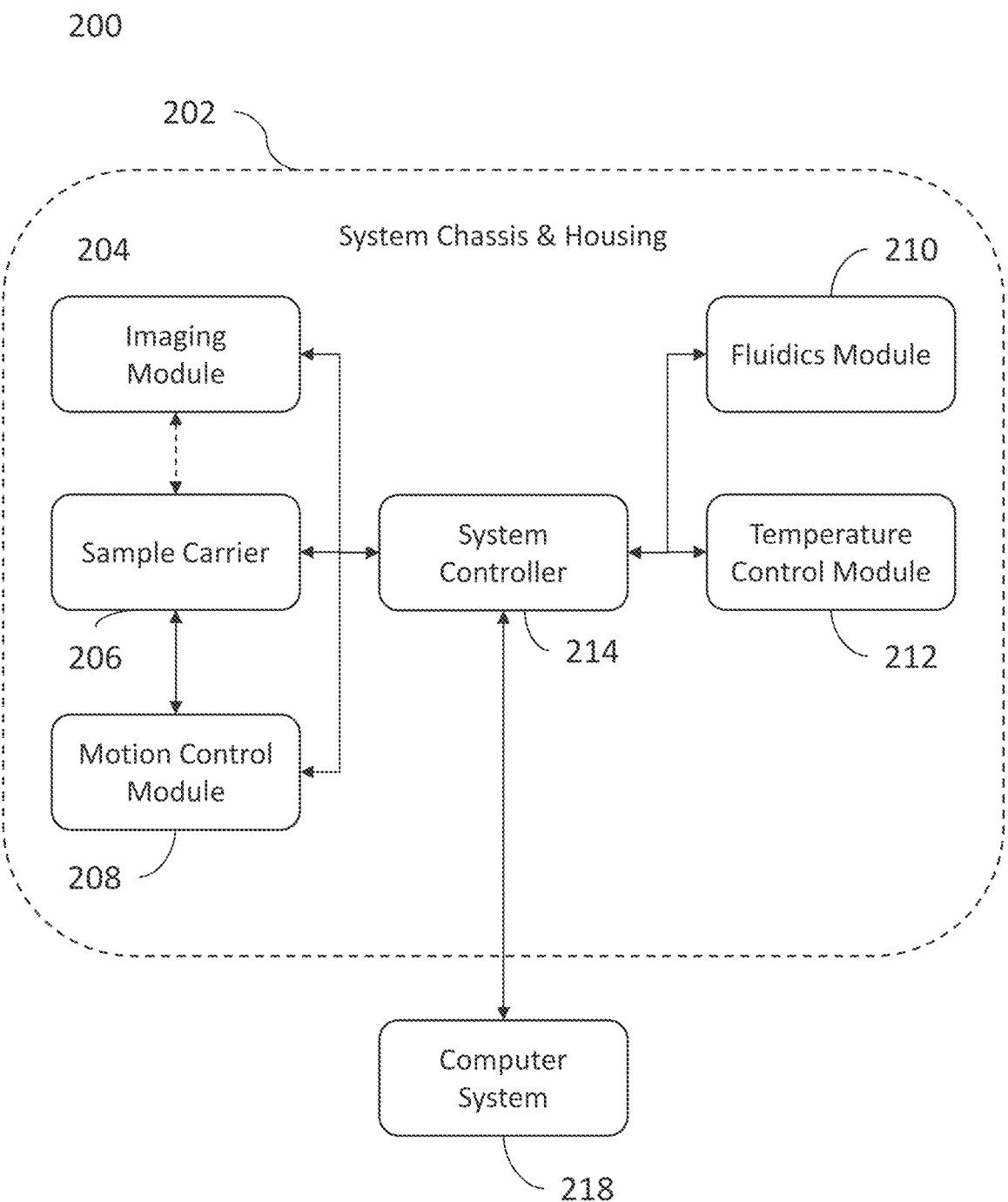
FIG. 2 provides a schematic illustration of a system configured to perform the in situ decoding methods described herein that minimize optical crowding.

As illustrated schematically in FIG. 2, a system 200 configured to implement the methods disclosed herein may comprise one or more imaging modules 204 (e.g., one or more commercial imaging instruments and/or one or more custom imaging modules), one or more additional processors or system controllers 214 (e.g., computers or computer systems), one or more sample carriers 206, one or more fluidics modules 210, one or more temperature control modules 212, one or more motion control modules 208 (which may comprise one or more translation and/or rotation stages), one or more system control software packages, one or more data analysis (e.g., image processing) software packages, or any combination thereof. In some instances, the system may comprise an integrated system, e.g., where the different functional subsystems are mounted on a single framework or chassis, and packaged within a single housing 202. In some instances, the system may comprise a modular system, e.g., where the different functional subsystems are mounted on separate frameworks or chassis, and packaged in separate housings. In some instances, the one or more system controllers 214 may interface with an external computer system 216.

Commercial optical imaging instruments: In some instances, the disclosed methods may utilize a commercial optical imaging instrument for detection and readout, e.g., a commercial fluorescence microscope or a fluorescence imaging microplate reader. Examples of suitable fluorescence microscopes include, but are not limited to, the Zeiss Axioscope 5 multichannel fluorescence microscope (Carl Zeiss Microscopy, LLC, White Plains, N), the Olympus BX63 automated fluorescence microscope (Olympus Scientific Solutions Americas Corp., Waltham, MA), and the Nikon Eclipse Ti2 fluorescence microscope (Nikon Instruments, Inc., Melville, NY). Examples of fluorescence imaging microplate readers include, but are not limited to, the Tecan Spark® Cyto multimode microplate reader (Tecan SP, Inc., Baldwin Park, CA) and the Molecular Devices SpectraMax i3x multimode microplate reader (Molecular Devices, San Jose, CA).

Custom optical imaging modules: In some instances, the disclosed methods may utilize a custom optical imaging instrument for detection and readout, e.g., a custom fluorescence imaging module (or fluorescence imaging unit), which may comprises one or more light sources, one or more objective lenses, one or more sample carriers (e.g., sample holders, sample stages, and/or translation stages), one or more tube lenses, one or more image sensors or cameras, one or more processors or controllers, one or more additional optical components (e.g., lenses, mirrors, prisms, beamsplitters, optical filters, colored glass filters, narrowband interference filters, broadband interference filters, dichroic reflectors, diffraction gratings, apertures, shutters, optical fibers, optical waveguides, acousto-optic modulators, and the like), or any combination thereof. In some instances, the custom imaging module may comprise a focus mechanism, e.g., an autofocus mechanism. In some instances, the custom imaging module may be configured to perform multichannel imaging, e.g., multichannel fluorescence imaging comprising the use of excitation light at one or more excitation wavelengths, and imaging the emitted fluorescence at two or more different emission wavelengths.

Objective lenses: The custom imaging modules disclosed herein, e.g., fluorescence imaging modules, may comprise one or more objective lenses of the same type or of different types. Examples of suitable objective lenses include, but are not limited to, low magnification objectives (e.g., 5× and 10× objectives), intermediate magnification objectives (e.g., 20× and 50× objectives), high magnification objectives (e.g., 100× objectives), designed to work with any suitable immersion media, including but not limited to, dry objectives, water immersion objectives, oil immersion objectives, cover slip-corrected objectives, infinity-corrected objectives, achromatic objectives, plan achromatic objectives, fluorite (or semi-apochromatic) objectives, plan fluorite objectives, and plan apochromatic objectives. In some instances, the one or more objective lenses may comprise objectives of a custom design that exhibit a specified magnification, numerical aperture, working distance, focal distance, etc., or any combination thereof.

In some instances, the one or more objective lenses may be fixed components of the imaging module. In some instances, the one or more objective lenses may be moveable (or replaceable) components of the imaging module, e.g., by mounting them on a rotatable turret, mounting them on a translatable slide or stage, etc. In some instances, the one or more objective lenses may comprise both fixed and moveable (or replaceable) components of the imaging module.

Objective lens magnification: In some instances, the magnification of the one or more objective lenses may be the same or may be different, and may range from about 2× to about 100×. In some instances, the magnification of the one or more objective lenses may be at least 2×, at least 5×, at least 10×, at least 15×, at least 20×, at least 25×, at least 30×, at least 35×, at least 40×, at least 45×, at least 50×, at least 60×, at least 70×, at least 80×, at least 90×, or at least 100×. In some instances, the magnification of the one or more objective lenses may be at most 100×, at most 90×, at most 80×, at most 70×, at most 60×, at most 50×, at most 45×, at most 40×, at most 35×, at most 30×, at most 25×, at most 20×, at most 15×, at most 10×, at most 5×, or at most 2×. Any of the lower and upper values described in this paragraph may be combined to form a range included within the present disclosure, for example, in some instances the magnification of the one or more objective lenses may range from about 5× to about 25×. Those of skill in the art will recognize that the magnification of the one or more objective lenses may have any value within this range, e.g., about 7.5×.

Objective focal length: In some instances, the focal length of the one or more objective lenses may be the same or may be different, and may range between 20 mm and 200 mm. In some instances, the focal length of the one or more objective lenses may be at least 20 mm, at least 25 mm, at least 30 mm, at least 35 mm, at least 40 mm, at least 50 mm, at least 60 mm, at least 70 mm, at least 80 mm, at least 90 mm, at least 100 mm, at least 120 mm, at least 140 mm, at least 160 mm, at least 180 mm, or at least 200 mm. In some instances, the focal length of the one or more objective lenses may be at most 200 mm, at most 180 mm, at most 160 mm, at most 140 mm, at most 100 mm, at most 90 mm, at most 80 mm, at most 70 mm, at most 60 mm, at most 50 mm, at most 40 mm, at most 35 mm, at most 30 mm, at most 25 mm, or at most 20 mm. Any of the lower and upper values described in this paragraph may be combined to form a range included within the present disclosure, for example, in some instances the focal length of the one or more objective lenses may range from 25 mm to 120 mm. Those of skill in the art will recognize that the focal length of the one or more objective lenses may have any value within the range of values specified above, e.g., about 65 mm.

Objective working distance: In some instances, the working distance of the one or more objective lenses may be the same or may be different, and may range between about 100 µm and 30 mm. In some instances, the working distance may be at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 4 mm, at least 6 mm, at least 8 mm, at least 10 mm, at least 15 mm, at least 20 mm, at least 25 mm, or at least 30 mm. In some instances, the working distance may be at most 30 mm, at most 25 mm, at most 20 mm, at most 15 mm, at most 10 mm, at most 8 mm, at most 6 mm, at most 4 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm. Any of the lower and upper values described in this paragraph may be combined to form a range included within the present disclosure, for example, in some instances the working distance of the objective lens may range from 500 µm to 2 mm. Those of skill in the art will recognize that the working distance of the objective lens may have any value within the range of values specified above, e.g., about 1.25 mm.

Objective numerical aperture: In some instances, the numerical aperture of the one or more objective lenses may be the same or may be different, and may range from about 0.1 to about 1.4. In some instances, the numerical aperture may be at least 0.1, at least 0.2, at least 0.3, at least 0.4, at least 0.5, at least 0.6, at least 0.7, at least 0.8, at least 0.9, at least 1.0, at least 1.1, at least 1.2, at least 1.3, or at least 1.4. In some instances, the numerical aperture may be at most 1.4, at most 1.3, at most 1.2, at most 1.1, at most 1.0, at most 0.9, at most 0.8, at most 0.7, at most 0.6, at most 0.5, at most 0.4, at most 0.3, at most 0.2, or at most 0.1. Any of the lower and upper values described in this paragraph may be combined to form a range included within the present disclosure, for example, in some instances the numerical aperture may range from about 0.1 to about 0.6. Those of skill in the art will recognize that the numerical aperture may have any value within this range, e.g., about 0.55.

Tube lenses: In some instances, the imaging module may comprise one or more tube lenses, e.g., lenses positioned in the optical path between an objective lens (e.g., an infinity-corrected objective) and an image sensor to collimate and/or focus the light transmitted by the objective and form an image on the image sensor. In some instances, the one or more tube lenses may comprise fixed components of the imaging module. In some instances, the one or more tube lenses may be moveable (or replaceable) components of the imaging module, e.g., by mounting them on a rotating stage, mounting them on a translatable slide or stage, etc. In some instances, the one or more tube lenses may comprise both fixed and moveable (or replaceable) components of the imaging module.

Tube lens focal length: In some instances, the focal length for the one or more tube lenses may be the same or may be different, and may be at least 100 mm, at least 120 mm, at least 140 mm, at least 180 mm, at least 200 mm, at least 220 mm, at least 240 mm, at least 260 mm, at least 280 mm, at least 300 mm, at least 400 mm, at least 500 mm, or at least 600 mm.

Image sensors: In some instances, the imaging module may comprise one or more image sensors (or cameras) that may be the same or may be different, and may include any of a variety of image sensors including but not limited to, photodiode arrays, charge-coupled device (CCD) sensors or cameras, or complementary metal-oxide-semiconductor (CMOS) image sensors or cameras. In some instances, the one or more image sensors may comprise one-dimensional (linear) or two-dimensional pixel array sensors. In some instances, the one or more image sensors may comprise monochrome image sensors (e.g., configured to capture greyscale images) or color image sensors (e.g., configured to capture RGB or color images).

Image sensor pixel count: In some instances, the pixel count for the one or more image sensors may be the same or different, and may vary in terms of pixel size and pixel count. In some instances, the image resolution may depend on the pixel size and pixel count of the image sensors used. In some instances, the one or more image sensors may have a pixel count of at least 0.5 megapixels, at least 1 megapixels, at least 5 megapixels, at least 10 megapixels, at least 15 megapixels, at least 20 megapixels, at least 30 megapixels, at least 40 megapixels, at least 50 megapixels, at least 75 megapixels, at least 100 megapixels, at least 200 megapixels, at least 500 megapixels, or at least 1,000 megapixels.

Image sensor pixel size and pitch: In some instances, the pixel size and/or pitch selected for the one or more image sensors may be the same or different, and may range from about 0.1 µm to about 10 µm in at least one dimension. In some instances, the pixel size and/or pitch may be at least 0.1 µm, at least 0.5 µm, at least 1 µm, at least 2 µm, at least 3 µm, at least 4 µm, at least 5 µm, at least 6 µm, at least 7 µm, at least 8 µm, at least 9 µm, or at least 10 µm. In some instances, the pixel size and/or pitch may be at most 10 µm, at most 9 µm, at most 8 µm, at most 7 µm, at most 6 µm, at most 5 µm, at most 4 µm, at most 3 µm, at most 2 µm, at most 1 µm, at most 0.5 µm, or at most 0.1 µm. Any of the lower and upper values described in this paragraph may be combined to form a range included within the present disclosure, for example, in some instances the pixel size and/or pitch may range from about 3 µm to about 9 µm. Those of skill in the art will recognize that, in some instances, the pixel size and/or pitch may have any value within this range, e.g., about 1.4 μm.

Image sensor downsampling: In some instances, the images acquired by the one or more image sensors may be downsampled (either on-chip or through post-acquisition image processing) to reduce the image lateral resolution and/or image file size while keeping the same two-dimensional representation (or field-of-view) of the image. In some instances, the downsampled image may have a lateral resolution that is at least 2-fold, 4-fold, 6-fold, 8-fold, 10-fold, 12-fold, 14-fold, 16-fold, 18-fold, or 20-fold lower than the lateral resolution of an image acquired at full image sensor resolution. Examples of on-chip image downsampling techniques include, but are not limited to, image sensor pixel binning. Examples of image processing-based image downsampling techniques include, but are not limited to, direct downsampling, wavelet transformations, and discrete cosine transforms (see, e.g., Zhang, et al. (2011), "Interpolation-Dependent Image Downsampling", *IEEE Transactions On Image Processing*, 20(11):3291-3296; Jagadeesan, et al. (2014), "An Efficient Image Downsampling Technique Using Genetic Algorithm and Discrete Wavelet Transform", *Journal of Theoretical and Applied Information Technology* 61(3):506-514).

Acquiring a series of images: In some instances, the one or more image sensors may be used to capture single images, e.g., a single image for each decoding cycle of a plurality of decoding cycles used to decode a set of barcoded analytes. In some instances, the one or more image sensors may be used to capture a series of images, e.g., a series of images during each decoding cycle of a plurality of decoding cycles used to decode a set of barcoded analytes. In some instances, a series of images may comprise images (or video frames) that correspond to images captured before, during, and/or after an event, e.g., before, during, and/or after addition of a barcode probe to a sample being imaged. In some instances, a series of images may comprise at least 2 images, at least 3 images, at least 4 images, at least 5 images, at least 10 images, at least 20 images, at least 30 images, at least 40 images, at least 50 images, at least 100 images, at least 200 images, at least 300 images, at least 400 images, at least 500 images, at least 1,000 images, or more than 1,000 images.

Imaging frame rate: In some instances, the one or more image sensors may capture a series of images (or "frames") at a predefined image acquisition rate (or frame rate). For example, in some instances, the image acquisition rate may range from about 0.01 frames per second to about 1,000 frames per second. In some instances, the image acquisition rate may be at least 0.01 frames per second, at least 0.1 frames per second, at least 1.0 frames per second, at least 10 frames per second, at least 100 frames per second, or at least 1,000 frames per second.

Light sources: In some instances, the imaging module may comprise one or more light sources. Examples of light sources include, but are not limited to, tungsten lamps, tungsten-halogen lamps, arc lamps, lasers, light emitting diodes (LEDs), or laser diodes. In some instances, the one or more light sources may produce continuous wave, pulsed, Q-switched, chirped, frequency-modulated, and/or amplitude-modulated light at a specified wavelength (or within a specified wavelength bandpass) defined by the light source alone or in combination with one or more optical filters (e.g., one or more colored glass filters, narrowband interference filters, broadband interference filters, dichroic reflectors, diffraction gratings, etc.).

Imaging module image acquisition mode: In some instances, the imaging module may be configured to acquire images in any of a variety of imaging modes. Examples include, but are not limited to, bright-field, dark-field, fluorescence, phase contrast, or differential interference contrast (DIC), and the like, where the combination of magnification and contrast mechanism provides images having cellular or sub-cellular image resolution. In some instances, the imaging module may be configured to perform wide-field microscopic imaging (see, e.g., Combs, et al. (2017), "Fluorescence Microscopy: A Concise Guide to Current Imaging Methods", *Current Protocols in Neuroscience* 79, 2.1.1-2.1.25). In some instances, the imaging module may be configured to perform volumetric imaging (or optical sectioning) using camera-based approaches (e.g., scanned focus imaging, multi-focus imaging, extended focus imaging, etc.) or scanning-based approaches (e.g., fast three-dimensional scanning) (see, e.g., Mertz (2019), "Strategies for Volumetric Imaging with a Fluorescence Microscope", *Optica* 6(10): 1261-1268). In some instances, the optical imaging module may be configured to perform optical sectioning using light sheet microscopy (see, e.g., Combs, et al. (2017), ibid.; Power, et al. (2017), "A Guide to Light-Sheet Fluorescence Microscopy for Multiscale Imaging", *Nature Methods* 14(4):360-373).

Wide-field microscopic imaging: In some instances, the imaging module (or system comprising the imaging module) may be configured to perform wide-field microscopic imaging (e.g., epi-fluorescence microscopic imaging). Used in combination with large format cameras having high sensitivity, high dynamic range, low noise characteristics, and fast frame rates, wide-field microscopy enables fast image acquisition and good contrast at low signal levels while offering diffraction-limited (or near-diffraction-limited) spatial (lateral) resolution over large fields of view (Combs, et al. (2017), ibid.).

Volumetric imaging: In some instances, the imaging module (or system comprising the imaging module) may be configured to perform volumetric imaging (or optical sectioning). In some instances, the imaging comprises acquisition of a plurality (or "stack") of two-dimensional (2D) images to form a three-dimensional (3D) representation of the sample, where each two-dimensional image is aligned with the other images of the plurality in the sample plane (e.g., the X-Y plane), but is offset from the other two-dimensional images in a direction parallel to the optical axis of the imaging module (e.g., in the Z-direction). In some instances, the stack of images may be acquired sequentially. In some instances, the stack of images may be acquired simultaneously. In some instances, the depth-of-field of the imaging module (i.e., the distance in the Z-direction between the nearest and the farthest points that are in acceptably sharp focus in an image) may be about equal to, or smaller than, the offset (or "step size") in the Z-direction between adjacent two-dimensional images of the stack. In some instances, the depth-of-field of the two-dimensional images may be adjusted by, e.g., adjusting the numerical aperture and/or focal length of the objective lens and/or tube lens.

Light sheet microscopy: In some instances, the imaging module (or system comprising the imaging module) may be configured to perform light sheet microscopy (e.g., light sheet fluorescence microscopy (LSFM)). In LSFM, for example, excitation light is delivered in the form of a thin sheet of laser light, and emitted light is collected in an orthogonal direction, using two perpendicular objective lenses (Combs, et al. (2017), ibid.). Fluorescence is excited by the light sheet and originates from a single plane in the sample. The light sheet is then scanned relative to the sample (or the sample is scanned relative to the light sheet) to build up a volumetric image.

Imaging module compound magnification: In some instances, the compound magnification of the imaging module (i.e., the effective magnification resulting from a combination of lenses (e.g., an objective lens, tube lens, and/or additional lenses) may range from about 40× to about 1000×. In some instances, the compound magnification of the imaging module may be at least 40×, at least 50×, at least 60×, at least 70×, at least 80×, at least 90×, at least 100×, at least 200×, at least 300×, at least 400×, at least 500×, at least 600×, at least 700×, at least 800×, at least 900×, or at least 1000×. In some instances, the compound magnification of the imaging module may be at most 1000×, at most 900×, at most 800×, at most 700×, at most 600×, at most 500×, at most 400×, at most 300×, at most 200×, at most 100×, at most 90×, at most 80×, at most 70×, at most 60×, at most 50×, or at most 40×. Any of the lower and upper values described in this paragraph may be combined to form a range included within the present disclosure, for example, in some instances the compound magnification of the imaging module may range from about 50× to about 700×. Those of skill in the art will recognize that the compound magnification of the imaging module may have any value within this range, e.g., about 750×.

Imaging module field-of-view (FOV): In some instances, the FOV of the imaging module may range, for example, between about 0.2 mm and 4 mm in diameter (or in the longest dimension). In some instances, the FOV may be at least 0.2, at least 0.4, at least 0.6, at least 0.8, at least 1.0 mm, at least 1.2 mm, at least 1.4 mm, at least 1.6 mm, at least 1.8 mm, at least 2.0 mm, at least 3.0 mm, or at least 4.0 mm in diameter (or in the longest dimension). In some instances, the FOV may be at most 4.0 mm, at most 3.0 mm, at most 2.0 mm, at most 1.8 mm, or at most 1.6 mm, at most 1.4 mm, at most 1.0 mm, at most 0.8 mm, at most 0.6 mm, at most 0.4 mm, or at most 0.2 mm in diameter (or in the longest dimension). Any of the lower and upper values described in this paragraph may be combined to form a range included within the present disclosure, for example, in some instances the FOV may range from about 1.2 mm to about 3.0 mm in diameter (or in the longest dimension). Those of skill in the art will recognize that, in some instances, the FOV may have any value within the range of values specified above, e.g., about 3.2 mm in diameter (or in the longest dimension).

Imaging module lateral optical resolution: In some instances, depending on, e.g., the numerical aperture of the objective lens in use and the wavelength of the light being imaged, the lateral optical resolution of the imaging module (i.e., the minimum distance between resolvable points in the sample plane of the imaging module) may range from about 0.2 µm to about 2 µm. In some instances, the lateral optical resolution may be at least 0.2 µm, at least 0.3 µm, at least 0.4 µm, at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 2.0 µm. In some instances, the lateral optical resolution may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, at most 0.5 µm, at most 0.4 µm, at most 0.3 µm, or at most 0.2 µm. Any of the lower and upper values described in this paragraph may be combined to form a range included within the present disclosure, for example, in some instances the lateral optical resolution may range from about 0.6 µm to about 1.2 µm. Those of skill in the art will recognize that, depending on the design of the imaging module, the lateral optical resolution may have any value within this range, e.g., about 0.85 µm.

Imaging module axial optical resolution: In some instances, the axial optical resolution (or "axial resolution") of the imaging module (i.e., the minimum distance between resolvable points that are separated axially along the optical axis of the imaging module) may range from about 0.5 µm to about 2 µm. In some instances, the axial optical resolution may be at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 2.0 µm. In some instances, the axial optical resolution may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, or at most 0.5 µm. Any of the lower and upper values described in this paragraph may be combined to form a range included within the present disclosure, for example, in some instances the axial optical resolution may range from about 0.7 µm to about 1.6 µm. Those of skill in the art will recognize that, depending on the design of the imaging module, the axial optical resolution may have any value within this range, e.g., about 0.75 µm.

Depth of field: In some instances, the depth of field and/or minimum step size in the Z-direction for an imaging module (comprising, e.g., an objective lens and/or tube lens) may range from about 0.2 µm to about 5 µm, or more. In some instances, the depth of field and/or minimum step size may be at least 0.2 µm, at least 0.4 µm, at least 0.6 µm, at least 0.8 µm, at least 1.0 µm, at least 1.5 µm, at least 2.0 µm, at least 2.5 µm, at least 3.0 µm, at least 3.5 µm, at least 4.0 µm, at least 4.5 µm, or at least 5 µm, or more. In some instances, the depth of field and/or minimum step size may be at most 5 µm, at most 4.5 µm, at most 4.0 µm, at most 3.5 µm, at most 3.0 µm, at most 2.5 µm, at most 2.0 µm, at most 1.5 µm, at most 1.0 µm, at most 0.8 µm, at most 0.6 µm, at most 0.4 µm, or at most 0.2 µm. Any of the lower and upper values described in this paragraph may be combined to form a range included within the present disclosure, for example, in some instances the depth of field and/or minimum step size may range from about 0.2 µm to about 1.5 µm. Those of skill in the art will recognize that, in some instances, the depth of field and/or minimum step size may have any value within the range of values specified above, e.g., about 0.24 µm. In some instances, the minimum step size in the Z-direction may be at least 1×, 2×, 3×, 4×, 5×, 6×, 7×, 8×, 9×, 10×, 15×, or 20× the depth of field.

Fluorescence excitation wavelengths: In any of the fluorescence imaging configurations described herein, e.g., for single channel fluorescence imaging or multichannel fluorescence imaging configurations, at least one of the one or more light sources of the imaging module may produce visible light, such as green light and/or red light. In some instances, the at least one light source, alone or in combination with one or more optical components, e.g., excitation optical filters and/or dichroic beam splitters, may produce fluorescence excitation light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that, in some instances, the fluorescence excitation wavelength may have any value within this range of values, e.g., about 620 nm.

Fluorescence excitation light bandwidths: In any of the fluorescence imaging configurations described herein, e.g., for single channel fluorescence imaging or multichannel fluorescence imaging configurations, at least one of the one or more light sources, alone or in combination with one or more optical components, e.g., excitation optical filters and/or dichroic beam splitters, may produce fluorescence excitation light at the specified excitation wavelength within a bandwidth of ±2 nm, ±5 nm, ±10 nm, ±20 nm, ±40 nm, ±80 nm, or greater. Those of skill in the art will recognize that, in some instances, the excitation light bandwidth may have any value within this range, e.g., about ±18 nm.

Fluorescence emission bands: In some instances, a fluorescence imaging module may be configured to detect fluorescence emission produced by any of a variety of fluorophores known to those of skill in the art. Examples of suitable fluorescence dyes for use in, e.g., genotyping and nucleic acid sequencing applications (e.g., by conjugation to nucleotides, oligonucleotides, or proteins) include, but are not limited to, fluorescein, rhodamine, coumarin, cyanine, and derivatives thereof, including the cyanine derivatives cyanine dye-3 (Cy3), cyanine dye-5 (Cy5), cyanine dye-7 (Cy7), etc.

Fluorescence emission wavelengths: In any of the fluorescence imaging configurations described herein, e.g., for single channel fluorescence imaging or multichannel fluorescence imaging configurations, the one or more detection channels of the imaging module may be configured to collect emission light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that, in some instances, the emission wavelength may have any value within this range, e.g., about 825 nm.

Fluorescence emission light bandwidths: In any of the fluorescence imaging configurations described herein, e.g., for single channel fluorescence imaging or multichannel fluorescence imaging configurations, the one or more detection channels of the imaging module may be configured to collect light at the specified emission wavelength within a bandwidth of ±2 nm, ±5 nm, ±10 nm, ±20 nm, ±40 nm, ±80 nm, or greater. Those of skill in the art will recognize that, in some instances, the excitation bandwidths may have any value within this range, e.g., about ±18 nm.

Additional system components: In some instances, a system configured to implement the methods disclosed herein may comprise one or more commercial imaging instruments, one or more custom imaging modules, one or more additional processors or controllers (e.g., computers or computer systems), one or more sample carriers, one or more fluidics modules, one or more temperature control modules, one or more motion control modules (which may comprise one or more translation and/or rotation stages), one or more system control software packages, one or more data analysis (e.g., image processing) software packages, or any combination thereof. In some instances, the system may comprise an integrated system, e.g., where the different functional subsystems are mounted on a single framework or chassis, and packaged within a single housing. In some instances, the system may comprise a modular system, e.g., where the different functional subsystems are mounted on separate frameworks or chassis, and packaged in separate housings.

Sample carrier devices and adapters: In some instances, the biological sample is provided on any suitable substrate which may be fabricated from any of a variety of materials known to those of skill in the art including any transparent substrate. In some instances, a system configured to implement the methods disclosed herein may comprise one or more sample carrier devices and/or adapters configured to support or contain a sample, e.g., a tissue sample. Examples of sample carrier devices and adapters include, but are not limited to, microscope slides and/or adapters configured to mount microscope slides (with or without coverslips) on a microscope stage or automated stage (e.g., an automated translation or rotational stage), substrates, and/or adapters configured to mount slides on a microscope stage or automated stage, substrates comprising etched sample containment chambers (e.g., chambers open to the environment) and/or adapters configured to mount such substrates on a microscope stage or automated stage, flow cells and/or adapters configured to mount flow cells on a microscope stage or automated stage, or microfluidic devices and/or adapters configured to mount microfluidic devices on a microscope stage or automated stage.

In some instances, the one or more sample carrier devices may be designed for performing a variety of chemical analysis, biochemical analysis, nucleic acid analysis, cell analysis, or tissue analysis applications. In some instances, for example, flow cells and microfluidic devices may comprise a sample, e.g., a tissue sample. In some instances, flow cells and microfluidic devices may comprise a sample, e.g., a tissue sample, placed in contact with, e.g., a substrate (e.g., a surface within the flow cell or microfluidic device). In some instances, a flow cell may be a closed flow cell comprising fluid inlets and outlets, and a sample chamber or compartment that is not open to the surrounding environment. In some instances, a flow cell may be an open flow cell comprising fluid inlets and outlets, and a sample chamber or compartment that is open to and/or accessible from the surrounding environment.

In some instances, the systems disclosed herein may comprise 1, 2, 3, 4, 5, 6, 7, 8, 9, 10, or more than 10 sample carrier devices and/or adapters. In some instances, the one or more sample carrier devices may be fixed components of the disclosed systems. In some instances, the one or more sample carrier devices may be removable, exchangeable components of the disclosed systems. In some instances, the one or more sample carrier devices may be disposable or consumable components of the disclosed systems.

The sample carrier devices for the disclosed systems (e.g., microscope slides, substrates comprising one or more etched sample chambers, flow cells or microfluidic devices comprising one or more sample chambers, etc.) may be fabricated from any of a variety of materials known to those of skill in the art including, but not limited to, glass (e.g., borosilicate glass, soda lime glass, etc.), fused silica (quartz), silicon, polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives, or any combination thereof. FFKM is also known as Kalrez.

The one or more materials used to fabricate sample carrier devices for the disclosed systems (e.g., microscope slides, substrates comprising one or more etched sample chambers, flow cells or microfluidic devices comprising one or more sample chambers, etc.) are often optically transparent to facilitate use with spectroscopic or imaging-based detection techniques. In some instances, the entire sample carrier device will be optically transparent. Alternatively, in some instances, only a portion of the sample carrier device (e.g., an optically transparent "window") will be optically transparent.

The sample carrier devices for the disclosed systems (e.g., microscope slides, substrates comprising one or more etched sample chambers, flow cells or microfluidic devices comprising one or more sample chambers, etc.) may be fabricated using any of a variety of techniques known to those of skill in the art, where the choice of fabrication technique is often dependent on the choice of material used, and vice versa. Examples of suitable sample carrier device fabrication techniques include, but are not limited to, extrusion, drawing, precision computer numerical control (CNC) machining and boring, laser photoablation, photolithography in combination with wet chemical etching, deep reactive ion etching (DRIE), micro-molding, embossing, 3D-printing, thermal bonding, adhesive bonding, anodic bonding, and the like (see, e.g., Gale, et al. (2018), "A Review of Current Methods in Microfluidic Device Fabrication and Future Commercialization Prospects", *Inventions* 3, 60, 1-25).

For sample carrier devices comprising sample chambers, e.g., chambers etched into a planar substrate or chambers within a flow cell or microfluidic device, the dimensions of the sample chambers may range from about 0.1 µm to about 10 cm in length, width, and/or height (depth). In some instances, the length, width, and/or height (depth) of the sample chambers (or "micro chambers") may be at least 0.1 µm, at least 0.5 µm, at least 1 µm, at least 5 µm, at least 10 µm, at least 50 µm, at least 100 µm, at least 500 µm, at least 1 mm, at least 5 mm, at least 1 cm, at least 5 cm, or at least 10 cm. Those of skill in the art will recognize that, in some instances, the length, width, and/or height (depth) of the sample chambers may have any value within this range, e.g., about 125 µm. In some instances, the length, width, and/or height (depth) of fluid channels (or "micro channels") within microfluidic devices (e.g., fluid channels to connect sample chambers to inlets or outlets) may have any value within the same range of values listed in this paragraph.

For sample carrier devices comprising sample chambers, e.g., chambers etched into a planar substrate or chambers within a flow cell or microfluidic device, the volume of the sample chambers (or "micro chambers") may range from about 1 nL to about 1 mL. In some instances, the volume of the sample chambers may be at least 1 nL, at least 5 nL, at least 10 nL, at least 50 nL, at least 100 nL, at least 500 nL, at least 1 µL, at least 5 µL, at least 10 µL, at least 50 µL, at least 100 µL, at least 500 µL, at least 1 mL. Those of skill in the art will recognize that, in some instances, the volume of the sample chambers may have any value within this range, e.g., about 1.3 µL.

Fluidics modules and components: In some instances, a system configured to implement the methods disclosed herein may comprise one or more fluidics modules (or fluidics controllers) configured to control the delivery of fluids such as reagents and/or buffers to a sample, e.g., a sample contained within a sample carrier device. In some instances, the one or more fluidics controllers may be configured to control volumetric flow rates for one or more fluids or reagents, linear flow velocities for one or more fluids or reagents, mixing ratios for one or more fluids or reagents, or any combination thereof. Fluidics modules may comprise one or more fluid flow sensors (e.g., flow rate sensors, pressure sensors, etc.), one or more fluid flow actuators (e.g., pumps), one or more fluid flow control devices (e.g., valves), one or more processors (and associated electronics), tubing and connectors to connect the one or more fluidics modules to one or more sample carrier devices, or any combination thereof.

In some instances, different modes of fluid flow control may be utilized at different points in time during an assay or analysis method, e.g. forward flow (relative to the inlet and outlet for a sample chamber, flow cell, or microfluidic device), reverse flow, oscillating or pulsatile flow, or any combination thereof. In some instances, for example, oscillating or pulsatile flow may be applied during assay wash/rinse steps to facilitate complete and efficient exchange of fluids within one or more sample chambers, flow cells, or microfluidic devices.

Fluid flow actuation: The one or more fluidics modules may be configured to support any of a variety of fluid flow actuation mechanisms known to those of skill in the art. Examples include, but are not limited to, pressure-driven flow, electrokinetic flow, electroosmotic flow, etc.

In some instances, fluid flow through the system may be controlled using one or more pumps, e.g., positive displacement pumps (e.g., diaphragm pumps, peristaltic pumps, piston pumps, syringe pumps, rotary vane pumps, etc.), metering pumps (e.g., oscillating positive displacement pumps designed for precise flow control), centrifugal pumps (e.g., rotary impellor pumps, axial impellor pumps), or any combination thereof. In some instances, fluid flow through a sample carrier device (e.g., a microfluidic device) may be controlled using miniaturized pumps integrated into the device (e.g., comprising electromechanically- or pneumatically-actuated miniature syringe or plunger mechanisms, chemical propellants, membrane diaphragm pumps actuated pneumatically or by an external piston, pneumatically-actuated reagent pouches or bladders, or electro-osmotic pumps). In some instances, fluid flow through the system may be controlled by applying positive pressure (e.g., using a pump or by applying positive pneumatic pressure) at one or more inlets of a sample carrier device. In some instances, fluid flow through the system may be controlled by applying negative pressure (e.g., using a pump or by applying negative pneumatic pressure (i.e., a vacuum)) at one or more outlets of a sample carrier device.

In some instances, fluid flow through the sample carrier device may be controlled using electrokinetic or electroosmotic flow (e.g., fluid flow controlled by applying electric fields within the sample carrier device). Electrokinetic effects include, for example, electrophoresis (the movement of charged particles within a fluid under the influence of an applied electric field), electroosmosis (the movement of fluid under the influence of an applied electric field), and streaming potentials or streaming currents (electrical potentials or currents generated by an electrolyte fluid moving through a porous material having charged surfaces). Electroosmosis, for example, may be actuated by using an electronic power supply and electrodes to apply an electric field across the length of a fluid channel or between the inlet and outlet of a sample chamber (see, e.g., Dutta, et al. (2002), "Electroosmotic Flow Control in Complex Microgeometries", *Journal of Microelectromechanical Systems* 11(1):36-44; Ghosal (2004), "Fluid Mechanics of Electroosmotic Flow and its Effect on Band Broadening in Capillary Electrophoresis", *Electrophoresis* 25:214-228).

In some instances, the fluidics module may comprise one or more valves to facilitate the control of fluid flow to sample carrier devices. Examples of suitable valves include, but are not limited to, check valves, electromechanical two-way or three-way valves, pneumatic two-way and three-way valves, or any combination thereof. In some instances, fluid flow through a sample carrier device (e.g., a microfluidic device) may be controlled using miniaturized valves integrated into the device (e.g., one-shot "valves" fabricated using wax or polymer plugs that can be melted or dissolved, or polymer membranes that can be punctured; pinch valves constructed using a deformable membrane and pneumatic, hydraulic, magnetic, electromagnetic, or electromechanical (solenoid) actuation, one-way valves constructed using deformable membrane flaps, and miniature gate valves).

In some instances, different fluid flow rates may be utilized at different locations within a sample carrier device (e.g., a flow cell device comprising more than one sample chamber or a microfluidic device), or at different times in the assay or analysis process.

Temperature control modules: In some instances, a system configured to implement the methods disclosed herein may comprise one or more temperature control modules (or temperature controllers) configured to maintain a specified temperature within one or more sample carrier device for the purpose of facilitating the accuracy and reproducibility of assay or analysis results. Examples of temperature control components that may be incorporated into sample carrier devices and/or the system and controlled by a temperature control module include, but are not limited to, resistive heating elements, infrared light sources, Peltier heating or cooling devices, heat sinks, thermistors, thermocouples, and the like.

In some instances, the temperature control module may provide for a programmable temperature change at a specified, adjustable time prior to performing specific assay or analysis steps. In some instances, the temperature control module may provide for programmable changes in temperature over specified time intervals. In some instances, the temperature control module may further provide for cycling of temperatures between two or more set temperatures with specified frequency and ramp rates so that thermal cycling, e.g., for performing nucleic acid amplification reactions, may be performed.

In some instances, the temperature control module may be configured to maintain constant temperatures, to implement step changes in temperature, or to implement changes in temperature at a specified ramp rate over a temperature range between about 10° C. and about 95° C. In some instances, for example, the temperature within a sample carrier device may be held constant at a specified temperature of 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. (or at any temperature within this range). In some instances, the temperature within a sample carrier device may be held constant at a specified temperature to within ±0.1° C., ±0.25° C., ±0.5° C., ±1° C., ±2.5° C., or ±5° C. (or at any tolerance within this range). In some instances, the temperature within a sample carrier device (e.g., a microfluidic device) may be ramped at a rate of 0.1° C./s, 0.5° C./s, 1° C./s, 5° C./s, 10° C./s, 50° C./s, 100° C./s, 500° C./s, or 1000° C./s (or at any temperature ramp rate within this range) (see, e.g., Miralles, et al. (2013), "A Review of Heating and Temperature Control in Microfluidic Systems: Techniques and Applications", *Diagnostics* 3:33-67).

Motion control modules: In some instances, a system configured to implement the methods disclosed herein may comprise one or more motion control modules (or motion controllers) configured to control the position of one or more sample carrier devices relative to an imaging module objective lens, or to control the position of an imaging module objective lens relative to one or more sample carrier devices. In some instances, the motion control module may control the position of the sample carrier device in one dimension, two dimensions, or three dimensions (e.g., in the X-, Y-, and/or Z-directions) relative to the imaging module objective lens, or vice versa. In some instances, the motion control module may separately or additionally control a degree of rotation of the sample carrier device in one, two, or three dimensions. In some instances, the motion control module may be interfaced with an imaging module to also provide control of an autofocus mechanism. For example, the motion control module may be configured to adjust the focal plane by moving the sample carrier device and/or by moving an objective lens (or other optical component) of the imaging module. In some instances, the motion control module may be interfaced with an imaging module to reposition a sample carrier device in the sample plane (e.g., the X-Y plane) between acquisition of a series of images that are subsequently used to create a composition image having a larger effective field-of-view than that of an individual image (e.g., to perform imaging tiling). In some instances, the motion control module may be interfaced with an imaging module to reposition a sample carrier device in a direction parallel to the optical axis of the imaging module (e.g., in the Z-direction) between acquisition of a series of images that are subsequently used to create a three dimensional representation of the sample (e.g., to perform volumetric imaging).

In some instances, the motion control module may comprise one or more (e.g., one, two, three, or more than three) translation stages, one or more (e.g., one, two, three, or more than three) rotational stages, one or more (e.g., one, two, three, or more than three) linear encoders, one or more (e.g., one, two, three, or more than three) rotary encoders, associated motors and control electronics, or any combination thereof. In some instances, the motion control module may further control components of the imaging module such as an automated microscope objective lens turret or slide, an automated microscope tube lens turret or slide, or a microscope turret-mounted focus adjustment mechanism.

Suitable translation stages are commercially available from a variety of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate and reproducible positioning and imaging of, e.g., fluorescence signals when interspersing repeated steps of reagent delivery and optical detection.

System control module: In some instances, a system configured to implement the methods disclosed herein may comprise one or more system control modules (or system controllers) configured to synchronize and control data communication between other functional units of the system, e.g., the one or more imaging modules, one or more fluidics modules, one or more temperature control modules, one or more motion control modules, or any combination thereof. In some instances, a system control module may comprise one or more processors, one or more power supplies, one or more wired and/or wireless data communication interfaces, one or more memory storage devices, one or more user interface devices (e.g., keyboards, mice, displays, etc.), or any combination thereof. In some instances, the system control function may be provided by an external computer or computer system. In some instances, the one or more system control modules may interface with one or more external computers or computer systems.

System chassis and housing: As noted above, in some instances, the system may comprise an integrated system, e.g., where the different functional subsystems are mounted on a single framework or chassis, and packaged within a single housing. In some instances, the system may comprise an integrated optofluidic system. In some instances, the system may comprise a modular system, e.g., where the different functional subsystems are mounted on separate frameworks or chassis, and packaged in separate housings. The chassis may be constructed using any of a variety of materials (e.g., extruded aluminum or steel framing) and techniques (e.g., using fasteners, soldering, welding, etc.) known to those of skill in the art. Similarly, the housing (or enclosure) may be constructed using any of a variety of materials (e.g., sheet metal, plastic, etc.) and techniques (e.g., sheet metal bending, molding, etc.) known to those of skill in the art.

Software for In Situ Code Design to Minimi ze Optical Crowding:

Also disclosed herein is software (e.g., stored on a non-transitory, computer readable storage medium) configured to instruct a system to perform any of the in situ code design methods described herein. For example, as noted above, the present disclosure includes software comprising a set of instructions which, when executed by one or more processors, implement an algorithm for assigning code words to barcoded target analytes, e.g., gene transcripts, where the assignment algorithm is optimized to minimize optical crowding and distribute the total number or density of ON bits over the plurality of decoding cycles and detection channels. In some instances, the software disclosed herein may comprise system control software and/or data analysis and visualization software.

System control software: In some instances, the disclosed systems may comprise a processor or computer and computer-readable media that includes code for providing a user interface as well as manual, semi-automated, or fully-automated control of all system functions, e.g. control of one or more imaging modules (or commercial imaging instruments, e.g., microscopes), one or more fluid control modules, one or more temperature control modules, etc. As noted above, in some instances, the system processor or computer may be an integrated component of the system (e.g., a microprocessor or mother board embedded within a system control module). In some instances, the processor or computer may be a stand-alone personal computer or laptop computer. Examples of imaging system control functions that may be provided by the system control software include, but are not limited to, autofocus capability, control of illumination or excitation light exposure times and intensities, control of image acquisition rate, exposure time, data storage options, and the like. Examples of fluid flow control functions that may be provided by the system control software include, but are not limited to, volumetric fluid flow rates, fluid flow velocities, the timing and duration for sample and reagent additions, rinse steps, and the like. Examples of temperature control functions that may be provided by the system control software include, but are not limited to, specifying temperature set point(s) and control of the timing, duration, and ramp rates for temperature changes. Examples of motion control functions that may be provided by the system control software include, but are not limited to, range of travel, translation stage velocity, translation stage acceleration, translation stage positioning accuracy, degree of rotation, rate of rotation, rate of rotational acceleration, rotational stage positioning accuracy, and the like.

Data analysis software: In some instances, the disclosed systems may comprise one or more data analysis and visualization software packages. Examples include, but are not limited to image processing software, image analysis software, statistical analysis software, data visualization and display software, and the like.

Examples of image processing and analysis capability that may be provided by the software include, but are not limited to, manual, semi-automated, or fully-automated image exposure adjustment (e.g. white balance, contrast adjustment), manual, semi-automated, or fully-automated image noise adjustment (e.g., signal-averaging, filtering, and/or other noise reduction functionality, etc.), manual, semi-automated, or fully-automated edge detection and object identification (e.g., for identifying clusters of amplified template nucleic acid molecules on a substrate surface), manual, semi-automated, or fully-automated signal intensity measurements and/or thresholding in one or more detection channels (e.g., one or more fluorescence emission channels), manual, semi-automated, or fully-automated statistical analysis (e.g., for comparison of signal intensities to a reference value for base-calling purposes).

Any of a variety of image processing and analysis algorithms known to those of skill in the art may be used to implement real-time or post-processing image analysis capability. Examples include, but are not limited to, the Canny edge detection method, the Canny-Deriche edge detection method, first-order gradient edge detection methods (e.g. the Sobel operator), second order differential edge detection methods, phase congruency (phase coherence) edge detection methods, other image segmentation algorithms (e.g. intensity thresholding, intensity clustering methods, intensity histogram-based methods, etc.), feature and pattern recognition algorithms (e.g. the generalized Hough transform for detecting arbitrary shapes, the circular Hough transform, etc.), and mathematical analysis algorithms (e.g. Fourier transform, fast Fourier transform, wavelet analysis, auto-correlation, etc.), or combinations thereof.

Any of a variety of statistical analysis methods known to those of skill in the art may be used in processing data generated by performing the disclosed methods. Examples include, but are not limited to, clustering, eigenvector-based analysis, regression analysis, probabilistic graphical modeling, or any combination thereof.

In some instances, the system control and data analysis software (e.g., image processing/analysis software, statistical analysis software, etc.) may be written as separate software modules. In some instances, the system control and image processing/analysis software may be incorporated into an integrated software package.

Figure 3:
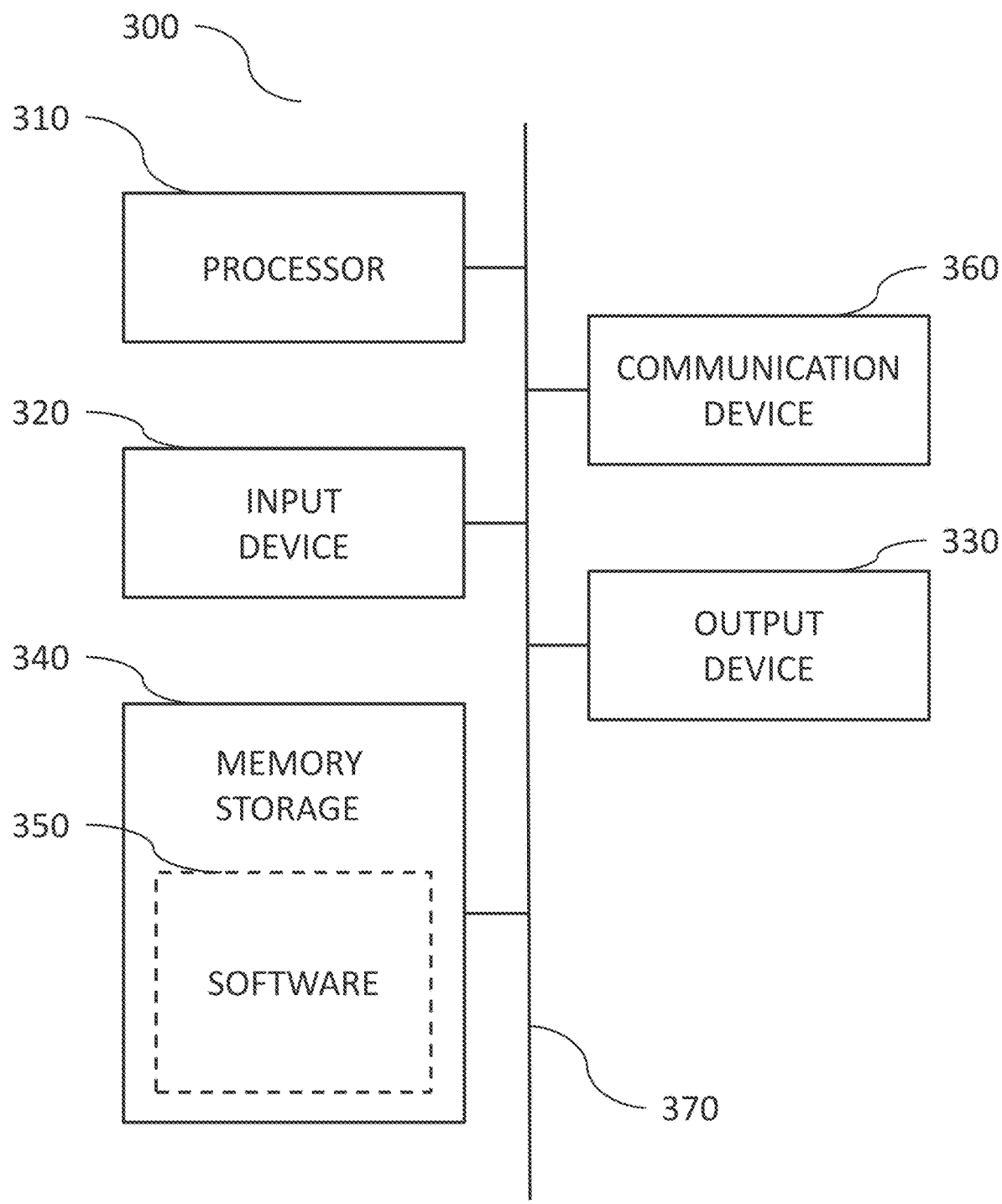
FIG. 3 provides an exemplary computing device, in accordance with some instances of the systems described herein.

Processors and Computer Systems:

FIG. 3 illustrates an example of a computing device or system in accordance with one or more examples of the disclosure. Device 300 can be a host computer connected to a network. Device 300 can be a client computer or a server. As shown in FIG. 3, device 300 can be any suitable type of microprocessor-based device, such as a personal computer, workstation, server, or handheld computing device (portable electronic device), such as a phone or tablet. The device can include, for example, one or more of processor 310, input device 320, output device 330, memory/storage 340, and communication device 360. Input device 320 and output device 330 can generally correspond to those described above, and they can either be connectable or integrated with the computer.

Input device 320 can be any suitable device that provides input, such as a touch screen, keyboard or keypad, mouse, or voice-recognition device. Output device 330 can be any suitable device that provides output, such as a touch screen, haptics device, or speaker.

Storage 340 can be any suitable device that provides storage, such as an electrical, magnetic, or optical memory including a RAM, cache, hard drive, or removable storage disk. Communication device 360 can include any suitable device capable of transmitting and receiving signals over a network, such as a network interface chip or device. The components of the computer can be connected in any suitable manner, such as via a physical bus 370 or wirelessly.

Software 350, which can be stored in memory/storage 340 and executed by processor 310, can include, for example, the programming that embodies the functionality of the present disclosure (e.g., as embodied in the devices described above).

Software 350 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 340, that can contain or store programming for use by or in connection with an instruction execution system, apparatus, or device.

Software 350 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 300 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 300 can implement any operating system suitable for operating on the network. Software 350 can be written in any suitable programming language, such as C, C++, Java, or Python. In various implementations, application software embodying the functionality of the present disclosure can be deployed in different configurations, such as in a client/server arrangement or through a web browser as a web-based application or web service, for example.

It should be appreciated that all combinations of the methods and systems described are contemplated as being part of the inventive subject matter disclosed herein. In particular, all combinations of claimed subject matter appearing in this disclosure are contemplated as being part of the inventive subject matter disclosed herein.

EXAMPLES

Figure 4:
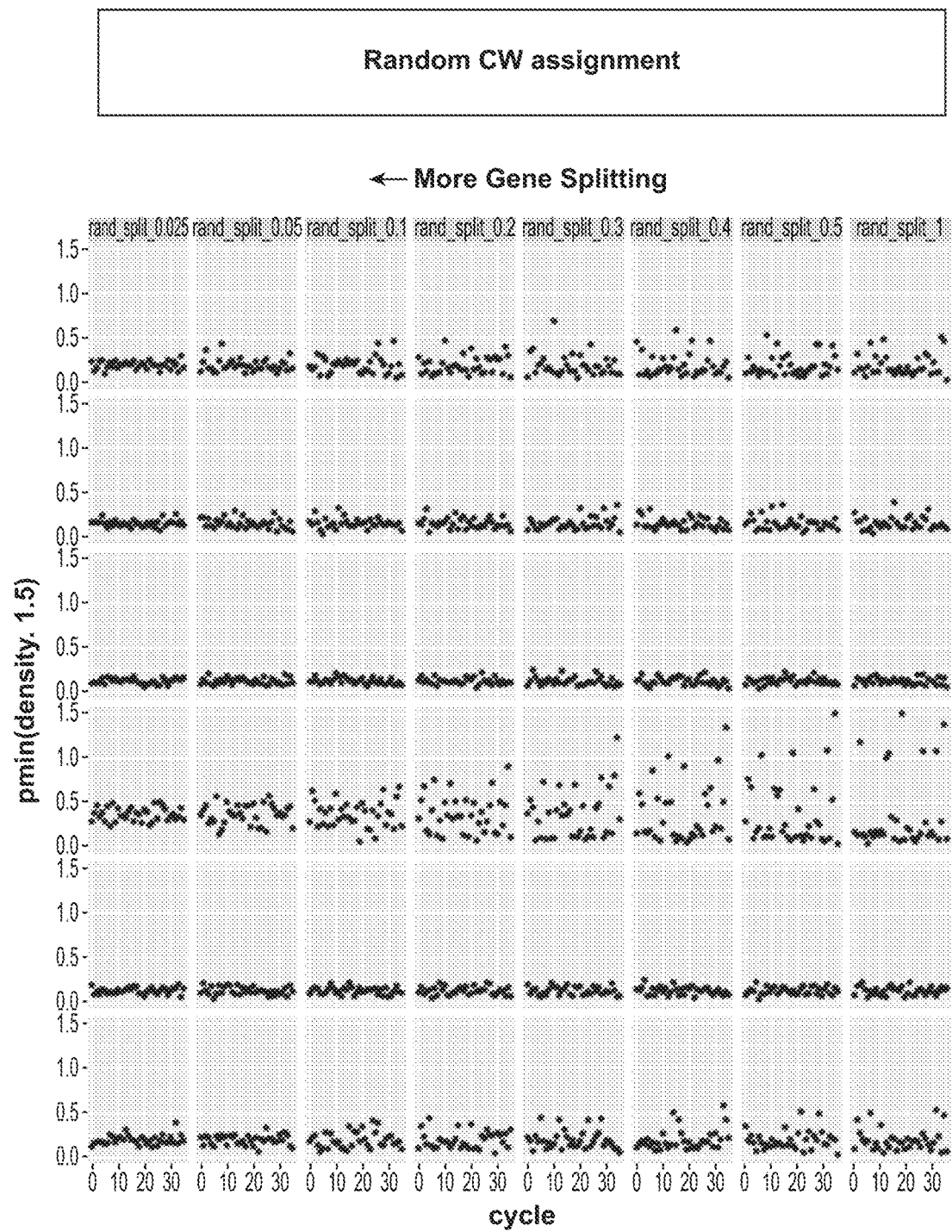
FIG. 4 provides a non-limiting example of the improvement in the even distribution of ON bits corresponding to labeled RCPs that was achieved using the optimized target analyte-code word assignment and target probe code word splitting methods disclosed herein.
Figure 4:
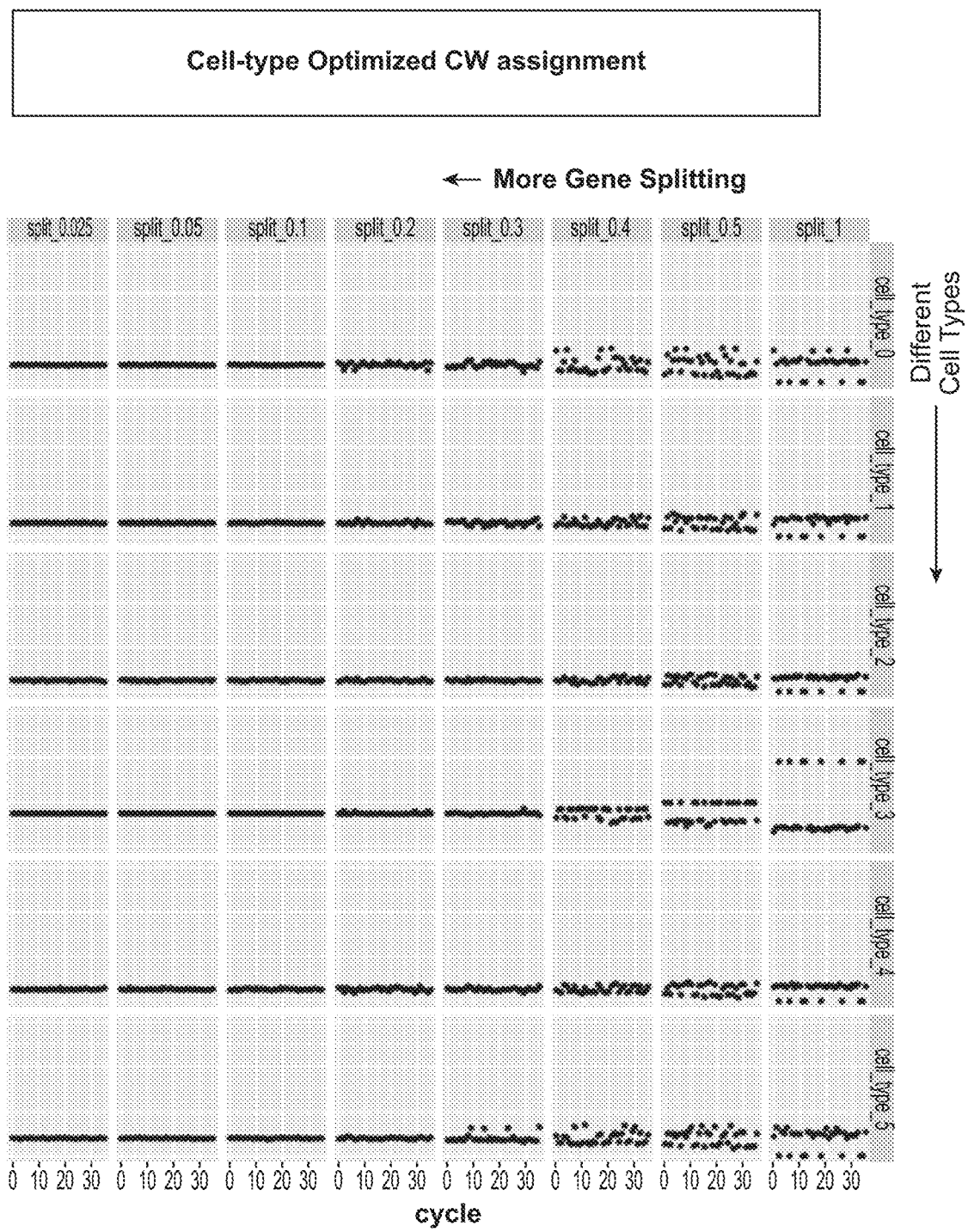

Example 1—Optimized Target Analyte-Code Word Assignment & Target Prove Code Word Splitting to Minimize Optical Crowding As described, several techniques for decoding to reduce optical crowding are described, which can be applied individually or in combination with each other. FIG. 4 provides a non-limiting example of the improvement in the even distribution of ON bits corresponding to labeled RCPs that was achieved using the optimized target analyte-code word assignment and target probe code word splitting methods disclosed herein.

FIG. 4 provides data for the parallel minimum (pmin) of the predicted spot density (i.e., the density of labeled RCPs to be detected) for multiple detection channels plotted as a function of decoding cycle number for different target probe code word splitting scenarios and different cell types, where the predicted spot density is based on single cell expression data for the targets of interest in the clustered cell types. The left half of the figure (i.e., the first eight columns) shows data for the case where code words were randomly assigned to target analytes (e.g., gene transcripts), where different cut-offs were used for target probe code word splitting in each column. The right half of the figure (i.e., columns 9-16) shows data for the case where code words were assigned to target analytes based on single cell expression data, and where again different cut-offs were used for target probe code word splitting in each column. For example, SPLIT_0.025 at the top of column 9 indicates the density threshold (pmin value) used to determine if code words for selected gene transcripts should be split. The objective in this study was to limit the density in each decoding cycle for each cell type to a maximum pmin value of 0.1. Each row in the figure corresponds to data for a different cell type. Data points plotted at a higher pmin value indicate a greater degree of optical crowding.

As can be seen in FIG. 4, the use of lower thresholds for target probe code word splitting generally results in a flatter plot (i.e., less optical crowding). Comparison of the plots in the left half of the figure to those in the right half indicates that the use of target probe code word splitting in combination with optimized assignment of code words to gene transcripts based on single cell gene expression data yields significant improvement in reducing optical crowding.

Exemplary Implementations

Exemplary methods, systems, and computer-readable storage media are set out in the following list:

1. A method for performing in situ decoding comprising:
 receiving a series of images of a biological sample, wherein the series of images comprises images from a plurality of decoding cycles;
 detecting, in the images of the series of images, a series of detectable signals (ON signals) or absence thereof (OFF signals) at one or more locations in the biological sample corresponding to one or more barcoded target analytes;
 determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identifying the one or more barcoded target analytes based on the one or more determined code words.

2. A method for performing in situ decoding comprising:
receiving a series of images of a biological sample, wherein the series of images comprises images from a plurality of decoding cycles;
detecting, in the images of the series of images, a series of detectable signals (ON signals) or absence thereof (OFF signals) at one or more locations in the biological sample corresponding to one or more barcoded target analytes;
determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule that ensures that a total number of ON signals detected in an image for a given decoding cycle is within ±20% of a mean number of ON signals detected per image for the series of images; and identifying the one or more barcoded target analytes based on the one or more determined code words.

3. The method of implementation 2, wherein the one or more code words are assigned to the one or more barcoded target analytes based on a decision rule that ensures that a total number of ON signals detected in an image for a given decoding cycle is within ±10% of a mean number of ON signals detected per image for the series of images.

4. The method of any one of implementations 1 to 3, wherein a majority of the bits in each of the one or more code words are OFF bits.

5. The method of any one of implementations 1 to 4, wherein each of the one or more code words comprises a same total number of ON bits.

6. The method of any one of implementations 2 to 5, wherein the one or more code words are assigned to the one or more barcoded target analytes based on a decision rule that also ensures that a total number of ON signals detected in a given image of the series of images corresponds to a total number of barcoded target analytes that is within ±20% of a mean number of barcoded target analytes detected per image for the series of images.

7. The method of implementation 6, wherein the one or more code words are assigned to the one or more barcoded target analytes based on a decision rule that ensures that the total number of ON signals detected in a given image of the series of images corresponds to a total number of barcoded target analytes that is within ±10% of a mean number of barcoded target analytes detected per image for the series of images.

8. The method of any one of implementations 1 to 7, wherein the decision rule for assignment of the one or more code words to the one or more barcoded target analytes further comprises assignment based on expression data for the one or more target analytes in clustered cell types, and wherein the clustered cell types represent a distribution of cell types found in the biological sample.

9. The method of implementation 8, wherein the expression data for the one or more target analytes comprises bulk gene expression data, bulk protein expression data, spatial gene expression data, spatial protein expression data, single cell gene expression data, single cell protein expression data, or any combination thereof.

10. The method of implementation 8 or implementation 9, wherein the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising:
computing a predicted density of ON signals for every combination of remaining, unassigned code words and the barcoded target analyte across the series of images;
selecting a code word from the remaining, unassigned code words that minimizes the predicted density of ON signals across the series of images; and
assigning the selected code word to the barcoded target analyte.

11. The method of implementation 10, wherein the iterative process further comprises reviewing previous assignments of code words to barcoded target analytes, and changing the code word selected for the current barcoded target analyte to minimize the predicted density of ON signals across the series of images for barcoded target analytes to which code words have been previously assigned.

12. The method of implementation 10 or implementation 11, wherein the iterative process is performed using a greedy algorithm, a simulated annealing algorithm, or a combination thereof.

13. The method of implementation 8 or implementation 9, wherein the one or more code words are rank-ordered according to code word weight, the one or more barcoded target analytes are rank-ordered according to a maximum expression level across all clustered cell types, and the lowest ranked code word is assigned to the highest ranked barcoded target analyte.

14. The method of any one of implementations 1 to 13, wherein two or more barcodes are assigned to a barcoded target analyte, and the method further comprises:
determining a code word that corresponds to one of the two or more barcodes assigned to the barcoded target analyte based on the series of ON and OFF signals detected in the series of images; and
identifying the barcoded target analyte based on the determined code word.

15. The method of implementation 14, wherein 3, 4, 5, 6, 7, 8, 9, 10, 11, 12, 13, 14, 15, or 16 barcodes are assigned to the barcoded target analyte.

16. The method of implementation 14 or implementation 15, further comprising determining a logical OR code word that corresponds to two of the two or more barcodes assigned to the barcoded target analyte based on the series of ON and OFF signals detected in the series of images; and identifying the barcoded target analyte based on the logical OR code word.

17. The method of any one of implementations 14 to 16, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

18. The method of any one of implementations 8 to 17, wherein an error rate for decoding the one or more barcoded target analytes is reduced compared to that when the one or more code words are randomly assigned to the one or more barcoded target analytes.

19. The method of any one of implementations 1 to 18, wherein the identification of the one or more barcoded target analytes comprises a qualitative detection of the one or more barcoded target analytes.

20. The method of any one of implementations 1 to 18, wherein the identification of the one or more barcoded target analytes comprises a quantitative detection of the one or more barcoded target analytes.

21. The method of any one of implementations 1 to 20, wherein the detectable signal comprises a fluorescence signal.

22. The method of any one of implementations 1 to 21, wherein each code word comprises N×K bits, where N is the number of decoding cycles and K is the number of detection channels.

23. The method of any one of implementations 1 to 22, wherein the barcoded target analytes comprise barcoded gene sequences, barcoded gene transcripts, barcoded proteins, or any combination thereof.

24. A method comprising:
    contacting a biological sample with a plurality of primary probes configured to hybridize to a plurality of target analytes, wherein each primary probe comprises a target analyte-specific barcode sequence and an anchor probe binding sequence;
    performing in situ rolling circle amplification (RCA) to produce a plurality of rolling circle amplification produces (RCPs) within the biological sample, each RCP comprising multiple copies of a target analyte sequence, a target analyte-specific barcode sequence, and an anchor probe binding sequence;
    contacting the plurality of RCPs within the biological sample with a first detectably labeled anchor probe configured to hybridize to anchor probe binding sequences present in all or a portion of the plurality of RCPs; and
    for each of a plurality of decoding cycles, performing the steps of:
        contacting the plurality of RCPs within the biological sample with a plurality of bridge probes, each configured to hybridize to a target analyte-specific barcode sequence present within the plurality of RCPs;
        contacting the hybridized bridge probes with a plurality of detectably labeled detection probes, each configured to hybridize to one or more bridge probes of the plurality of hybridized bridge probes;
        acquiring an image of the biological sample in each decoding cycle of the plurality of decoding cycles to obtain a series of images;
        detecting, in the images of the series of images, a series of detectable signals (ON signals) or absence thereof (OFF signals) at one or more locations in the biological sample corresponding to one or more barcoded target analytes;
        determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images based on a minimax decision rule; and
        identifying the one or more barcoded target analytes based on the one or more determined code words.

25. The method of implementation 24, wherein the plurality of bridge probes may be different for different decoding cycles.

26. The method of implementation 24 or implementation 25, wherein the plurality of detectably labeled detection probes may be different for different decoding cycles.

27. The method of any one of implementations 24 to 26, wherein a majority of the bits in each code word for the one or more barcoded target analytes are OFF bits.

28. The method of any one of implementations 24 to 27, wherein each of the one or more code words comprises a same total number of ON bits.

29. The method of any one of implementations 24 to 28, wherein the decision rule for assignment of the one or more code words to the one or more barcoded target analytes further comprises assignment based on expression data for the one or more target analytes in clustered cell types, and wherein the clustered cell types represent a distribution of cell types found in the biological sample.

30. The method of implementation 29, wherein the expression data for the one or more target analytes comprises bulk gene expression data, bulk protein expression data, spatial gene expression data, spatial protein expression data, single cell gene expression data, single cell protein expression data, or any combination thereof.

31. The method of implementation 29 or implementation 30, wherein the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising:
    computing a predicted density of ON signals for every combination of remaining, unassigned code words and the barcoded target analyte across the series of images;
    selecting a code word from the remaining, unassigned code words that minimizes the predicted density of ON signals across the series of images; and
    assigning the selected code word to the barcoded target analyte.

32. The method of implementation 31, wherein the iterative process further comprises reviewing previous assignments of code words to barcoded target analytes, and changing the code word selected for the current barcoded target analyte to minimize the predicted density of ON signals across the series of images for barcoded target analytes to which code words have been previously assigned.

33. The method of implementation 31 or implementation 32, wherein the iterative process is performed using a greedy algorithm, a simulated annealing algorithm, or a combination thereof.

34. The method of implementation 29 or implementation 30, wherein the one or more code words are rank ordered according to code word weight, the one or more barcoded target analytes are rank ordered according to their corresponding single cell expression data, and the lowest ranked code word is assigned to the highest ranked barcoded target analyte.

35. The method of any one of implementations 24 to 34, wherein two or more barcodes are assigned to a barcoded target analyte, and the method further comprises:
    determining a code word that corresponds to one of the two or more barcodes assigned to the barcoded target analyte based on the series of ON and OFF signals detected in the series of images; and identifying the barcoded target analyte based on the determined code word.

36. The method of implementation 35, wherein the method further comprises generating a logical OR code word that corresponds to two of the two or more barcodes assigned to the barcoded target analyte based on the series of ON and OFF signals detected at the one or more locations; and identifying the barcoded target analyte based on the logical OR code word.

37. The method of implementation 35 or implementation 36, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

38. A system comprising:
one or more processors; and
a memory communicatively coupled to the one or more processors and configured to store instructions that, when executed by the one or more processors, cause the system to:
receive a series of images of a biological sample, wherein the series of images comprises images from a plurality of decoding cycles;
detect, in the images of the series of images, a series of detectable signals (ON signals) or absence thereof (OFF signals) at one or more locations in the biological sample corresponding to one or more barcoded target analytes;
determine, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and
identify the one or more barcoded target analytes based on the one or more determined code words.

39. The system of implementation 38, wherein a majority of the bits in each code word for the one or more barcoded target analytes are OFF bits.

40. The system of implementation 38 or implementation 39, wherein each of the one or more code words comprises a same total number of ON bits.

41. The system of any one of implementations 38 to 40, wherein the decision rule for assignment of the one or more code words to the one or more barcoded target analytes further comprises assignment based on expression data for the one or more target analytes in clustered cell types, and wherein the clustered cell types represent a distribution of cell types found in the biological sample.

42. The system of implementation 41, wherein the expression data for the one or more target analytes comprises bulk gene expression data, bulk protein expression data, spatial gene expression data, spatial protein expression data, single cell gene expression data, single cell protein expression data, or any combination thereof.

43. The system of implementation 41 or implementation 42, wherein the instructions, when executed by the one or more processors, cause the system to rank-order the one or more code words according to code word weight, rank-order the one or more barcoded target analytes according to a maximum expression level across all clustered cell types, and assign the one or more rank-ordered code words to the one or more rank-ordered barcoded target analytes using an iterative process repeated for each of the one or more barcoded target analytes in decreasing order of maximum expression level, the iterative process comprising:
computing a predicted density of ON signals for every combination of remaining, unassigned code words and the barcoded target analyte across the series of images;
selecting a code word from the remaining, unassigned code words that minimizes the predicted density of ON signals across the series of images; and
assigning the selected code word to the barcoded target analyte.

44. The system of implementation 43, wherein the iterative process further comprises reviewing previous assignments of code words to barcoded target analytes, and changing the code word selected for the current barcoded target analyte to minimize the predicted density of ON signals across the series of images for barcoded target analytes to which code words have been previously assigned.

45. The system of implementation 43 or implementation 44, wherein the iterative process is performed using a greedy algorithm, a simulated annealing algorithm, or a combination thereof.

46. The system of any one of implementations 38 to 45, wherein two or more barcodes are assigned to a barcoded target analyte, and the instructions, when executed by the one or more processors, cause the system to:
determining a code word that corresponds to one of the two or more barcodes assigned to the barcoded target analyte based on the series of ON and OFF signals detected in the series of images; and
identify the barcoded target analyte based on the determined code word.

47. The system of implementation 46, wherein the instructions, when executed by the one or more processors, further cause the system to detect a logical OR code word that corresponds to two of the two or more barcodes assigned to the barcoded target analyte based on the series of ON and OFF signals detected in the series of images; and identify the barcoded target analyte based on the logical OR code word.

48. The system of implementation 46 or implementation 47, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

49. A non-transitory computer-readable storage medium storing one or more programs, the one or more programs comprising instructions, which when executed by one or more processors of a system, cause the system to:
receive a series of images of a biological sample, wherein the series of images comprises images from a plurality of decoding cycles;
detect, in the images of the series of images, a series of detectable signals (ON signals) or absence thereof (OFF signals) at one or more locations in the biological sample corresponding to one or more barcoded target analytes;
determine, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a minimax decision rule designed to minimize a maximum predicted density of ON signals detected in the images of the series of images; and identify the one or more barcoded target analytes based on the one or more determined code words.

50. The non-transitory computer-readable medium of implementation 49, wherein a majority of the bits in each code word for the one or more barcoded target analytes are OFF bits.

51. The non-transitory computer-readable medium of implementation 49 or implementation 50, wherein each of the one or more code words comprises a same total number of ON bits.

52. The non-transitory computer-readable medium of any one of implementations 49 to 51, wherein the decision rule for assignment of the one or more code words to the one or more barcoded target analytes further comprises assignment based on expression data for the one or more target analytes in clustered cell types, and wherein the clustered cell types represent a distribution of cell types found in the biological sample.

53. The non-transitory computer-readable medium of implementation 52, wherein the expression data for the one or more target analytes comprises bulk gene expression data, bulk protein expression data, spatial gene expression data, spatial protein expression data, single cell gene expression data, single cell protein expression data, or any combination thereof.

54. The non-transitory computer readable medium of implementation 52 or implementation 53, wherein the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising:

computing a predicted density of ON signals for every combination of remaining, unassigned code words and the barcoded target analyte across the series of images;

selecting a code word from the remaining, unassigned code words that minimizes the predicted density of ON signals across the series of images; and assigning the selected code word to the barcoded target analyte.

55. The non-transitory computer-readable medium of implementation 54, wherein the iterative process further comprises reviewing previous assignments of code words to barcoded target analytes, and changing the code word selected for the current barcoded target analyte to minimize the predicted density of ON signals across the series of images for barcoded target analytes to which code words have been previously assigned.

56. The non-transitory computer-readable medium of implementation 54 or implementation 55, wherein the iterative process is performed using a greedy algorithm, a simulated annealing algorithm, or a combination thereof.

57. The non-transitory computer-readable medium of any one of implementations 49 to 56, wherein two or more barcodes are assigned to a barcoded target analyte, and the instructions, when executed by one or more processors of a system, cause the system to:

determine a code word that corresponds to one of the two or more barcodes assigned to the barcoded target analyte based on the series of ON and OFF signals detected in the series of images; and identify the barcoded target analyte based on the determined code word.

58. The non-transitory computer-readable medium of implementation 57, wherein the instructions, when executed by one or more processors of a system, further cause the system to detect a logical OR code word that corresponds to two of the two or more barcodes assigned to the barcoded target analyte based on the series of ON and OFF signals detected in the series of images; and identify the barcoded target analyte based on the logical OR code word.

59. The non-transitory computer-readable medium of implementation 57 or implementation 58, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes.

60. A method for designing a panel of in situ detection probes comprising:

generating a codebook comprising a plurality of code words, wherein each code word comprises a series of ON and OFF bits;

assigning a unique code word from the codebook to each of a panel of unique target analytes, wherein the unique code words are assigned to the unique target analytes based on a minimax decision rule designed to minimize a maximum predicted density of ON signals corresponding to ON bits detected in images acquired in each cycle of a plurality of decoding cycles used to decode a corresponding panel of barcoded target analytes; and selecting a panel of in situ detection probes, wherein each in situ detection probe of the panel comprises a target recognition element and a target-specific barcode sequence that corresponds to the target-specific code word.

61. A method for designing a panel of in situ detection probes comprising:

generating a codebook comprising a plurality of code words, wherein each code word comprises a series of ON and OFF bits;

assigning a unique code word from the codebook to each of a panel of unique target analytes, wherein the unique code words are assigned to the unique target analytes based on a decision rule that ensures that a total number of ON signals corresponding to ON bits detected in an image for a given decoding cycle is within ±20% of a mean number of ON signals detected per image in images acquired in each cycle of a plurality of decoding cycles used to decode a corresponding panel of barcoded target analytes; and selecting a panel of in situ detection probes, wherein each in situ detection probe of the panel comprises a target recognition element and a target-specific barcode sequence that corresponds to the target-specific code word.

62. The method of implementation 60 or implementation 61, wherein the unique code words are assigned to the unique target analytes based on a decision rule that ensures that a total number of ON signals detected in an image for a given decoding cycle is within ±10% of a mean number of ON signals corresponding to ON bits detected per image in the images acquired in each cycle of a plurality of decoding cycles used to decode a corresponding panel of barcoded target analytes.

63. The method of any one of implementations 60 to 62, wherein a majority of the bits in each of the one or more code words are OFF bits.

64. The method of any one of implementations 60 to 63, wherein each of the one or more code words comprises a same total number of ON bits.

65. The method of any one of implementations 61 to 64, wherein the unique code words are assigned to the unique target analytes based on a decision rule that also ensures that a total number of ON signals detected in a given image corresponds to a total number of corresponding barcoded target analytes that is within ±20% of a mean number of corresponding barcoded target analytes detected per image in the images acquired in each cycle of the plurality of decoding cycles.

66. The method of implementation 65, wherein the unique code words are assigned to the unique target analytes based on a decision rule that ensures that the total number of ON signals detected in a given image of the series of images corresponds to a total number of corresponding barcoded target analytes that is within ±10% of a mean number of corresponding barcoded target analytes detected per image in the images acquired in each cycle of the plurality of decoding cycles.

67. The method of any one of implementations 60 to 66, wherein the decision rule for assignment of the unique code words to the unique target analytes further comprises assignment based on expression data for the panel of unique target analytes in clustered cell types, and wherein the clustered cell types represent a distribution of cell types found in a biological sample.

68. The method of implementation 67, wherein the expression data for the panel of unique target analytes comprises bulk gene expression data, bulk protein expression data, spatial gene expression data, spatial protein expression data, single cell gene expression data, single cell protein expression data, or any combination thereof.

69. The method of implementation 67 or implementation 68, wherein the panel of unique target analytes are rank-ordered according to a maximum expression level across all clustered cell types, and the unique code words are assigned to the panel of rank-ordered target analytes using an iterative process repeated for each of the target analytes in decreasing order of maximum expression level, the iterative process comprising:
  computing a predicted density of ON signals corresponding to detected ON bits for every remaining, unassigned code word and the target analyte across the images acquired in each cycle of the plurality of decoding cycles and across cell types;
  selecting a code word from the remaining, unassigned code words that minimizes a predicted density of ON signals corresponding to detected ON bits across the images acquired in each cycle of the plurality of decoding cycles and across cell types; and
  assigning the selected code word to the target analyte.

70. The method of implementation 69, wherein the iterative process further comprises reviewing previous assignments of unique code words to target analytes, and changing the code word selected for a current target analyte to minimize the predicted density of ON signals corresponding to detected ON bits across the across the images acquired in each cycle of the plurality of decoding for target analytes to which code words have been previously assigned.

71. The method of implementation 69 or implementation 70, wherein the iterative process is performed using a greedy algorithm, a simulated annealing algorithm, or a combination thereof.

72. The method of implementation 67 or implementation 68, wherein the unique code words are rank-ordered according to code word weight, the unique target analytes are rank-ordered according to a maximum expression level across all clustered cell types, and the lowest ranked code word is assigned to the highest ranked barcoded target analyte.

73. The method of any one of implementations 60 to 72, wherein two or more code words are assigned to a target analyte, thereby enabling identification of the target analyte by determining at least one of the two or more code words based on the series of ON and OFF signals detected in the images acquired in the plurality of decoding cycles.

74. The method of implementation 73, wherein 3, 4, 5, 6, 7, 8, 9, 10, 11, 12, 13, 14, 15, or 16 code words are assigned to the given target analyte.

75. The method of implementation 73 or implementation 74, further comprising assigning a logical OR code word that corresponds to two of the two or more code words assigned to the target analyte, thereby enabling identification of the target analyte by detecting the logical OR code word based on the series of ON and OFF signals detected in the images acquired in the plurality of decoding cycles.

76. The method of any one of implementations 73 to 75, wherein all of the bits for a code word assigned to a target analyte are OFF bits, thereby ensuring that no ON signal is detected for the code word in the images acquired in the plurality of decoding cycles and reducing a sensitivity of detecting one or more target analytes.

77. The method of any one of implementations 60 to 76, wherein synthesis of the panel of in situ detection probes comprises use of automated, solid-phase oligonucleotide synthesis.

78. The method of any one of implementations 60 to 77, wherein selecting a panel further comprises synthesis of the panel of in situ detection probes.

79. A panel of in situ detection probes comprising:
  a plurality of probes, each configured to hybridize or bind to a target analyte of a plurality of target analytes and comprising a target recognition element and a target-specific barcode sequence,
  wherein the target-specific barcode sequence corresponds to a target-specific code word comprising a series of ON and OFF bits that has been selected from a codebook comprising a plurality of code words and has been assigned to a target analyte of the plurality based on a minimax decision rule designed to minimize a maximum predicted density of ON signals corresponding to ON bits detected in images acquired in each cycle of a plurality of decoding cycles used to decode a corresponding plurality of barcoded target analytes.

80. A panel of in situ detection probes comprising:
  a plurality of probes, each configured to hybridize or bind to a target analyte of a plurality of target analytes and comprising a target recognition element and a target-specific barcode sequence,
  wherein the target-specific barcode sequence corresponds to a target-specific code word comprising a series of ON and OFF bits that has been selected from a codebook comprising a plurality of code words and has been assigned to a target analyte of the plurality based on a decision rule that ensures that a total number of ON signals corresponding to ON bits detected in an image for a given decoding cycle is within ±20% of a mean number of ON signals detected per image in images acquired in each cycle of a plurality of decoding cycles used to decode a corresponding plurality of barcoded target analytes.

81. A method for performing in situ decoding comprising:
receiving a series of images of a biological sample, wherein the series of images comprises images from a plurality of decoding cycles;
detecting, in the images of the series of images, a series of detectable signals (ON signals) or absence thereof (OFF signals) at one or more locations in the biological sample corresponding to one or more barcoded target analytes;
determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule for assignment based on expression data for the one or more target analytes in clustered cell types, and wherein the clustered cell types represent a distribution of cell types found in the biological sample; and
identifying the one or more barcoded target analytes based on the one or more determined code words.

82. The method of implementation 80, wherein the expression data for the one or more target analytes comprises bulk gene expression data, bulk protein expression data, spatial gene expression data, spatial protein expression data, single cell gene expression data, single cell protein expression data, or any combination thereof.

83. The method of implementation 81 or implementation 82, wherein the one or more code words are rank-ordered according to code word weight, the one or more barcoded target analytes are rank-ordered according to a maximum expression level across all clustered cell types, and the one or more rank-ordered code words are assigned to the one or more rank-ordered barcoded target analytes using an iterative process repeated for each of the one or more barcoded target analytes in decreasing order of maximum expression level, the iterative process comprising:
computing a predicted density of ON signals for every combination of remaining, unassigned code words and the barcoded target analyte across the series of images;
selecting a code word from the remaining, unassigned code words that minimizes the predicted density of ON signals across the series of images; and
assigning the selected code word to the barcoded target analyte.

84. The method of implementation 83, wherein the iterative process further comprises reviewing previous assignments of code words to barcoded target analytes, and changing the code word selected for the current barcoded target analyte to minimize the predicted density of ON signals across the series of images for barcoded target analytes to which code words have been previously assigned.

85. The method of implementation 83 or implementation 84, wherein the iterative process is performed using a greedy algorithm, a simulated annealing algorithm, or a combination thereof.

86. The method of implementation 81 or implementation 82, wherein the one or more code words are rank-ordered according to code word weight, the one or more barcoded target analytes are rank-ordered according to a maximum expression level across all clustered cell types, and the lowest ranked code word is assigned to the highest ranked barcoded target analyte.

87. A method for performing in situ decoding comprising:
receiving a series of images of a biological sample, wherein the series of images comprises images from a plurality of decoding cycles;
detecting, in the images of the series of images, a series of detectable signals (ON signals) or absence thereof (OFF signals) at one or more locations in the biological sample corresponding to one or more barcoded target analytes;
determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and identifying the one or more barcoded target analytes based on the one or more determined code words.

88. A method for performing in situ decoding comprising:
receiving a series of images of a biological sample, wherein the series of images comprises images from a plurality of decoding cycles;
detecting, in the images of the series of images, a series of detectable signals (ON signals) or absence thereof (OFF signals) at one or more locations in the biological sample corresponding to one or more barcoded target analytes;
determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and
identifying the one or more barcoded target analytes based on the one or more determined code words, wherein two or more barcodes are assigned to a barcoded target analyte, and the method further comprises:
determining a code word that corresponds to one of the two or more barcodes assigned to the barcoded target analyte based on the series of ON and OFF signals detected in the series of images;
determining a logical OR code word that corresponds to two of the two or more barcodes assigned to the barcoded target analyte based on the series of ON and OFF signals detected in the series of images; and
identifying the barcoded target analyte based on the logical OR code word; and
identifying the barcoded target analyte based on the determined code word.

89. The method of implementation 88, wherein 3, 4, 5, 6, 7, 8, 9, 10, 11, 12, 13, 14, 15, or 16 barcodes are assigned to the barcoded target analyte.

90. A method for performing in situ decoding comprising:
receiving a series of images of a biological sample, wherein the series of images comprises images from a plurality of decoding cycles;
detecting, in the images of the series of images, a series of detectable signals (ON signals) or absence thereof (OFF signals) at one or more locations in the biological sample corresponding to one or more barcoded target analytes;
determining, based on the series of ON and OFF signals detected in the series of images, a code word comprising a series of ON and OFF bits that corresponds to a barcode for each of the one or more barcoded target analytes, wherein the one or more code words are assigned to the one or more barcoded target analytes based on a decision rule; and identifying the one or more barcoded target analytes based on the one or more determined code words, wherein two or more barcodes are assigned to a barcoded target analyte, and the method further comprises:

determining a code word that corresponds to one of the two or more barcodes assigned to the barcoded target analyte based on the series of ON and OFF signals detected in the series of images, wherein all of the bits for a code word corresponding to at least one of the two or more barcodes assigned to the barcoded target analyte are OFF bits, thereby ensuring that no signal is detected for the code word in the series of images and reducing a sensitivity of detecting one or more barcoded target analytes; and identifying the barcoded target analyte based on the determined code word.

91. The method of implementation 90, wherein 3, 4, 5, 6, 7, 8, 9, 10, 11, 12, 13, 14, 15, or 16 barcodes are assigned to the barcoded target analyte.

It should be understood from the foregoing that, while particular implementations of the disclosed methods and systems have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method, comprising:
   (a) contacting a biological sample with a plurality of probes configured to hybridize to a target ribonucleic acid (RNA), wherein each of said plurality of probes are configured to hybridize to the same target gene,
   wherein a first probe of said plurality of probes hybridizes to a first transcript of said target RNA, wherein said first probe comprises a first nucleic acid barcode that is associated with a first code word that identifies said target RNA,
   wherein a second probe of said plurality of probes hybridizes to a second transcript of said target RNA, wherein said second probe comprises a second nucleic acid barcode that is associated with a second code word that identifies said target RNA,
   wherein said first nucleic acid barcode is different than said second nucleic acid barcode, and wherein said first code word is different than said second code word;
   (b) circularizing said first probe to generate a first circularized probe and circularizing said second probe to generate a second circularized probe;
   (c) performing rolling circle amplification (RCA) of said first circularized probe to generate a first RCA product at a first location of said biological sample and performing RCA of said second circularized probe to generate a second RCA product at a second location of said biological sample; and
   (d) performing a decoding process on said first RCA product and said second RCA product to obtain a first decoded barcode at said first location and a second decoded barcode at said second location.

2. The method of claim 1, further comprising using said first decoded barcode and said first code word to identify said target RNA at said first location and using said second decoded barcode and said second code word to identify said target RNA at said second location of said biological sample.

3. The method of claim 1, wherein said first nucleic acid barcode comprises a first sequence complementary to said target RNA and wherein said second nucleic acid barcode comprises a second sequence complementary to said target RNA.

4. The method of claim 1, wherein said first probe comprises a sequence complementary to a sequence of said target RNA and said first nucleic acid barcode and wherein said second probe comprises a sequence complementary to a sequence of said target RNA and said second nucleic acid barcode.

5. The method of claim 4, wherein said first probe and said second probe are each complementary to the same sequence of said target RNA.

6. The method of claim 4, wherein said first probe and said second probe are each complementary to different sequences of said target RNA.

7. The method of claim 6, wherein a third probe of said plurality of probes comprises a sequence complementary to a sequence of said target RNA and said first nucleic acid barcode, wherein said third probe hybridizes to a third transcript of said target RNA, wherein a fourth probe of said plurality of probes comprises a sequence complementary to a sequence of said target RNA and said second nucleic acid barcode, wherein said fourth probe hybridizes to a fourth transcript of said target RNA, and wherein said first probe, said second probe, said third probe, and said fourth probe are each complementary to different sequences of said target RNA.

8. The method of claim 4, wherein said first nucleic acid barcode and said second nucleic acid barcode each comprise a plurality of barcode segments.

9. The method of claim 8, wherein said first nucleic acid barcode and said second nucleic acid barcode each comprise at least four barcode segments.

10. The method of claim 1, wherein said decoding process comprises sequencing (i) said first nucleic acid barcode or a complement thereof and (ii) said second nucleic acid barcode or a complement thereof.

11. The method of claim 1, wherein said decoding process comprises sequential hybridization of detectably labeled probes that bind said first nucleic acid barcode and/or said second nucleic acid barcode.

12. The method of claim 11, wherein said detectably labeled probes directly bind said first nucleic acid barcode and/or said second nucleic acid barcode.

13. The method of claim 11, wherein said detectably labeled probes indirectly bind said first nucleic acid barcode and/or said second nucleic acid barcode via one or more intermediate probes.

14. The method of claim 1, wherein a third probe of said plurality of probes hybridizes to a third transcript of said target RNA and comprises a third nucleic acid barcode that is associated with a third code word that identifies said target RNA, wherein said third nucleic acid barcode is different than said first and said second nucleic acid barcode, and wherein said third code word is different than said first and said second code word.

15. The method of claim 14, wherein a fourth probe of said plurality of probes hybridizes to a fourth transcript of said target RNA and comprises a fourth nucleic acid barcode that is associated with a fourth code word that identifies said target RNA, wherein said fourth nucleic acid barcode is different than said first, said second, and said third nucleic acid barcode, and wherein said fourth code word is different than said first, said second, and said third code word.

16. A method, comprising:
(a) contacting a cell or tissue sample on a solid support with a plurality of padlock probes, wherein a first padlock probe of said plurality of padlock probes hybridizes to a first sequence of a target gene, wherein a second padlock probe of said plurality of padlock probes hybridizes to a second sequence of said target gene, wherein said first sequence and said second sequence are different;
wherein said first padlock probe is assigned a first code word that identifies said target gene,
wherein said second padlock probe is assigned a second code word that identifies said target gene, and
wherein said first code word is different than said second code word;
(b) circularizing: (i) said first padlock probe to generate a first circularized probe and (ii) said second padlock probe to generate a second circularized probe;
(c) performing rolling circle amplification (RCA): (i) using said first circularized probe as a template to generate a first RCA product at a first location of said cell or tissue sample, wherein said first RCA product is associated with a first transcript of said target gene, and (ii) using said second circularized probe as a template to generate a second RCA product at a second location of said cell or tissue sample, wherein said second RCA product is associated with a second transcript of said target gene; and
(d) sequencing: (i) said first RCA product to detect a first series of optical signals at said first location and (ii) said second RCA product to obtain a second series of optical signals at said second location.

17. The method of claim 16, further comprising using: (i) said first series of optical signals and said first code word to identify said target gene at said first location and (ii) said second series of optical signals and said second code word to identify said target gene at said second location of said cell or tissue sample.

18. The method of claim 16, wherein said first padlock probe comprises a first nucleic acid barcode, wherein said second padlock probe comprises a second nucleic acid barcode different than said first nucleic acid barcode, wherein sequencing said first RCA product comprises sequencing said first nucleic acid barcode or a complement thereof, and wherein sequencing said second RCA product comprises sequencing said second nucleic acid barcode or a complement thereof.

19. The method of claim 18, wherein said first nucleic acid barcode comprises a reverse complement of said first sequence of said target gene and wherein said second nucleic acid barcode comprises a reverse complement of said second sequence of said target gene.

20. The method of claim 18, wherein said first nucleic acid barcode is a first designed sequence that identifies said target gene and wherein said second nucleic acid barcode is a second designed sequence that identifies said target gene.

21. The method of claim 20, wherein said first nucleic acid barcode and said second nucleic acid barcode each comprise a plurality of barcode segments.

22. The method of claim 21, wherein said first nucleic acid barcode and said second nucleic acid barcode each comprise at least four barcode segments.

23. The method of claim 16, wherein a third padlock probe of said plurality of padlock probes hybridizes to a third target sequence of said target gene, wherein said third target sequence is different than said first and said second target sequence, wherein said third padlock probe is assigned a third code word that identifies said target gene, and wherein said third code word is different than said first and said second code word.

24. The method of claim 23, wherein a fourth padlock probe of said plurality of padlock probes hybridizes to a fourth target sequence of said target gene, wherein said fourth target sequence is different than said first, said second, and said third target sequence, wherein said fourth padlock probe is assigned a fourth code word that identifies said target gene, and wherein said fourth code word is different than said first, said second, and said third code word.

25. The method of claim 16, wherein said target gene is a target ribonucleic acid (RNA).

26. The method of claim 16, wherein said target gene is a target complementary deoxyribonucleic acid (cDNA) generated from a target RNA.

* * * * *